(12) United States Patent
Ackermann et al.

(10) Patent No.: US 10,835,748 B2
(45) Date of Patent: Nov. 17, 2020

(54) STIMULATION DEVICES AND METHODS

(71) Applicants: Oculeve, Inc., South San Francisco, CA (US); The Board of Trustees of the Leland Stanford Junior University, Stanford, CA (US)

(72) Inventors: Douglas Michael Ackermann, Reno, NV (US); James Donald Loudin, Alhambra, CA (US); Janusz Kuzma, Bayview (AU); Daniel Palanker, Sunnyvale, CA (US); Scott Franklin Wetenkamp, Los Altos, CA (US)

(73) Assignee: Oculeve, Inc., South San Francisco, CA (US)

( * ) Notice: Subject to any disclaimer, the term of this patent is extended or adjusted under 35 U.S.C. 154(b) by 63 days.

(21) Appl. No.: 15/802,319

(22) Filed: Nov. 2, 2017

(65) Prior Publication Data

US 2018/0064940 A1 Mar. 8, 2018

Related U.S. Application Data

(63) Continuation of application No. 13/441,806, filed on Apr. 6, 2012, now Pat. No. 9,821,159, which is a
(Continued)

(51) Int. Cl.
*A61N 1/36* (2006.01)
*A61N 1/372* (2006.01)
*A61N 1/375* (2006.01)

(52) U.S. Cl.
CPC ....... *A61N 1/36046* (2013.01); *A61N 1/3606* (2013.01); *A61N 1/37205* (2013.01);
(Continued)

(58) Field of Classification Search
CPC ............ A61N 1/36046; A61N 1/36057; A61N 1/3606; A61N 1/37205; A61N 1/37211; A61N 1/3756
See application file for complete search history.

(56) References Cited

U.S. PATENT DOCUMENTS 2,512,882 A 6/1950 Truesdale
2,525,381 A 10/1950 Tower
(Continued)

FOREIGN PATENT DOCUMENTS

CN 1488331 A 4/2004
CN 2693275 Y 4/2005
(Continued)

OTHER PUBLICATIONS

Acar, M. et al. (2013). "Ocular surface assessment in patients with obstructive sleep apnea-hypopnea syndrome," Sleep Breath 17(2):583-588. Published online: Jun. 5, 2012.
(Continued)

*Primary Examiner* — Amanda K Hulbert
(74) *Attorney, Agent, or Firm* — Mintz Levin Cohn Ferris Glovsky and Popeo, P.C.

(57) ABSTRACT

Described here are stimulation systems and methods for stimulating one or more anatomical targets in a patient for treatment conditions such as dry eye. The stimulation system may include a controller and a microstimulator. The components of the controller and microstimulator may be implemented in a single unit or in separate devices. When implemented separately, the controller and microstimulator may communicate wirelessly or via a wired connection. The microstimulator may generate pulses from a signal received from the controller and apply the signal via one or more electrodes to an anatomical target. In some variations, the microstimulator may include a passive generation circuit
(Continued)

configured to generate a pulse based on a signal received from the controller.

24 Claims, 31 Drawing Sheets

Related U.S. Application Data continuation-in-part of application No. 13/298,042, filed on Nov. 16, 2011, now Pat. No. 8,918,181.

(60) Provisional application No. 61/414,293, filed on Nov. 16, 2010, provisional application No. 61/433,645, filed on Jan. 18, 2011, provisional application No. 61/433,649, filed on Jan. 18, 2011, provisional application No. 61/433,652, filed on Jan. 18, 2011, provisional application No. 61/473,141, filed on Apr. 7, 2011, provisional application No. 61/523,732, filed on Aug. 15, 2011.

(52) U.S. Cl.
CPC ........ *A61N 1/36057* (2013.01); *A61N 1/3756* (2013.01); *A61N 1/37211* (2013.01)

(56) References Cited

U.S. PATENT DOCUMENTS

| | | | |
|---|---|---|---|
| 3,620,219 A | 11/1971 | Barker | |
| 3,709,228 A | 1/1973 | Barker | |
| 3,885,550 A | 5/1975 | MacLeod | |
| D257,495 S | 11/1980 | Bros et al. | |
| 4,495,676 A | 1/1985 | Hartmetz, II | |
| 4,520,825 A | 6/1985 | Thompson et al. | |
| 4,539,988 A | 9/1985 | Shirley et al. | |
| 4,590,942 A | 5/1986 | Brenman et al. | |
| 4,628,933 A | 12/1986 | Michelson | |
| 4,681,121 A | 7/1987 | Kobal | |
| 4,684,362 A | 8/1987 | Holt | |
| 4,706,680 A | 11/1987 | Keusch et al. | |
| 4,735,207 A | 4/1988 | Nambu et al. | |
| 4,777,954 A | 10/1988 | Keusch et al. | |
| 4,780,932 A | 11/1988 | Bowman et al. | |
| 4,868,154 A | 9/1989 | Gilbard et al. | |
| 4,926,880 A | 5/1990 | Claude et al. | |
| 4,957,480 A | 9/1990 | Morenings | |
| 4,988,358 A | 1/1991 | Eppley et al. | |
| 5,025,807 A | 6/1991 | Zabara | |
| 5,072,724 A | 12/1991 | Marcus | |
| 5,078,733 A | 1/1992 | Eveleigh et al. | |
| 5,090,422 A | 2/1992 | Dahl et al. | |
| 5,099,829 A | 3/1992 | Wu | |
| 5,147,284 A | 9/1992 | Fedorov et al. | |
| 5,324,316 A | 6/1994 | Schulman et al. | |
| 5,342,410 A | 8/1994 | Braverman | |
| 5,345,948 A | 9/1994 | O'Donnell, Jr. | |
| 5,352,445 A | 10/1994 | Lavaux | |
| 5,360,438 A | 11/1994 | Fisher | |
| 5,498,681 A | 3/1996 | Askari et al. | |
| 5,514,131 A | 5/1996 | Edwards et al. | |
| 5,533,470 A | 7/1996 | Rose | |
| 5,545,617 A | 8/1996 | Dartt et al. | |
| 5,571,101 A | 11/1996 | Ellman et al. | |
| 5,607,461 A | 3/1997 | Lathrop | |
| 5,611,970 A | 3/1997 | Apollonio et al. | |
| 5,640,978 A | 6/1997 | Wong | |
| 5,683,436 A | 11/1997 | Mendes et al. | |
| 5,697,957 A | 12/1997 | Noren et al. | |
| 5,707,400 A | 1/1998 | Terry et al. | |
| 5,713,833 A | 2/1998 | Milligan | |
| 5,720,773 A | 2/1998 | Lopez-Claros | |
| 5,733,282 A | 3/1998 | Ellman et al. | |
| 5,735,817 A | 4/1998 | Shantha | |
| 5,792,100 A | 8/1998 | Shantha | |
| 5,794,614 A | 8/1998 | Gruenke et al. | |
| 5,800,685 A | 9/1998 | Perrault | |
| 5,843,140 A | 12/1998 | Strojnik | |
| 5,900,407 A | 5/1999 | Yerxa et al. | |
| 5,904,658 A | 5/1999 | Niederauer et al. | |
| 5,935,155 A | 8/1999 | Humayun et al. | |
| 5,948,006 A | 9/1999 | Mann | |
| 6,001,088 A | 12/1999 | Roberts et al. | |
| 6,020,445 A | 2/2000 | Vanderlaan et al. | |
| 6,035,236 A | 3/2000 | Jarding et al. | |
| 6,050,999 A | 4/2000 | Paraschac et al. | |
| 6,051,017 A * | 4/2000 | Loeb .................. A61N 1/08 128/899 |
| 6,083,251 A | 7/2000 | Shindo | |
| 6,102,847 A | 8/2000 | Stielau | |
| 6,152,916 A | 11/2000 | Bige | |
| 6,200,626 B1 | 3/2001 | Grobe, III et al. | |
| 6,205,359 B1 | 3/2001 | Boveja | |
| 6,208,902 B1 | 3/2001 | Boveja | |
| 6,240,316 B1 | 5/2001 | Richmond et al. | |
| 6,246,911 B1 | 6/2001 | Seligman | |
| 6,270,796 B1 | 8/2001 | Weinstein | |
| 6,272,382 B1 | 8/2001 | Faltys et al. | |
| 6,275,737 B1 | 8/2001 | Mann | |
| 6,277,855 B1 | 8/2001 | Yerxa | |
| 6,284,765 B1 | 9/2001 | Caffrey | |
| 6,324,429 B1 | 11/2001 | Shire et al. | |
| 6,327,504 B1 | 12/2001 | Dolgin et al. | |
| 6,366,814 B1 | 4/2002 | Boveja et al. | |
| 6,405,079 B1 | 6/2002 | Ansarinia | |
| 6,438,398 B1 | 8/2002 | Pflugfelder et al. | |
| 6,458,157 B1 | 10/2002 | Suaning | |
| 6,505,077 B1 | 1/2003 | Kast et al. | |
| 6,526,318 B1 | 2/2003 | Ansarinia | |
| 6,535,766 B1 | 3/2003 | Thompson et al. | |
| 6,537,265 B2 | 3/2003 | Thanavala et al. | |
| 6,539,253 B2 | 3/2003 | Thompson et al. | |
| 6,562,036 B1 | 5/2003 | Ellman et al. | |
| 6,564,102 B1 | 5/2003 | Boveja | |
| 6,578,579 B2 | 6/2003 | Burnside et al. | |
| 6,604,528 B1 | 8/2003 | Duncan | |
| 6,641,799 B2 | 11/2003 | Goldberg | |
| 6,658,301 B2 | 12/2003 | Loeb et al. | |
| 6,662,052 B1 | 12/2003 | Sarwal et al. | |
| 6,684,879 B1 | 2/2004 | Coffee et al. | |
| 6,701,189 B2 | 3/2004 | Fang et al. | |
| 6,748,951 B1 | 6/2004 | Schmidt | |
| 6,792,314 B2 | 9/2004 | Byers et al. | |
| 6,829,508 B2 | 12/2004 | Schulman et al. | |
| 6,853,858 B2 | 2/2005 | Shalev | |
| 6,871,099 B1 | 3/2005 | Whitehurst et al. | |
| 6,879,859 B1 | 4/2005 | Boveja | |
| 6,885,888 B2 | 4/2005 | Rezai | |
| 6,895,279 B2 | 5/2005 | Loeb et al. | |
| 7,024,241 B1 | 4/2006 | Bornzin et al. | |
| 7,054,692 B1 | 5/2006 | Whitehurst et al. | |
| 7,067,307 B2 | 6/2006 | Hochleitner et al. | |
| 7,069,084 B2 | 6/2006 | Yee | |
| 7,117,033 B2 | 10/2006 | Shalev et al. | |
| 7,142,909 B2 | 11/2006 | Greenberg et al. | |
| 7,146,209 B2 | 12/2006 | Gross et al. | |
| 7,169,163 B2 | 1/2007 | Becker | |
| 7,190,998 B2 | 3/2007 | Shalev et al. | |
| 7,225,032 B2 | 5/2007 | Schmeling et al. | |
| 7,228,184 B2 | 6/2007 | Heath | |
| 7,247,692 B2 | 7/2007 | Laredo | |
| 7,317,947 B2 | 1/2008 | Wahlstrand et al. | |
| 7,330,762 B2 | 2/2008 | Boveja et al. | |
| 7,346,389 B1 | 3/2008 | Newsome | |
| 7,346,398 B2 | 3/2008 | Gross et al. | |
| 7,369,897 B2 | 5/2008 | Boveja et al. | |
| 7,442,191 B2 | 10/2008 | Hovda et al. | |
| 7,460,911 B2 | 12/2008 | Cosendai et al. | |
| 7,477,947 B2 | 1/2009 | Pines et al. | |
| 7,502,652 B2 | 3/2009 | Gaunt et al. | |
| 7,547,447 B2 | 6/2009 | Yiu et al. | |
| 7,565,204 B2 | 7/2009 | Matei et al. | |
| 7,599,737 B2 | 10/2009 | Yomtov et al. | |
| 7,636,597 B2 | 12/2009 | Gross et al. | |

(56) References Cited

U.S. PATENT DOCUMENTS

| | | |
|---|---|---|
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 * | 12/2010 | Whitehurst .......... A61N 1/37205 607/118 |
| 7,873,421 B2 | 1/2011 | Karell |
| 7,879,032 B1 | 2/2011 | Garito et al. |
| 7,879,079 B2 | 2/2011 | Tu et al. |
| D638,128 S | 5/2011 | Prokop et al. |
| 7,981,095 B2 | 7/2011 | Grenon et al. |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |
| 8,083,787 B2 | 12/2011 | Korb et al. |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |
| 8,231,218 B2 | 7/2012 | Hong et al. |
| 8,251,983 B2 | 8/2012 | Larson et al. |
| 8,295,529 B2 | 10/2012 | Petersen et al. |
| 8,318,070 B2 | 11/2012 | Shiah et al. |
| D681,839 S | 5/2013 | Nathanson |
| 8,489,189 B2 | 7/2013 | Tronnes |
| 8,494,641 B2 | 7/2013 | Boling et al. |
| 8,521,292 B2 * | 8/2013 | Wei .................... A61N 1/36007 607/41 |
| 8,626,298 B2 | 1/2014 | Simon |
| 8,676,324 B2 | 3/2014 | Simon et al. |
| 8,728,136 B2 | 5/2014 | Feldman |
| 8,918,181 B2 | 12/2014 | Ackermann et al. |
| 8,936,594 B2 | 1/2015 | Wolf et al. |
| 8,986,301 B2 | 3/2015 | Wolf et al. |
| 8,996,137 B2 | 3/2015 | Ackermann et al. |
| 9,079,042 B2 | 7/2015 | Tiedtke et al. |
| 9,095,723 B2 | 8/2015 | Ackermann et al. |
| 9,265,956 B2 | 2/2016 | Ackermann et al. |
| 9,440,065 B2 | 9/2016 | Ackermann et al. |
| 9,687,652 B2 | 6/2017 | Franke et al. |
| 9,717,627 B2 | 8/2017 | Kuzma et al. |
| 9,737,702 B2 | 8/2017 | Ackermann et al. |
| 9,737,712 B2 | 8/2017 | Franke et al. |
| 9,764,150 B2 | 9/2017 | Loudin et al. |
| 9,770,583 B2 | 9/2017 | Gupta et al. |
| 9,821,159 B2 | 11/2017 | Ackermann et al. |
| 9,956,397 B2 | 5/2018 | Loudin et al. |
| D826,420 S | 8/2018 | Ackermann et al. |
| 10,143,846 B2 | 12/2018 | Ackermann et al. |
| D837,396 S | 1/2019 | Ackermann et al. |
| 10,207,108 B2 | 2/2019 | Franke et al. |
| 2001/0018918 A1 | 9/2001 | Burnside et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2002/0049290 A1 | 4/2002 | Vanderbilt |
| 2002/0188331 A1 | 12/2002 | Fang et al. |
| 2003/0014089 A1 | 1/2003 | Chow et al. |
| 2003/0045909 A1 | 3/2003 | Gross et al. |
| 2003/0045911 A1 | 3/2003 | Bruchmann et al. |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0133877 A1 | 7/2003 | Levin |
| 2003/0139784 A1 | 7/2003 | Morimoto et al. |
| 2003/0176892 A1 | 9/2003 | Shalev |
| 2003/0176898 A1 | 9/2003 | Gross et al. |
| 2003/0192784 A1 | 10/2003 | Zhou et al. |
| 2003/0229381 A1 | 12/2003 | Hochmair et al. |
| 2003/0233134 A1 | 12/2003 | Greenberg et al. |
| 2003/0233135 A1 | 12/2003 | Yee |
| 2004/0050392 A1 | 3/2004 | Tu et al. |
| 2004/0059466 A1 | 3/2004 | Block et al. |
| 2004/0092992 A1 | 5/2004 | Adams et al. |
| 2004/0098036 A1 | 5/2004 | Bergersen |
| 2004/0098067 A1 | 5/2004 | Ohta et al. |
| 2004/0127942 A1 | 7/2004 | Yomtov et al. |
| 2004/0138646 A1 | 7/2004 | Walla |
| 2004/0147973 A1 | 7/2004 | Hauser et al. |
| 2004/0151930 A1 | 8/2004 | Rouns et al. |
| 2004/0220644 A1 | 11/2004 | Shalev et al. |
| 2005/0004621 A1 | 1/2005 | Boveja et al. |
| 2005/0004625 A1 | 1/2005 | Chow |
| 2005/0010250 A1 | 1/2005 | Schuler et al. |
| 2005/0010266 A1 | 1/2005 | Bogdanowicz |
| 2005/0101967 A1 | 5/2005 | Weber et al. |
| 2005/0101994 A1 | 5/2005 | Yamazaki et al. |
| 2005/0105046 A1 | 5/2005 | Tung |
| 2005/0137276 A1 | 6/2005 | Yahiaoui et al. |
| 2005/0159790 A1 | 7/2005 | Shalev |
| 2005/0165458 A1 | 7/2005 | Boveja et al. |
| 2005/0197675 A1 | 9/2005 | David et al. |
| 2005/0251061 A1 | 11/2005 | Schuler et al. |
| 2005/0256570 A1 | 11/2005 | Azar |
| 2005/0267542 A1 | 12/2005 | David et al. |
| 2005/0268472 A1 | 12/2005 | Bourilkov et al. |
| 2006/0004423 A1 | 1/2006 | Boveja et al. |
| 2006/0018872 A1 | 1/2006 | Tew et al. |
| 2006/0036296 A1 | 2/2006 | Greenberg et al. |
| 2006/0074450 A1 | 4/2006 | Boveja et al. |
| 2006/0089673 A1 | 4/2006 | Schultheiss et al. |
| 2006/0095077 A1 | 5/2006 | Tronnes et al. |
| 2006/0095108 A1 | 5/2006 | Chowdhury et al. |
| 2006/0100668 A1 | 5/2006 | Ben-David et al. |
| 2006/0107958 A1 | 5/2006 | Sleeper |
| 2006/0142822 A1 | 6/2006 | Tulgar |
| 2006/0161225 A1 | 7/2006 | Sormann et al. |
| 2006/0195169 A1 | 8/2006 | Gross et al. |
| 2006/0206155 A1 | 9/2006 | Ben-David et al. |
| 2006/0206162 A1 | 9/2006 | Wahlstrand et al. |
| 2006/0216317 A1 | 9/2006 | Reinhard et al. |
| 2006/0235430 A1 | 10/2006 | Le et al. |
| 2006/0239482 A1 | 10/2006 | Hatourn et al. |
| 2006/0259098 A1 | 11/2006 | Erickson |
| 2006/0271024 A1 | 11/2006 | Gertner et al. |
| 2006/0271108 A1 | 11/2006 | Libbus et al. |
| 2006/0276738 A1 | 12/2006 | Becker |
| 2007/0031341 A1 | 2/2007 | DiMauro et al. |
| 2007/0038250 A1 | 2/2007 | He et al. |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0083245 A1 | 4/2007 | Lamensdorf et al. |
| 2007/0112404 A1 | 5/2007 | Mann et al. |
| 2007/0123938 A1 | 5/2007 | Haller et al. |
| 2007/0135868 A1 | 6/2007 | Shi et al. |
| 2007/0150034 A1 | 6/2007 | Rooney et al. |
| 2007/0219600 A1 | 9/2007 | Gertner et al. |
| 2007/0237797 A1 | 10/2007 | Peyman |
| 2007/0237825 A1 | 10/2007 | Levy et al. |
| 2007/0248930 A1 | 10/2007 | Brawn |
| 2007/0250119 A1 | 10/2007 | Tyler et al. |
| 2007/0250135 A1 | 10/2007 | Bartz-Schmidt et al. |
| 2007/0255333 A1 | 11/2007 | Giftakis et al. |
| 2007/0276314 A1 | 11/2007 | Becker |
| 2007/0276451 A1 | 11/2007 | Rigaux |
| 2007/0295327 A1 | 12/2007 | Bottomley |
| 2007/0299420 A1 | 12/2007 | Peyman |

(56) References Cited

U.S. PATENT DOCUMENTS

| | | |
|---|---|---|
| 2007/0299462 A1 | 12/2007 | Becker |
| 2008/0009897 A1 | 1/2008 | Duran Von Arx |
| 2008/0021515 A1 | 1/2008 | Horsager et al. |
| 2008/0082057 A1 | 4/2008 | Korb et al. |
| 2008/0082131 A1 | 4/2008 | Llanos |
| 2008/0109046 A1 | 5/2008 | Lima et al. |
| 2008/0109054 A1 | 5/2008 | Hastings et al. |
| 2008/0114424 A1 | 5/2008 | Grenon et al. |
| 2008/0132933 A1 | 6/2008 | Gerber |
| 2008/0132969 A1* | 6/2008 | Bennett .......... A61N 1/0558 607/41 |
| 2008/0140141 A1 | 6/2008 | Ben-David et al. |
| 2008/0183242 A1 | 7/2008 | Tano et al. |
| 2008/0183243 A1 | 7/2008 | Shodo et al. |
| 2008/0208287 A1 | 8/2008 | Palermo et al. |
| 2008/0208335 A1 | 8/2008 | Blum et al. |
| 2008/0221642 A1 | 9/2008 | Humayun et al. |
| 2008/0269648 A1 | 10/2008 | Bock |
| 2008/0288036 A1 | 11/2008 | Greenberg et al. |
| 2008/0294066 A1 | 11/2008 | Hetling et al. |
| 2009/0005835 A1 | 1/2009 | Greenberg et al. |
| 2009/0012573 A1 | 1/2009 | Karell |
| 2009/0018582 A1 | 1/2009 | Ishikawa et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0043185 A1 | 2/2009 | McAdams et al. |
| 2009/0056709 A1 | 3/2009 | Worsoff |
| 2009/0099600 A1 | 4/2009 | Moore et al. |
| 2009/0099623 A1 | 4/2009 | Bentwich |
| 2009/0099626 A1 | 4/2009 | de Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0192575 A1 | 7/2009 | Carbunaru et al. |
| 2009/0204142 A1 | 8/2009 | Becker |
| 2009/0239235 A1 | 9/2009 | DeMaria et al. |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2009/0312818 A1 | 12/2009 | Horsager et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0100165 A1 | 4/2010 | Swanson et al. |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0211132 A1 | 8/2010 | Nimmagadda et al. |
| 2010/0241195 A1 | 9/2010 | Meadows et al. |
| 2010/0256609 A1 | 10/2010 | Hillis et al. |
| 2010/0274164 A1 | 10/2010 | Juto |
| 2010/0274224 A1 | 10/2010 | Jain et al. |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0311688 A1 | 12/2010 | Chapin et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan, Jr. et al. |
| 2011/0076775 A1 | 3/2011 | Stewart et al. |
| 2011/0077551 A1 | 3/2011 | Videbaek |
| 2011/0077698 A1 | 3/2011 | Tsampazis et al. |
| 2011/0081333 A1 | 4/2011 | Shantha et al. |
| 2011/0082518 A1 | 4/2011 | Filippello |
| 2011/0093043 A1 | 4/2011 | Torgerson et al. |
| 2011/0151393 A1 | 6/2011 | Frey, II et al. |
| 2011/0152969 A1 | 6/2011 | Zehnder et al. |
| 2011/0184490 A1 | 7/2011 | Horsager et al. |
| 2011/0202121 A1 | 8/2011 | Wen |
| 2011/0218590 A1 | 9/2011 | DeGiorgio et al. |
| 2011/0234971 A1 | 9/2011 | Yeh |
| 2011/0270067 A1 | 11/2011 | Faraji et al. |
| 2011/0270348 A1 | 11/2011 | Goetz |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313480 A1 | 12/2011 | De Vos |
| 2011/0313481 A1 | 12/2011 | De Vos |
| 2011/0313488 A1 | 12/2011 | Hincapie Ordonez et al. |
| 2012/0053648 A1 | 3/2012 | Neher et al. |
| 2012/0112903 A1 | 5/2012 | Kaib et al. |
| 2012/0130398 A1 | 5/2012 | Ackermann et al. |
| 2012/0133887 A1 | 5/2012 | Huang |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson et al. |
| 2012/0298105 A1 | 11/2012 | Osorio et al. |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1 | 1/2013 | Jenkins et al. |
| 2013/0006326 A1 | 1/2013 | Ackermann et al. |
| 2013/0053733 A1 | 2/2013 | Korb et al. |
| 2013/0053737 A1 | 2/2013 | Scerbo |
| 2013/0065765 A1 | 3/2013 | Selifonov et al. |
| 2013/0072755 A1 | 3/2013 | Papania et al. |
| 2013/0085551 A1 | 4/2013 | Bachinski et al. |
| 2013/0158451 A1 | 6/2013 | Juto et al. |
| 2013/0158626 A1 | 6/2013 | DeGiorgio et al. |
| 2013/0172790 A1 | 7/2013 | Badawi |
| 2013/0178937 A1 | 7/2013 | Vassallo et al. |
| 2013/0197321 A1 | 8/2013 | Wilson |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0274824 A1 | 10/2013 | Otto et al. |
| 2013/0274831 A1 | 10/2013 | Otto et al. |
| 2013/0304154 A1 | 11/2013 | Goodman et al. |
| 2013/0310887 A1 | 11/2013 | Curtis |
| 2013/0336557 A1 | 12/2013 | Cruzat et al. |
| 2014/0012182 A1 | 1/2014 | Shantha |
| 2014/0056815 A1 | 2/2014 | Peyman |
| 2014/0081353 A1 | 3/2014 | Cook et al. |
| 2014/0088463 A1 | 3/2014 | Wolf et al. |
| 2014/0148872 A1 | 5/2014 | Goldwasser et al. |
| 2014/0156000 A1 | 6/2014 | Campin et al. |
| 2014/0163580 A1 | 6/2014 | Tischendorf et al. |
| 2014/0214115 A1 | 7/2014 | Greiner et al. |
| 2014/0214118 A1 | 7/2014 | Greiner et al. |
| 2014/0214120 A1 | 7/2014 | Simon et al. |
| 2014/0214124 A1 | 7/2014 | Greiner et al. |
| 2014/0214125 A1 | 7/2014 | Greiner et al. |
| 2014/0257205 A1 | 9/2014 | Schaller |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0316485 A1 | 10/2014 | Ackermann et al. |
| 2014/0324147 A1 | 10/2014 | Wagner |
| 2014/0362339 A1 | 12/2014 | Imafuku |
| 2014/0371565 A1 | 12/2014 | Glasser |
| 2014/0371812 A1 | 12/2014 | Ackermann et al. |
| 2015/0088156 A1 | 3/2015 | Ackermann et al. |
| 2015/0182145 A1 | 7/2015 | Gazdzinski |

(56) References Cited

U.S. PATENT DOCUMENTS

| | | |
|---|---|---|
| 2015/0238754 A1 | 8/2015 | Loudin et al. |
| 2015/0335900 A1 | 11/2015 | Ackermann et al. |
| 2015/0343202 A1 | 12/2015 | Picaud et al. |
| 2015/0362755 A1 | 12/2015 | Lee et al. |
| 2016/0022992 A1 | 1/2016 | Franke et al. |
| 2016/0058615 A1 | 3/2016 | Camras et al. |
| 2016/0080720 A1 | 3/2016 | Fullam |
| 2016/0114163 A1 | 4/2016 | Franke et al. |
| 2016/0114172 A1 | 4/2016 | Loudin et al. |
| 2016/0121118 A1 | 5/2016 | Franke et al. |
| 2016/0158548 A1 | 6/2016 | Ackermann et al. |
| 2016/0270656 A1 | 9/2016 | Samec et al. |
| 2016/0367795 A1 | 12/2016 | Ackermann et al. |
| 2016/0367806 A1 | 12/2016 | Kahook |
| 2017/0049619 A1 | 2/2017 | Kahook |
| 2017/0157401 A1 | 6/2017 | Loudin et al. |
| 2017/0188947 A1 | 7/2017 | Connor |
| 2017/0239459 A1 | 8/2017 | Loudin et al. |
| 2017/0252563 A1 | 9/2017 | Franke et al. |
| 2017/0312521 A1 | 11/2017 | Franke et al. |
| 2017/0340884 A1 | 11/2017 | Franke et al. |
| 2017/0354536 A1 | 12/2017 | Kuzma et al. |
| 2017/0368332 A1 | 12/2017 | Ackermann et al. |
| 2017/0368333 A1 | 12/2017 | Loudin et al. |
| 2017/0368359 A1 | 12/2017 | Loudin et al. |
| 2018/0064941 A1 | 3/2018 | Ackermann et al. |
| 2018/0064942 A1 | 3/2018 | Ackermann et al. |
| 2018/0153394 A1 | 6/2018 | Franke et al. |
| 2018/0154137 A1 | 6/2018 | Ackermann et al. |
| 2018/0154161 A1 | 6/2018 | Ackermann et al. |
| 2018/0161579 A1 | 6/2018 | Franke et al. |
| 2018/0280688 A1 | 10/2018 | Loudin et al. |
| 2019/0022392 A1 | 1/2019 | Franke et al. |
| 2019/0167978 A1 | 6/2019 | Ackermann et al. |
| 2019/0217095 A1 | 7/2019 | Franke et al. |
| 2019/0290922 A1 | 9/2019 | Ackermann et al. |
| 2019/0308009 A1 | 10/2019 | Loudin et al. |
| 2019/0344077 A1 | 11/2019 | Ackermann et al. |
| 2020/0030615 A1 | 1/2020 | Loudin et al. |
| 2020/0038238 A1 | 2/2020 | Kuzma et al. |

FOREIGN PATENT DOCUMENTS

| | | |
|---|---|---|
| CN | 101087822 A | 12/2007 |
| CN | 101503491 A | 8/2009 |
| CN | 101589085 A | 11/2009 |
| CN | 101616663 A | 12/2009 |
| CN | 101829120 A | 9/2010 |
| CN | 101939043 A | 1/2011 |
| CN | 102266592 A | 12/2011 |
| CN | 103467652 A | 12/2013 |
| DE | 102006048819 A1 | 4/2008 |
| EM | 2102681 0001 | 10/2012 |
| EM | 2199000 0001 | 3/2013 |
| EP | 0109935 A1 | 5/1984 |
| EP | 1 497 483 | 1/2005 |
| EP | 1 651 307 | 5/2006 |
| EP | 1 919 553 | 5/2008 |
| EP | 1 958 661 A1 | 8/2008 |
| EP | 2 205 193 | 7/2010 |
| EP | 2 205 314 | 7/2010 |
| EP | 3263175 A1 | 1/2018 |
| GB | 2 129 690 B | 3/1987 |
| GB | 2 456 002 A | 7/2009 |
| JP | S60500241 A | 2/1985 |
| JP | S60502192 A | 12/1985 |
| JP | 8-500995 A | 2/1996 |
| JP | 2002-325851 A | 11/2002 |
| JP | 2002-539859 A | 11/2002 |
| JP | 2004-508847 A | 3/2004 |
| JP | 2004526510 A | 9/2004 |
| JP | 2005-502409 A | 1/2005 |
| JP | 2005-052461 A | 3/2005 |
| JP | 2005-144178 A | 6/2005 |
| JP | 2005521489 A | 7/2005 |
| JP | 2005-528169 A | 9/2005 |
| JP | 2006-515900 A | 6/2006 |
| JP | 2006-311917 A | 11/2006 |
| JP | 2007-044323 A | 2/2007 |
| JP | 2007-521385 A | 8/2007 |
| JP | 2007-528751 A | 10/2007 |
| JP | 2008-55000 A | 3/2008 |
| JP | 2008-183248 A | 8/2008 |
| JP | 2008-541850 A | 11/2008 |
| JP | 2009-506836 A | 2/2009 |
| JP | 2009-523503 A | 6/2009 |
| JP | 2010-505563 A | 2/2010 |
| JP | 2010-051562 A | 3/2010 |
| JP | 2010506654 A | 3/2010 |
| JP | 2010-537777 A | 12/2010 |
| JP | 2011-030734 A | 2/2011 |
| JP | 2011-524780 A | 9/2011 |
| JP | 2012-100708 A | 5/2012 |
| JP | 2012-115545 A | 6/2012 |
| JP | 2012-200558 A | 10/2012 |
| JP | 2013-528416 A | 7/2013 |
| JP | 2013-542838 A | 11/2013 |
| RU | 2338492 C1 | 11/2008 |
| WO | WO-85/01213 A1 | 3/1985 |
| WO | WO-94/00188 A1 | 1/1994 |
| WO | WO-00/01320 A2 | 1/2000 |
| WO | WO-00/56393 A1 | 9/2000 |
| WO | WO-00/62672 A1 | 10/2000 |
| WO | WO-01/05388 A2 | 1/2001 |
| WO | WO-01/85094 A2 | 11/2001 |
| WO | WO-02/078592 A2 | 10/2002 |
| WO | WO-03/023907 A1 | 3/2003 |
| WO | WO-03/082080 A2 | 10/2003 |
| WO | WO-2003/087433 A1 | 10/2003 |
| WO | WO-03/101535 A1 | 12/2003 |
| WO | WO-2004/026106 A2 | 4/2004 |
| WO | WO-2004/026106 A3 | 4/2004 |
| WO | WO-2004/043217 A2 | 5/2004 |
| WO | WO-2004/043217 A3 | 5/2004 |
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2007/028003 A2 | 3/2007 |
| WO | WO-2007/079543 A1 | 7/2007 |
| WO | WO-2008/048321 A1 | 4/2008 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/048580 A1 | 4/2009 |
| WO | WO-2009/070709 A1 | 6/2009 |
| WO | WO-2009/154457 A2 | 12/2009 |
| WO | WO-2010/003011 A1 | 1/2010 |
| WO | WO-2010/027743 A1 | 3/2010 |
| WO | WO-2010/069317 A1 | 6/2010 |
| WO | WO-2010/076904 A1 | 7/2010 |
| WO | WO-2010/099818 A1 | 9/2010 |
| WO | WO-2010/123704 A2 | 10/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2012/155188 A1 | 11/2012 |
| WO | WO-2012/174161 A1 | 12/2012 |
| WO | WO-2013/055940 A2 | 4/2013 |
| WO | WO-2013/055940 A3 | 4/2013 |
| WO | WO-2013/157320 A1 | 10/2013 |
| WO | WO-2013/162793 A1 | 10/2013 |
| WO | WO-2013/165697 A1 | 11/2013 |
| WO | WO-2013/166353 A1 | 11/2013 |
| WO | WO-2014/138709 A1 | 9/2014 |
| WO | WO-2014/153218 A1 | 9/2014 |
| WO | WO-2014/165124 A1 | 10/2014 |

(56) References Cited

FOREIGN PATENT DOCUMENTS

| WO | WO-2014/172693 A2 | 10/2014 |
|---|---|---|
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/025323 A1 | 2/2016 |
| WO | WO-2016/065211 A1 | 4/2016 |
| WO | WO-2016/065213 A1 | 4/2016 |
| WO | WO-2016/065215 A1 | 4/2016 |
| WO | WO-2017/192572 A1 | 11/2017 |

OTHER PUBLICATIONS

Amparo (2013). "Topical Interleukin 1 Receptor Antagonist for Treatment of Dry Eye Disease," JAMA Ophth. 131(6):715-723.
Cipriano et al. (2014). "Superabsorbent Hydrogels That Are Robust and Highly Stretchable," Am. Chem Soc. 47(13):4445-4452.
Eye Health (2014). "Watery eyes in cold weather," Oregon Eye Specialists, PC, located at http://www.oregoneyes.net/watery-eyes-in-cold-weather/, 3 total pages.
Friedman et al. (2016). "A nonrandomized, open-label study to evaluate the effect of nasal stimulation on tear production in subjects with dry eye disease," Clin. Ophthal. 10:795-804.
Friedman, N. J. (2010) "Impact of Dry Eye Disease and Impact on Quality of Life." *Current Opinion in Ophthalmology.* 21:310-316.
Galor, A. et al. (2014). "Environmental factors affect the risk of dry eye syndrome in a United States veteran population," Opth. 121:972-973.
Mallepally et al. (2013). "Superabsorbent Alginate Aerogels," J. Supercritical Fluids 79:1-5.
McDonald et al. (2009) "Hydroxypropyl Cellulose Ophthalmic Inserts (Lacrisert) Reduce the Signs and Symptoms of Dry Eye Syndrome and Improve Patient Quality of Life", Transactions of the American Ophthalmological Society, 107:214-222.
Olsen et al. (1998) "Human Sclera: Thickness and Surface Area". American Journal of Ophthalmology. Feb. 1998, vol. 125, Issue 2, pp. 237-241.
Petrov, A. et al. (2016). "SkQ1 Ophthalmic Solution for Dry Eye Treatment: Results of a Phase 2 Safety and Efficacy Clinical Study in the Environment and During Challenge in the Controlled Adverse Environment Model," Adv. Ther. 33:96-115.
Van Setten, G. et al. (2016). "Evidence of seasonality and effects of psychrometry in dry eye disease," Acta Opth. 94:499-506.
Yu, et al. (Apr. 2011) "The Economic Burden of Dry Eye Disease in the United States: a Decision Tree Analysis", Cornea, 30(4):379-387.
Anonymous (2007). "The epidemiology of dry eye disease: report of the Epidemiology Subcommittee of the International Dry Eye WorkShop (2007)," Ocul. Surf. 5(2):93-107.
Bajpai et al. (2012). "Preparation, Characterization and Water Uptake Behavior of Polysaccharide Based Nanoparticles," Prog. Nanotech. Nanomat. 1(1):9-17.
Baraniuk et al. (2007). "Nasonasal Reflexes, the Nasal Cycle, and Sneeze," Curr. Allergy and Asthma Reports 7:105-111.
Baroody FM, Foster KA, Markaryan A, et al. Nasal ocular reflexes and eye symptoms in patients with allergic rhinitis. Ann Allergy Asthma Immunol 2008;100:194-199.
Baroody FM, Shenaq D, DeTineo M, et al. Fluticasone furoate nasal spray reduces the nasal-ocular reflex: a mechanism for the efficacy of topical steroids in controlling allergic eye symptoms. J Allergy Clin Immunol 2009; 123:1342-1348.
Dart et al. (2002). "Effects of 25% Propylene Glycol Hydrogel (Solugel) on Second Intention Wound Healing in Horses," Vet. Surg. 31(4):309-313.
Drummond PD. Lacrimation and cutaneous vasodilatation in the face induced by painful stimulation of the nasal ala and upper lip. J Auton Nery Syst 1995;51:109-16.
Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.
Gupta et al. (1997). "Nasolacrimal Stimulation of Aqueous Tear Production," Cornea 16(6):645-648.
Harvard Health Publishing (2010). "Dry eyes and what you can try," Harvard Medical School, 2 total pages.
Heigle TJ, Pflugfelder SC. Aqueous tear production in patients with neurotrophic keratitis. Cornea 1996;15: 135-8.
Holzer P. Capsaicin: cellular targets, mechanisms of action, and selectivity for thin sensory neurons. Pharmacol Rev 1991;43: 143-201.
Ikemura et al. (2008). "UV-VIS Spectra and Photoinitiation Behaviors of Acylphosphine Oxide and Bisacylphosphine Oxide Derivatives in unfilled, Light-Cured Dental Resins," Dent. Mat. J. 27:765-774.
Krupin T, Cross DA, Becker B. Decreased basal tear production associated with general anesthesia. Arch Ophthalmol 1977;95: 107-108.
Loth S, Bende M. Effect of nasal anaesthesia on lacrimal function after nasal allergen challenge. Clin Exp Allergy 1994;24:375-376.
Pasqui et al. (2012). "Polysaccharide-Based Hydrogels: The Key Role of Water in Affecting Mechanical Properties," Polymers 4(3):1517-1534.
Philip G, Baroody FM, Proud D, et al. The human nasal response to capsaicin. J Allergy Clin Immunol 1994;94: 1035-1045.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111:106-108.
Vapor Pressure Data for H2O (2012). Handbook of Chemistry and Physics, 73rd edition, 1 total page.
Zilstorff-Pedersen (1965). "Quantitative Measurements of the Nasolacrimal Reflex," Arch. Oto. 81:457-462.
Boberg-Ans J. (1955), "Experience in clinical examination of corneal sensitivity: corneal sensitivity and the naso-lacrimal reflex after retrobulbar anaesthesia," Br. J. Ophthalmol. 39(12):705-726.
Calonge (2001). "The Treatment of Dry Eye," Survey Ophth, 45(2):S227-S239.
Corrected Notice of Allowance dated Jun. 9, 2017, for U.S. Appl. No. 14/920,860, filed Oct. 22, 2015, 2 pages.
Elsby et al. (1967). "Lacrimal Secretion in the Cat," Br, J. Pharm. Chemother. 29(1):1-7.
Extended European Search Report received for European Patent Application No. 11842076.9, dated Oct. 10, 2014, 5 pages.
Extended European Search Report received for European Patent Application No. 12768458.7, dated Aug. 28, 2014, 7 pages.
Extended European Search Report dated Oct. 21, 2016, for EP Application No. 14 778 719.6, filed on Mar. 12, 2014, 8 pages.
Extended European Search Report dated Nov. 27, 2017, for EP Application No. 17 167 504.4, filed on Apr. 6, 2012, 9 pages.
Extended European Search Report dated Jan. 8, 2018, for EP Application No. 15 824 539.9, filed on Jul. 24, 2015, 6 pages.
Final Office Action for U.S. Appl. No. 13/441,806, dated Mar. 12, 2015, 10 pages.
Final Office Action for U.S. Appl. No. 13/441,806, dated May 20, 2016, 10 pages.
Final Office Action for U.S. Appl. No. 14/816,846, dated May 11, 2016, 12 pages.
Final Office Action received for U.S. Appl. No. 14/207,072, dated Jun. 22, 2016.

(56) References Cited

OTHER PUBLICATIONS

Final Office Action dated Sep. 23, 2016, for U.S. Appl. No. 14/809,109, filed Jul. 24, 2015, 10 pages.
Final Office Action dated Feb. 1, 2017, for U.S. Appl. No. 14/920,852, filed Oct. 22, 2015, 20 pages.
Final Office Action dated Mar. 10, 2017, for U.S. Appl. No. 14/920,847, filed Oct. 22, 2015, 12 pages.
Final Office Action dated May 17, 2017, for U.S. Appl. No. 13/441,806, filed Apr. 6, 2012, 5 pages.
Final Office Action dated Sep. 1, 2017, for U.S. Appl. No. 14/816,846, filed Aug. 3, 2015, 12 pages.
Final Office Action dated Dec. 20, 2017, for U.S. Appl. No. 14/920,852, filed Oct. 22, 2015, 18 pages.
Final Office Action dated Mar. 28, 2018, for U.S. Appl. No. 15/598,063, filed May 17, 2017, 9 pages.
International Search Report & Written Opinion received for PCT Patent Application No. PCT/US2011/060989, dated Feb. 23, 2012, 16 pages.
International Search Report & Written Opinion received for PCT Patent Application No. PCT/US2014/022158, dated Jul. 30, 2014, 8 pages.
International Search Report and Written Opinion received for PCT Application No. PCT/US2015/042130, dated Oct. 28, 2015, 5 pages.
International Search Report and Written Opinion received for PCT Patent Application No. PCT/US2015/057023, dated Mar. 4, 2016, 10 pages.
International Search Report and Written Opinion received for PCT Patent Application No. PCT/US2014/024496, dated Aug. 22, 2014, 11 pages.
International Search Report received for PCT Patent Application No. PCT/US2012/32629, dated Oct. 26, 2012, 4 pages.
International Search Report dated Feb. 10, 2016, for PCT Patent Application No. Pot/US2015/57021, filed on Oct. 22, 2015, 4 pages.
International Search Report received for PCT Patent Application No. PCT/US2015/57019, dated Feb. 11, 2016, 4 pages.
Lora et al. (2009). "Lacrimal Nerve Stimulation by a Neurostimulator for Tear Production," Invest. Ophth. Vis. Science 50(13):172.
Meng, I.D. et al. (2013). "The role of corneal afferent neurons in regulating tears under normal and dry eye conditions," Exp. Eye Res. 117:79-87.
Non Final Office Action received for U.S. Appl. No. 13/441,806, dated Sep. 17, 2015, 11 pages.
Non-Final Office Action received for U.S. Appl. No. 13/298,042, dated Oct. 2, 2013, 10 pages.
Non-Final Office Action received for U.S. Appl. No. 13/441,806, dated Dec. 18, 2013, 9 pages.
Non-Final Office Action received for U.S. Appl. No. 14/201,753, dated Apr. 2, 2015, 6 pages.
Non-Final Office Action received for U.S. Appl. No. 14/809,109, dated Apr. 8, 2016, 8 pages.
Non-Final Office Action received for U.S. Appl. No. 14/816,846, dated Sep. 11, 2015, 5 pages.
Non-Final Office Action Received for U.S. Appl. No. 14/920,860, dated Aug. 17, 2016, 11 pages.
Non-Final Office Action Received for U.S. Appl. No. 14/920,652, dated Aug. 1, 2016, 20 pages.
Non Final Office Action received for U.S. Appl. No. 14/207,072, dated Dec. 9, 2015, 8 pages.
Non-Final Office Action dated Sep. 27, 2016, for U.S. Appl. No. 14/920,847, filed Oct. 22, 2015, 13 pages.
Non-Final Office Action dated Nov. 2, 2016, for U.S. Appl. No. 13/441,806, filed Apr. 6, 2012, 10 pages.
Non-Final Office Action dated Dec. 6, 2016, for U.S. Appl. No. 14/816,846, filed Aug. 3, 2015, 13 pages.
Non-Final Office Action dated Jul. 17, 2017, for U.S. Appl. No. 15/598,063, filed May 17, 2017, 9 pages.
Non-Final Office Action dated Jul. 31, 2017, for U.S. Appl. No. 14/920,852, flied Oct. 22, 2015, 16 pages.
Non-Final Office Action dated Dec. 28, 2017, for U.S. Appl. No. 15/676,910, filed Aug. 14, 2017, 10 pages.
Notice of Allowance received for U.S. Appl. No. 14/201,753, dated Dec. 15, 2015, 2 pages.
Notice of Allowance received for U.S. Appl. No. 14/201,753, dated Oct. 15, 2015, 5 pages.
Notice of Allowance received for U.S. Appl. No. 13/298,042, dated Apr. 29, 2014, 5 pages.
Notice of Allowance received for U.S. Appl. No. 13/298,042, dated Aug. 11, 2014, 7 pages.
Notice of Allowance received for U.S. Appl. No. 13/298,042, dated Nov. 13, 2014, 5 pages.
Notice of Allowance received for U.S. Appl. No. 14/561,107, dated Mar. 31, 2015, 7 pages.
Notice of Allowability dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/609,109, filed Jul. 24, 2015, 8 pages.
Notice of Allowance dated Mar. 28, 2017, for U.S. Appl. No. 14/207,072, filed Mar. 12, 2014, 8 pages.
Notice of Allowance dated Apr. 20, 2017, for U.S. Appl. No. 14/920,860, filed Oct. 22, 2015, 5 pages.
Notice of Allowance dated May 30, 2017, for U.S. Appl. No. 14/920,847, filed Oct. 22, 2015, 5 pages.
Notice of Allowance dated Aug. 2, 2017, for U.S. Appl. No. 13/441,806, filed Apr. 6, 2012, 5 pages.
Roessler et al. (2009), "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004), "Distribution of Pterygopalatine Gangiion Efferents to the Lacrimal Gland in Man," Exp. Eye Res. 78(3):329-335.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. POCT/US2012/032629, dated Oct. 26, 2012, 8 pages.
Written Opinion received for PCT Patent Application No. PCT/US2015/57021, dated Feb. 10, 2016.
Written Opinion received for PCT Patent Application No. PCT/US2015/57019, dated Feb. 11, 2016, 6 pages.
Ahmed, E. M. et al. (2013, e-published Jul. 18, 2013). "Hydrogel: Preparation, characterization, and applications: A review," Cairo University, Journal of Advanced Research (2015) 6, 105-121.

* cited by examiner

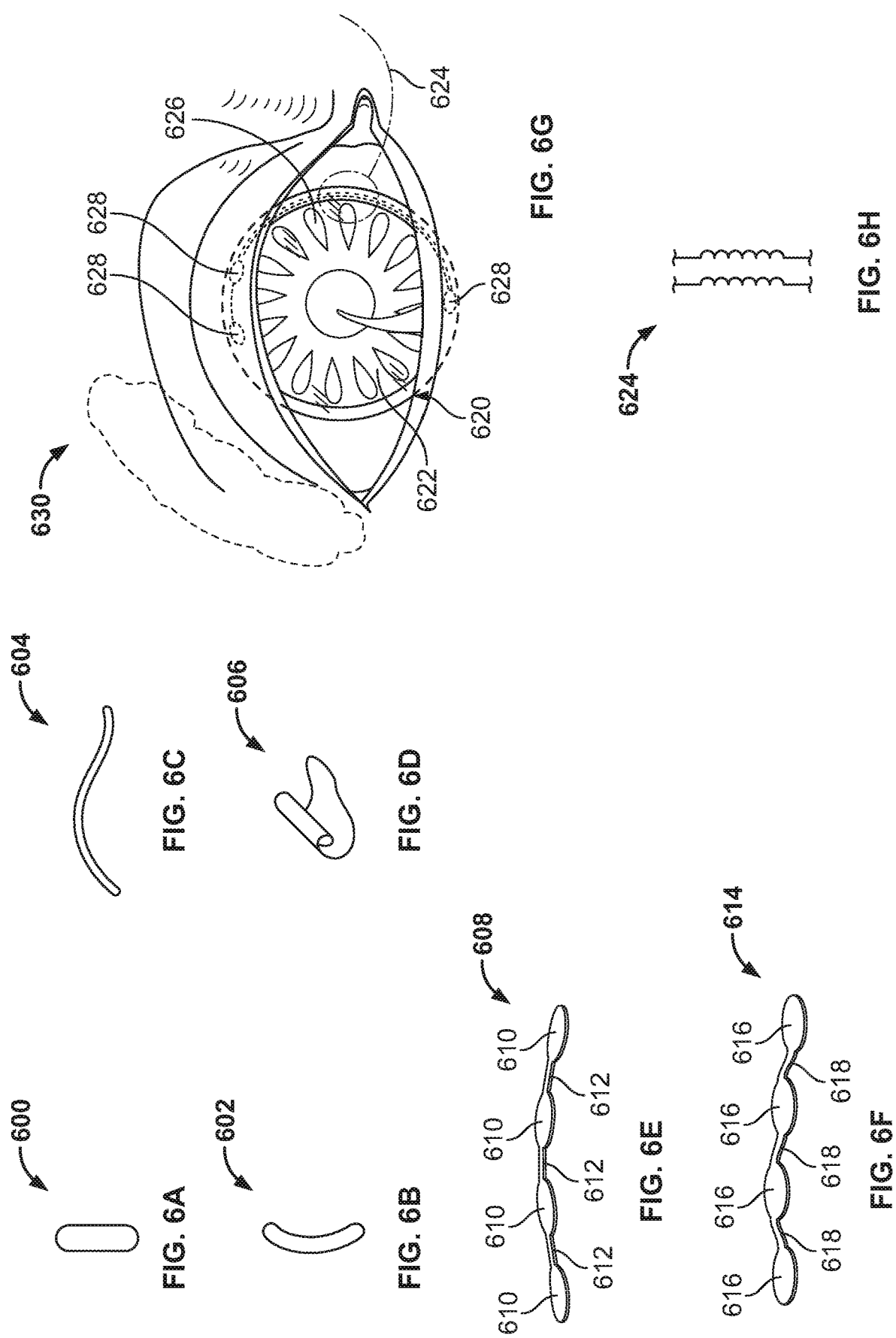

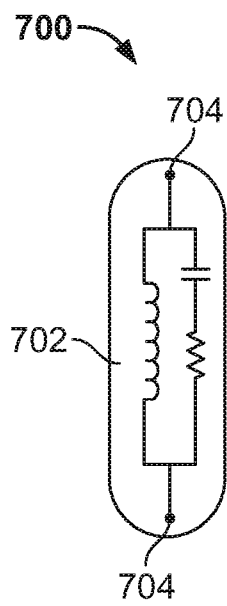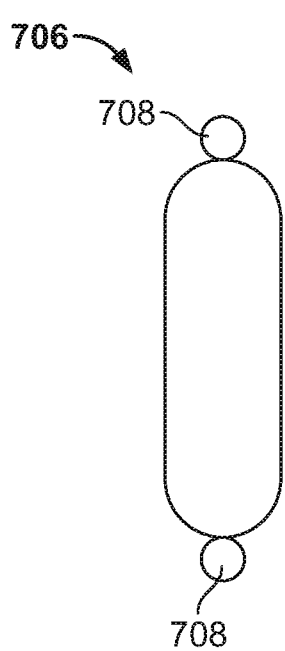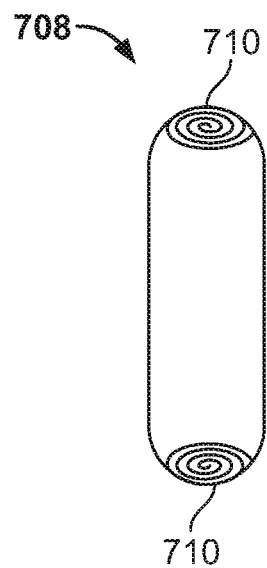
FIG. 7A   FIG. 7B   FIG. 7C
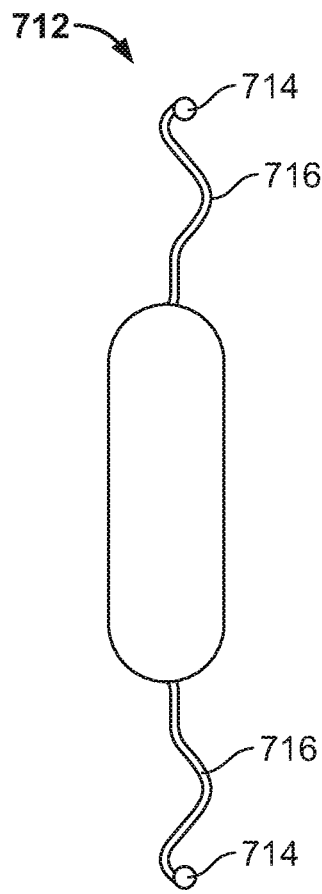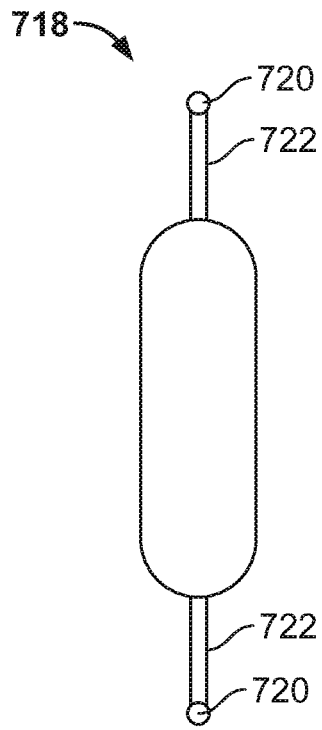
FIG. 7D   FIG. 7E

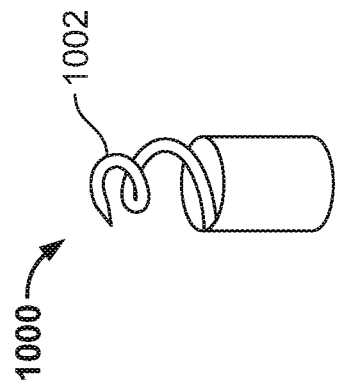
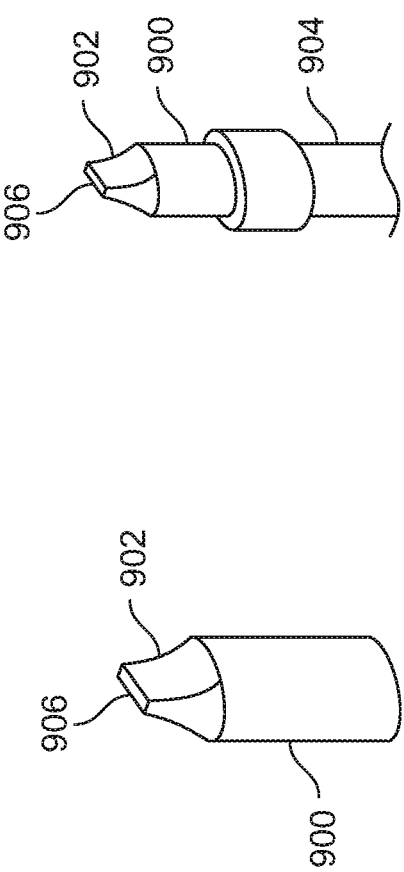
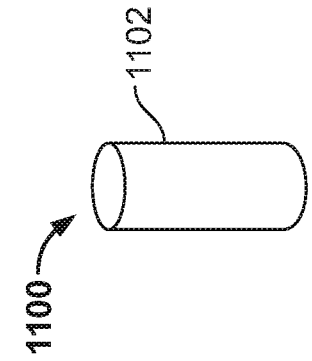
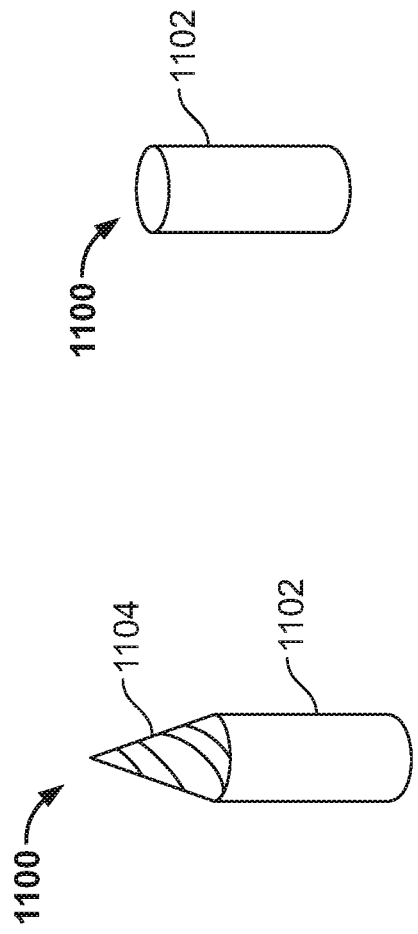

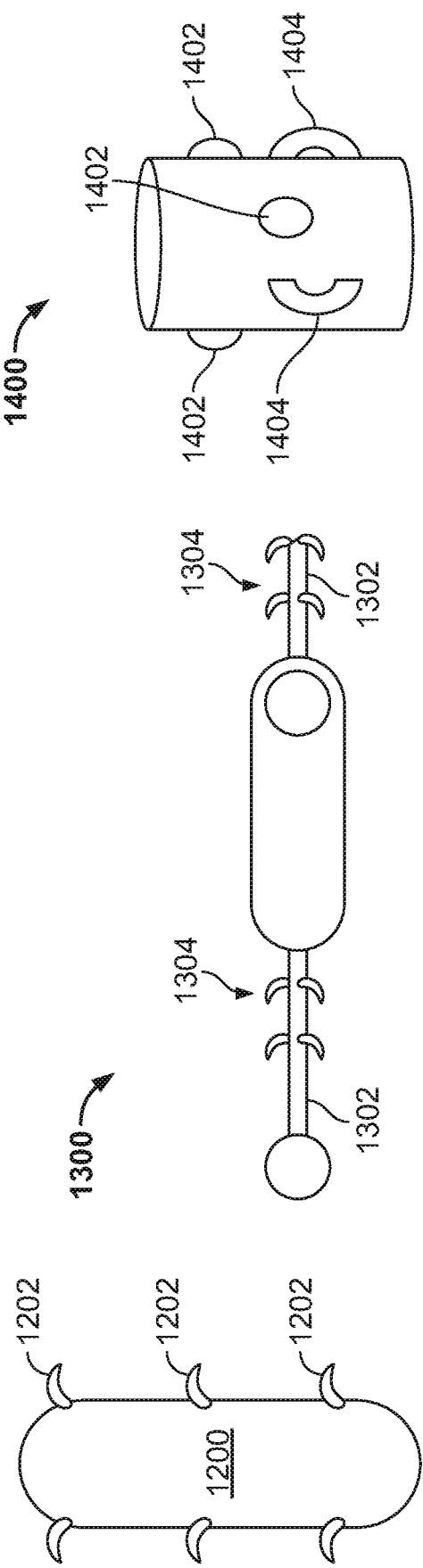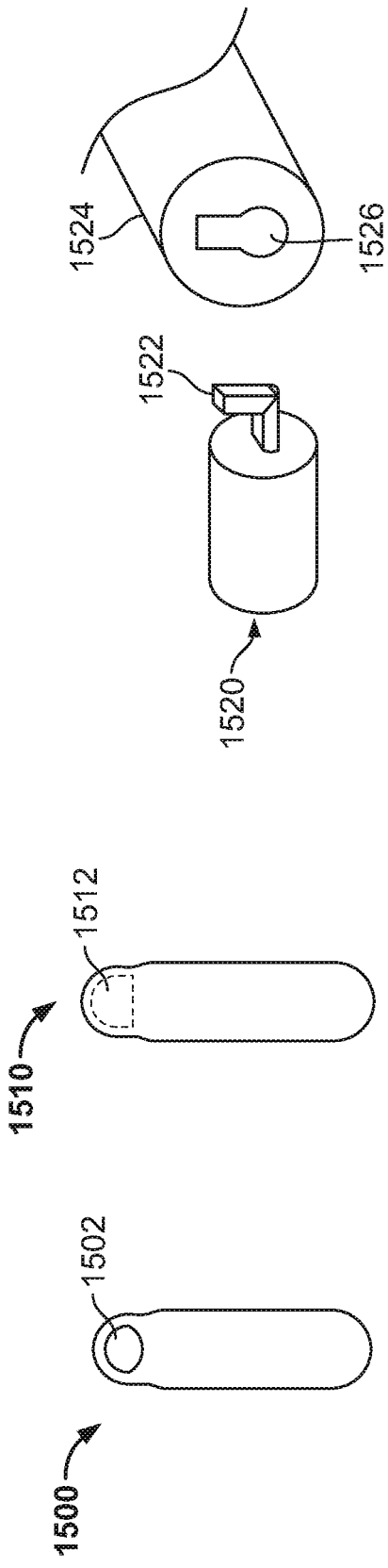

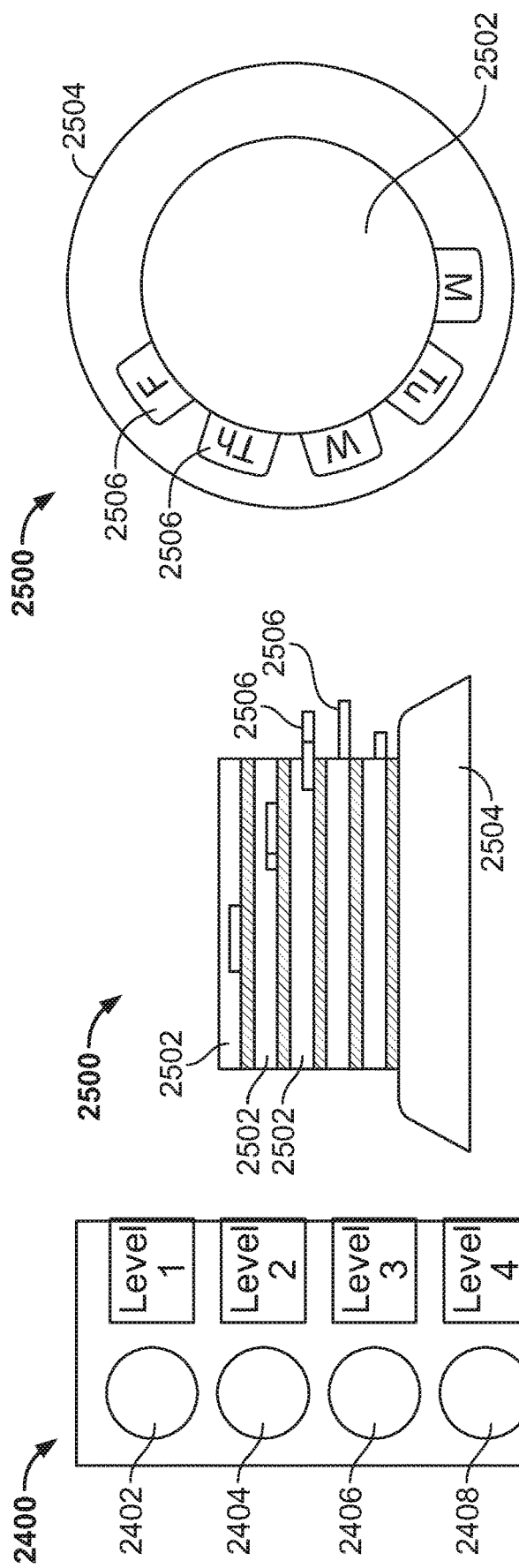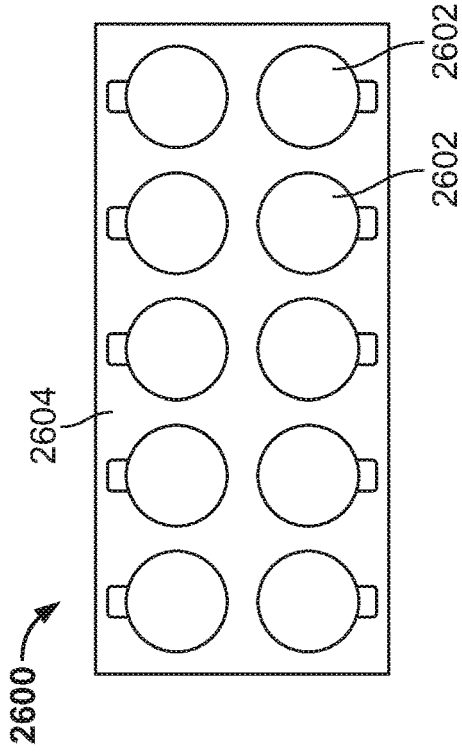

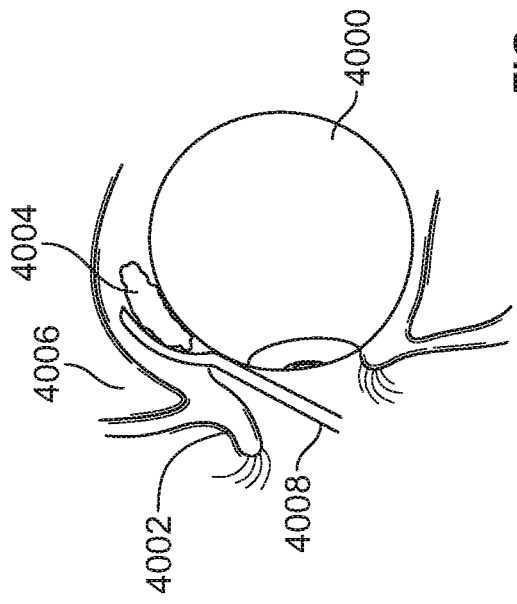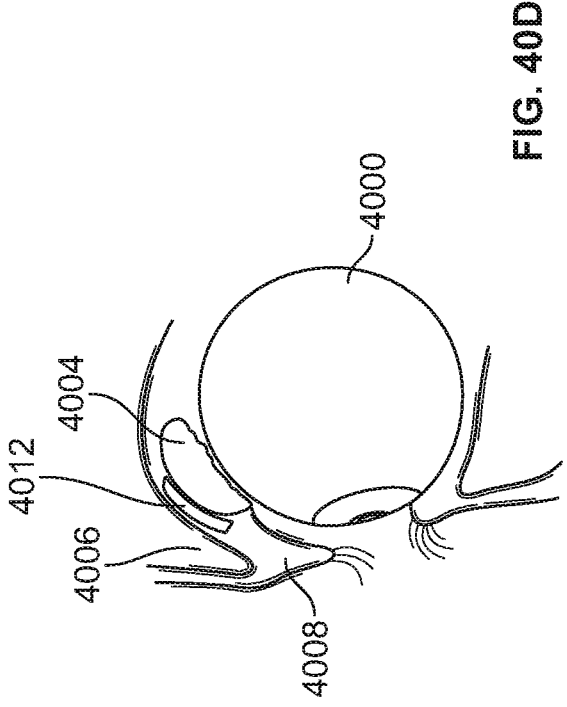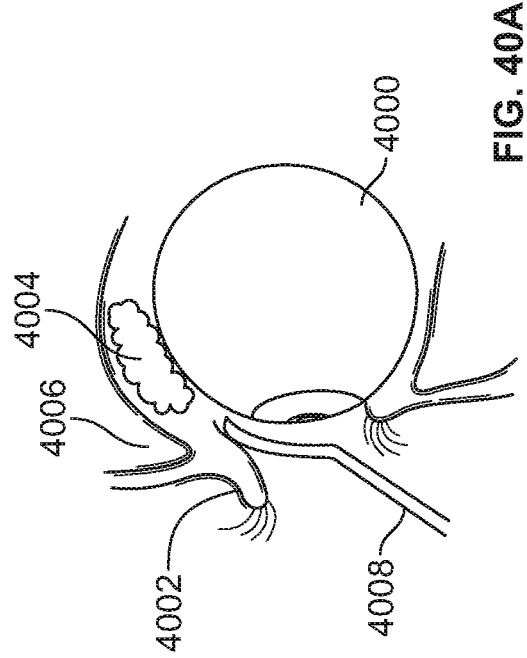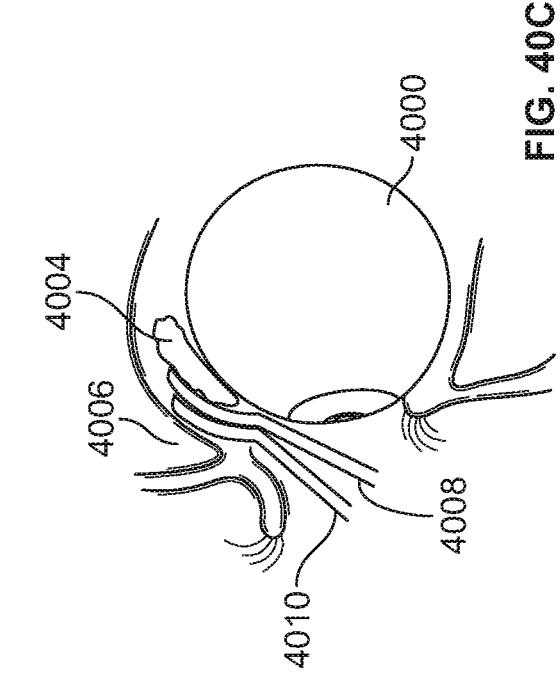
FIG. 40A
FIG. 40B
FIG. 40C
FIG. 40D

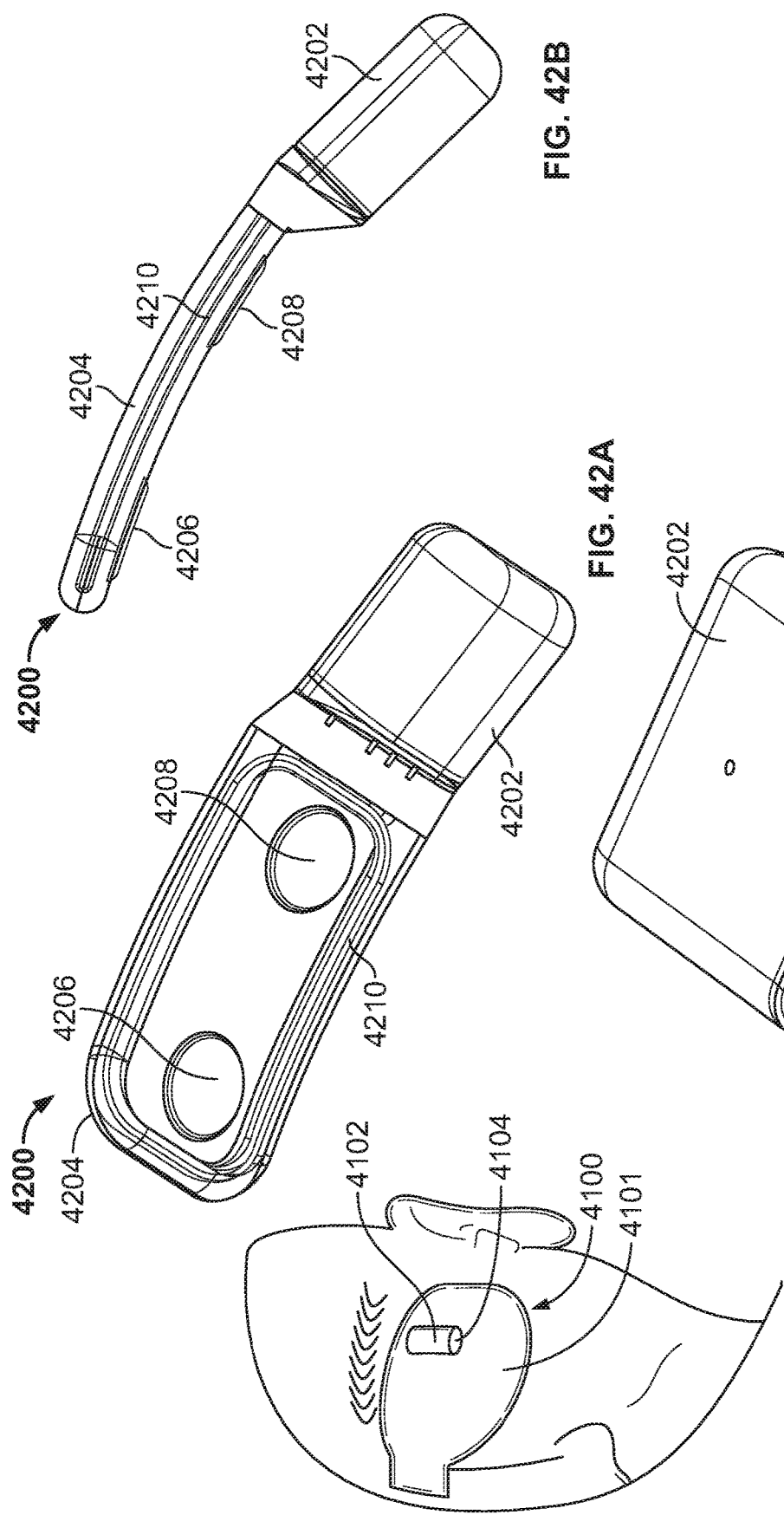

STIMULATION DEVICES AND METHODS

CROSS-REFERENCE TO RELATED APPLICATIONS

This application is a continuation of U.S. application Ser. No. 13/441,806, filed on Apr. 6, 2012, which is a continuation-in-part of U.S. application Ser. No. 13/298,042, filed on Nov. 16, 2011, issued as U.S. Pat. No. 8,918,181 on Dec. 23, 2014, which claims priority to U.S. Provisional Application Ser. No. 61/414,293, filed on Nov. 16, 2010, to U.S. Provisional Application Ser. No. 61/433,645, filed Jan. 18, 2011, to U.S. Provisional Application Ser. No. 61/433,649, filed Jan. 18, 2011, and to U.S. Provisional Application Ser. No. 61/433,652, filed on Jan. 18, 2011. U.S. application Ser. No. 13/441,806 also claims priority to U.S. Provisional Application Ser. No. 61/473,141, filed on Apr. 7, 2011, and to U.S. Provisional Application Ser. No. 61/523,732, filed on Aug. 15, 2011. Each of the foregoing applications is hereby incorporated by reference in its entirety.

FIELD

The present invention relates generally to stimulation systems and methods of use thereof. The stimulation systems may be used to stimulate one or more anatomical structures for the treatment of one or more indications, such as dry eye syndrome.

BACKGROUND

Dry eye syndrome is a debilitating disease that affects millions of patients worldwide and can cripple some patients. Millions of these individuals suffer from the most severe form. This disease often inflicts severe ocular discomfort, results in a dramatic shift in quality of life, induces poor ocular surface health, substantially reduces visual acuity and can threaten vision. Patients with severe dry eye develop a sensitivity to light and wind that prevents substantial time spent outdoors, and they often cannot read or drive because of the discomfort. Current treatment options provide little relief for those suffering from severe conditions. Current options include artificial tears, punctal plugs, humidity goggles, topical cyclosporine, and tarsorrhaphy. None of these treatments provides sufficient relief or treatment of the disease. What is needed is a system for restoring adequate tear production in patients having dry eye syndrome.

BRIEF SUMMARY

Described here are devices and methods for stimulating tissues. The stimulation systems may comprise a microstimulator and one or more controllers. In some variations, the microstimulator may comprise a passive stimulation circuit. In some variations, the microstimulator may comprise a housing and an extension connected to the housing and carrying at least one electrode. In some of these variations, the extension may be flexible. In some variations, the microstimulator may have a length of about 0.6 cm to about 2 cm, and a thickness of about 1 mm to about 2 mm, and a width of about 3 mm to about 8 mm. The microstimulator may be conformable and flexible and may have one or more fixation elements. The one or more fixation elements may include one or more hooks, barbs, and anchors. The microstimulator may have one or more coatings which may be adhesive and/or bioabsorbable. In some variations the microstimulator may comprise one or more coatings that are electrically conductive and/or electrically insulative The passive stimulation circuit may include a tank circuit and have one or more electrical safety features. The electrical safety features may include one or more current limiting rectifiers and one or more zener diodes. The electrical safety features may include a voltage limiting circuit to limit the voltage emitted by the stimulation component. The electrical safety feature may also include a current limiting element or circuit to limit the current emitted by the stimulation component and a charge output limiting element or circuit to limit the charge emitted by the stimulation component.

In some variations the passive stimulation circuit may comprise a ramping control unit. In some of these variations, the ramping control unit may comprise a charging unit and a field-effect transistor. The ramping control unit may control the amplitude of the stimulation signal generated by the stimulation circuit, and the stimulation circuit may be configured to produce a ramped stimulation signal. The passive stimulation circuit may comprise a signal conditioning unit. In some variations, the signal conditioning unit may comprise a rectifying unit. In some variations, the signal conditioning unit may comprise an amplitude limiting unit. In some variations, the signal condition unit may comprise a current source unit. The passive stimulation circuit may comprise a receiving unit and an output unit.

The passive stimulation circuit within a microstimulator may also include a variable resistive element, a variable capacitive element and one or more electrodes. The one or more electrodes of the passive stimulation circuit may be contact points, may be nestled within the microstimulator, may be coupled to a flexible lead, and may be coupled to a rigid lead. The one or more electrodes may contain platinum, iridium, platinum iridium, iridium oxide, titanium nitride, tantalum, or combinations thereof.

The microstimulator may be coupled to a controller and be hermetically sealed. The microstimulator may be injectable into a patient using a delivery system. The delivery system may comprise an insertion device (such as a 12 or larger gauge needle) and/or a dissection tool. The microstimulator may have one or more features to facilitate minimally invasive retrieval. The length and width of the microstimulator may be selected to permit placement of a portion of the microstimulator adjacent to the lacrimal gland. The length and width of the microstimulator may also be selected to permit placement of the entire microstimulator adjacent to the lacrimal gland and to permit placement of the microstimulator on, partially in, within or about the lacrimal gland.

In some variations, a method for treating dry eye by stimulating one or more nerves that innervate lacrimal gland tissue includes implanting a microstimulator adjacent to the lacrimal gland and applying stimulation to the lacrimal gland. The microstimulator may comprise a passive stimulation circuit comprising a ramping control unit. The microstimulator may be adjacent to the lacrimal gland and fully implanted within an orbit of a patient's eye. The microstimulator may be positioned such that it directly contacts the lacrimal gland. The microstimulator may be positioned such that it partially penetrates into the lacrimal gland. The microstimulator may be fully implanted into or completely within the lacrimal gland. The microstimulator may be fully or partially implanted within the orbit of the eye.

The stimulation provided by the microstimulator may selectively stimulate one or more nerves that innervate the lacrimal gland. The stimulation may selectively stimulate the one or more nerves that innervate the lacrimal gland without causing movement of the eye, without stimulating the ocular muscles, and without stimulating the superior rectus, lateral rectus, levator palpebrae superioris, retina or corresponding motor nerves. In some variations, the stimulation may selectively stimulate autonomic efferent fibers of the lacrimal gland. The autonomic efferent fibers may be selectively stimulated over the sensory afferent fibers or the A-delta pain fibers or over the C pain fibers. In some variations, the stimulation may selectively stimulate afferent fibers of the lacrimal gland, and may induce unilateral or bilatering tearing. In certain variations, the stimulation may stimulate only the one or more nerves that innervate the lacrimal gland. In some variations, the stimulation may selectively stimulate the acinar and/or ductal cells of the lacrimal gland. The stimulation may stimulate a combination of acinar cells, ductals cells, efferent fibers, and/or afferent fibers of the lacrimal gland.

When implanted, the microstimulator may conform to the fossa for the lacrimal gland after implantation. The microstimulator may conform to an exterior aspect of a lacrimal gland after implantation. Implanting a microstimulator may further include conforming the microstimulator to an exterior aspect of the lacrimal gland. After implantation, the microstimulator may conform to an exterior aspect of the fossa for the lacrimal gland.

The microstimulator may be implanted using an insertion device. In some variations, the insertion device is a 12 or larger gauge needle. In other variations, the insertion device comprises a cannula. In some variations, the insertion device may comprise a piston assembly, which in some variations may be spring-powered. The microstimulator may be loaded into the insertion device, and the insertion device may be inserted into an insertion pathway. In some variations, using an anatomical landmark at the corner of the eye, a needle may be positioned in proximity to the lacrimal gland, and the microstimulator may be deployed using the needle. Anatomical landmarks include, but are not limited to, the lateral canthis, an eyelid margin, a palpebral lobe of the lacrimal gland, the orbital rim, a bony protuberance on the superior-lateral aspect of the orbit, the vascular bed, or the like. In some variations, a microstimulator may be implanted by lifting the eyelid, forming an insertion pathway through the conjunctiva under the eyelid, and advancing the microstimulator into the insertion pathway. The insertion pathway may be formed using a dissection tool. In some variations, the insertion pathway may be formed using a dissection element of an insertion tool. In some variations, the insertion pathway may be formed between the periosteum and the orbital bone. In other variations, the insertion pathway may be formed between the periosteum and the lacrimal gland.

The stimulation may include a current having a pulse amplitude between about 250 µA to about 25 mA. The stimulation may include a pulse amplitude, a pulse width, and a pulse frequency, and one or more of the pulse amplitude, pulse width, or pulse frequency which may be varied over the treatment period. The stimulation may have a pulse frequency between about 2 Hz to about 270 Hz, between about 15 Hz to about 40 Hz, or between 30 Hz to about 60 Hz. The stimulation may include a current having a pulse width between about 50 µsec to about 2700 µsec. Stimulation having the above-mentioned parameters may be used to treat one or more conditions, such as dry eye. Stimulation pulses may be delivered continuously or intermittently, and may be delivered according to one or more patterns.

Implanting a microstimulator may further include identifying an insertion point for implantation based upon a feature of the orbit. The stimulation may be delivered in bursts and adjusted in response to a measured variable. The stimulation may include a current having a pulse width between about 50 µsec to about 2000 µsec. A controller may be positioned in proximity to the microstimulator and may generate a magnetic field. The magnetic field may be adjusted based on input from the user and/or based on the degree of coupling to the microstimulator. The magnetic field may be generated in bursts and coupled to the microstimulator to generate the stimulation. The magnetic field may have a frequency of about 10 kHz to about 100 MHz. The magnetic field may have a frequency of about 100 kHz to about 5 MHz. In some variations, the magnetic field may have a frequency between about 1 MHz and about 5 MHz.

In some variations, a system for treating dry eye may include a microstimulator configured for implantation into an orbit of an eye and a controller for generating a magnetic field to couple to the microstimulator. The controller may be housed within a hand-held device. The controller may comprise a patch which may be attached to a patient using one or more adhesive layers. The controller may be flexible and conformable, or may be partially flexible or comforable. The controller may be coupled to, or at least partially contained within, a flexible or conformable material. The microstimulator may have a length of about 0.6 cm to about 2 cm and a width of about 1 mm to about 8.5 mm and may include a passive stimulation circuit configured to receive the magnetic field generated by the controller. The controller may be flexible, conformable, and capable of detecting one or more operating parameters of the microstimulator. At least part of the controller may be disposable and rechargeable. The controller may be coupled to, or at least partially contained within, an eyeglass frame, a wrist watch, or other object. In some variations, the controller may be configured to attach to an eyeglass frame using one or more adhesive layers and/or mechanical coupling elements.

In some variations, a method for treating dry eye by stimulating one or more nerves that innervate lacrimal gland tissue may include positioning one or more stimulation electrodes adjacent to the lacrimal gland and applying stimulation to the lacrimal gland. A microstimulator may be adjacent the lacrimal gland fully implanted within an orbit of a patient's eye. The microstimulator may be adjacent to and directly contacting the lacrimal gland, adjacent to and at least partially penetrating into the lacrimal gland, and adjacent to and fully implanted into or completely within the lacrimal gland. Adjacent to the lacrimal gland may be about, within or partially in the lacrimal gland. The microstimulator may be fully implanted within the orbit of the eye. The one or more electrodes are electrically coupled to a pulse generator, which may be implantable. The pulse generator may be implantable in proximity to the one or more stimulation electrodes. The pulse generator may be implantable in proximity to the temporal bone, a subclavicular pocket, or a subcutaneous abdominal pocket. The method may further include positioning a controller in proximity to the pulse generator.

In some variations, a microstimulator may include a coil, a housing, and a pair of electrodes. The coil may be formed from a wire having a length turned into a plurality of windings and responsive to an induced field to produce an output signal. The microstimulator may be electrically coupled to receive the output from the coil and produce a signal responsive to the output. The housing may encompass the circuit and the coil, and may be adapted and configured for placement within an orbit and adjacent an eye within the orbit. The pair of electrodes may extend from the housing and be configured to receive the signal. In some variations, the electrodes may be integrated into the housing. The electrodes may have the same shape or may have different shapes. In some variations, one electrode may have a larger surface area, which may reduce the current density at that electrode. The electrodes may be spaced apart (e.g., by about 6 mm to about 15 mm), which may increase current flow through surrounding tissue. When positioned near the lacrimal gland, one or more of the electrodes may be placed in direct or indirect contact with the lacrimal gland.

The pair of electrodes and the housing may be shaped for injection through the lumen of an insertion device. The housing may be configured for placement adjacent to a lacrimal gland, within an orbit to permit selective stimulation of a lacrimal gland with the signal, and within a fossa near the lacrimal gland to position the pair of electrodes on, in or about a lacrimal gland.

The housing may be configured for placement in proximity to a lacrimal gland without being in proximity to a muscle of the eye. The housing may have a curvature conforming at least partially to the curvature of a fossa for the lacrimal gland, or a curvature conforming at least partially to an exterior aspect of a lacrimal gland.

The microstimulator may further include a second coil, a second rectifying and tuning circuit. The second coil may be within the housing and oriented nearly orthogonal to the second coil. The second rectifying and capacitive circuit may be within the housing and coupled to the second coil, such that the second rectifying and capacitive circuit is configured to produce a second signal. The selector switch may be within the housing and connected to receive the first signal and the second signal and supply one of the first signal and the second signal to the pair of electrodes. The selector switch may determine which one of the first signal and the second signal to send to the electrodes based on a comparison of the first signal and the second signal.

Current from the two signals may be summed without the use of a selector switch. The signal from the coil may have a frequency corresponding to the induced field, which may be generated from an external coil through mutual inductance. The induced field may be generated by an external controller.

The signal generated in the coil may have a frequency about equal to the frequency of the induced field generated by the external controller. The induced field generated by the external controller may have a frequency based on user input. The external controller may be contained within a hand-held device and may be disposable. The external controller may be contained within one of an adhesive patch, a pair of eye glasses, and a head set. The circuit may include a diode to rectify a current signal and a capacitor for storing charge and/or filtering the rectified signal. The circuit may include a rectifying circuit that may include a diode and a resistor connected in parallel. The signal may have a voltage with an amplitude of between 0.1V and 25V, a current with an amplitude between 10 µA and 25 mA, and a pulsed current with a frequency of 2 Hz to 1000 Hz. The pair of electrodes may be connected to leads, which may include tines.

In some variations, a method of implanting a microstimulator adjacent to the eye may include inserting an access device percutaneously into an orbit of an eye. A microstimulator may be advanced through the access device into a position in proximity to the superior lateral aspect of the orbit. A stimulation signal may be applied to a portion of the eye with the microstimulator. Before the inserting step, an insertion point may be inserted for the access device based on the insertion point's relation to a feature on the orbit. After the advancing, the microstimulator may be positioned within a fossa of the lacrimal gland, and at least one electrode of the microstimulator may be positioned on, in or adjacent to a lacrimal gland, and an electrode of the microstimulator is positioned on, in or adjacent a lacrimal gland.

Tear production may be increased in the eye. Vasodilation of the lacrimal gland may occur unilaterally or bilaterally. After advancing, an electrode of the microstimulator may be positioned on, in or adjacent to a neural structure associated with a lacrimal gland. During the applying, the signal only stimulates a lacrimal gland, the signal may selectively stimulate a lacrimal gland over a muscle of the eye, or the signal is selected to stimulate a lacrimal gland without stimulating a muscle fiber of the eye. After the advancing, an electrode of the microstimulator is positioned adjacent to a neural structure associated with a lacrimal gland and spaced apart from a muscle of the eye. The muscle of the eye may be a rectus muscle or an oblique muscle or a levator palpebrae muscle. The microstimulator may be adjacent a lacrimal gland and spaced apart from a superior rectus muscle or a lateral rectus muscle or a levator palpebrae muscle. The signal may stimulate a lacrimal gland without activating a rectus muscle or an oblique muscle or a levator muscle in proximity to the lacrimal gland.

In some variations, a method for using a microstimulator may include receiving a microstimulator at the orbit of a patient's eye. A magnetic field may be received by the microstimulator from an external power source such as a controller. A current may be generated by the microstimulator from the magnetic field. The current may be applied to the patient to produce tears in the patient's eye or vasodilation of the lacrimal gland.

In some variations, a method for using a microstimulator may include implanting a stimulation device within a patient's orbit. A controller with a power source may be placed external to the patient's skin and in communication with the microstimulator. A magnetic field may be applied to the microstimulator from the controller. A current may be generated in the microstimulator from the magnetic field. The current may be applied to produce tears in the patient's eye, cause vasodilation in the lacrimal gland, release lacrimal proteins into a patient's tear film, and/or cause lacrimation of the contralateral lacrimal gland.

In some variations, a system for treating a patient with dry eye syndrome may include a microstimulator and a controller. The microstimulator may be responsive to a magnetic field and placed within an orbit of a patient's eye. The microstimulator may be configured to generate a current based on the magnetic field and apply the current to a patient to produce tears in the patient's eye. The controller may be configured to generate the magnetic field and be placed at a location near the microstimulator.

In some variations, a method for treating a patient with dry eye syndrome may begin with insert a microstimulator within an orbit of a patient's eye using a positioning device. A controller, which may include a power source, may be placed external to a patient's skin and in proximity to the microstimulator. A magnetic field may be applied to the microstimulator by the controller. A current may be generated by the microstimulator from the magnetic field. The current may then be applied to a patient to produce tears in the patient's eye. In some variations, a method for using a microstimulator may begin with connecting a microstimulator to a multi-electrode lead positioned on, in or adjacent a lacrimal gland. One or more electrodes may be selected from the multi-electrode lead to activate tear production in a patient's eye.

BRIEF DESCRIPTION OF THE DRAWINGS

FIGS. 6A-6H depict exemplary microstimulators suitable for use with the stimulation systems described here.

FIGS. 7A-7F depict illustrative microstimulators having different electrode configurations.

FIGS. 9A, 9B, 10, 11A and 11B depict variations of microstimulators suitable for use with the stimulation systems described here.

FIGS. 12, 13, and 14 depict variations of microstimulators having fixation elements.

FIGS. 15A-15C depict variations of microstimulators comprising retrieval features.

FIGS. 24, 25A, 25B, and 26 depict illustrative variations of controller sets suitable for use with the stimulation systems described here.

FIGS. 40A-40D depict a method of delivering a microstimulator to the ocular cavity.

FIG. 41 depicts a variation of a guiding element suitable for use with the delivery systems described here.

FIGS. 42A-42C depict a perspective view, a side view, and a partial view, respectively, of a variation of a microstimulator suitable for use with the stimulation systems described here.

DETAILED DESCRIPTION

Described here are stimulation systems for stimulating anatomical targets in a patient for the treatment of one or more conditions. The stimulation systems may include at least one controller and at least one microstimulator. The controller may be implemented as a part of the microstimulator, or as a separate device. When formed as a separate device, the controller may communicate with the microstimulator via a wireless and/or wired connection. The controller may produce a waveform signal which may convey power and/or information to the microstimulator and the microstimulator may deliver one or more stimulation signals to an anatomical target based on the waveform signal.

The stimulation systems may be used to stimulate any suitable anatomical target or targets to treat a number of conditions. In some variations, the stimulation systems described here may be used to treat dry eye. For example, the stimulation systems may be used to stimulate one or more nerves, tissues, glands, or other structures involved in the process of lacrimation or glandular vasodilation. For example, the systems may stimulate one or more of a lacrimal gland, one or more meibomian glands, lacrimal ducts, parasympathetic nerves, fibers and neurites, sympathetic nerves, fibers and neurites, rami lacrimales, lacrimal nerve, perivascular nerves of lacrimal artery and branches thereof, nerve fibers innervating the meibomian glands, myoepithelial cells of the lacrimal gland, acinar cells of the lacrimal gland, ductal cells of the lacrimal gland. Methods of treating dry eye and other conditions are described in more detail below. Also described here are delivery systems and methods for delivering or otherwise implanting one or more microstimulators and/or controllers into a patient.

Stimulation Systems

Figure 1A:
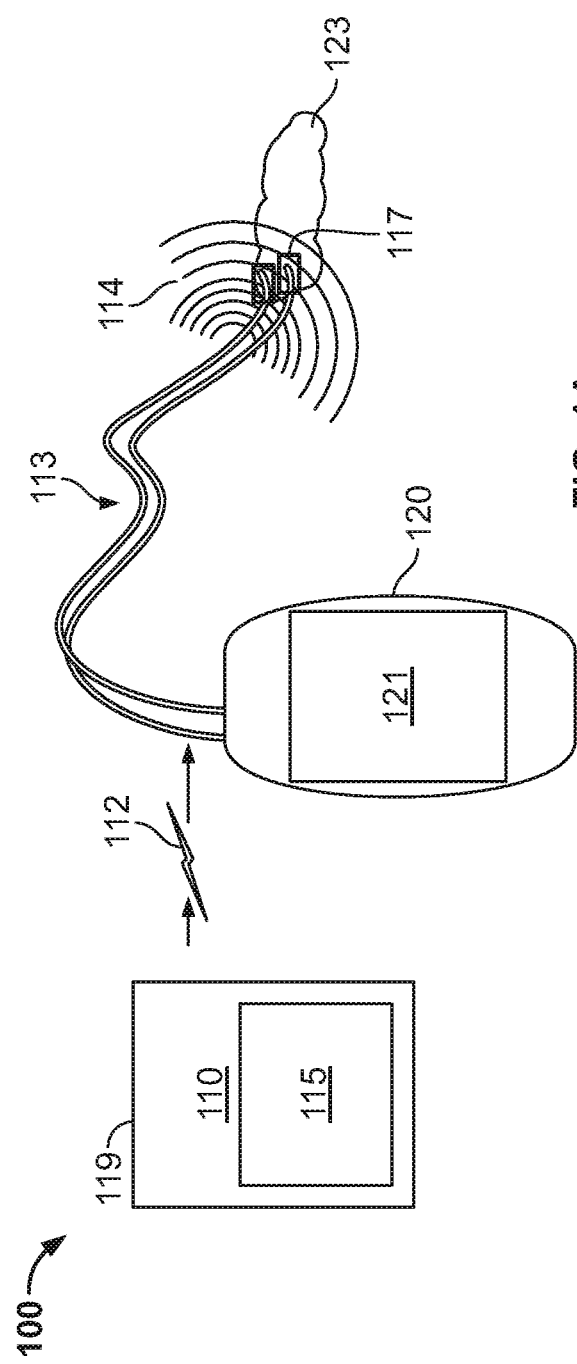
FIGS. 1A and 1B depict block diagrams of two variations of the stimulation systems described here.
Figure 1B:
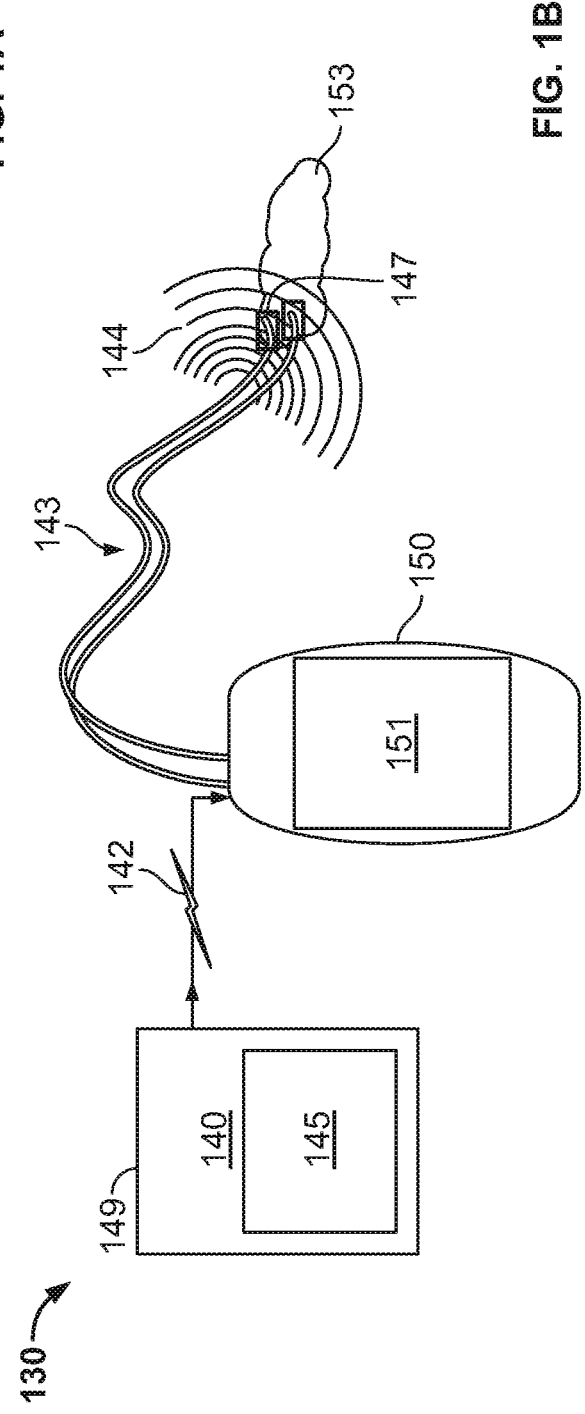

FIGS. 1A and 1B show block diagrams of two variations of the stimulation systems described here. FIG. 1A depicts a wireless stimulation system (100) including a controller (110) and a microstimulator (120). As shown there, the controller (110) may include a housing (119) and may contain a controller circuit (115). The controller circuit (115) may generate and transmit an output signal (112), which may be received wirelessly by the microstimulator (120). The transmitted signal may include one or more magnetic fields, electronic signals, radiofrequency signals, optical signals, ultrasound signals, or the like. The output signal (112) may provide power and/or information to the microstimulator (120) as will be described in more detail below. The controller may be implanted within the patient, or may remain external patient, as will be described in more detail below. The controller circuit (115) may be any suitable circuit, such as one or more of the controller circuits described in more detail below.

As shown in FIG. 1A, the microstimulator (120) may include one or more electrodes (117), one or more leads (113), and a stimulation circuit (121). While the electrodes (117) are shown in FIG. 1A as being connected to the stimulation circuit (121) via leads (113), it should be appreciated that the microstimulator (120) need not include leads. The microstimulator (120) may be implanted within a patient and positioned with respect to the controller (110) whereby the microstimulator (120) may receive the output signal (112) generated by the controller (110). The stimulation circuit (121) may receive the output signal (112), and may generate a stimulation signal (114) based on the received output signal (112). For example, in some variations the microstimulator (120) may comprise a passive stimulation circuit that is configured to process the output signal (112) and deliver the processed signal as a stimulation signal (114) to tissue without using any internal logic or intelligence within the microstimulator (120). In some variations, the microstimulator (120) may use internal logic or intelligence in processing the received output signal (112). The resulting stimulation signal (114) may be a direct current or alternating current signal, and may be applied to an anatomical target (123), such as for example a lacrimal gland, via one or more of the electrodes (117). The stimulation signal (114) may be charge-balanced. The microstimulator may be configured in any suitable manner, as will be described in more detail below.

When the stimulation signal (114) is delivered to an anatomical target (123), the stimulation may result in a desired physiological effect (such as, for example, generating tears in a patient). Stimulation of an anatomical target (123) may produce any suitable endocrinological or other physiological outcome, including, but not limited to, secretion of fluid, electrolytes, and proteins, vasodilatation, increasing the volume of tears, increasing the quality of tears, improving surface health, decreasing tear osmolarity, and decreasing ocular inflammation.

FIG. 1B shows a block diagram of a variation of a wired stimulation system (130). The wired stimulation system (130) may include a controller (140) and a microstimulator (150). The controller (140) may include a housing (149) and a controller circuit (145), and may be configured to transmit an output signal (142) to the microstimulator (150) via a wired transmission line (148), such as a conducting wire or other medium. The wired transmission line (148) may be attached to the controller (140) and be routed through a patient's body to the microstimulator (150). The microstimulator (150) may be implanted within a patient and positioned with respect to the controller (140) such that the microstimulator (150) may receive the output signal (142) from the controller (140). The stimulation circuit (151) may receive the output signal (142), and may generate a stimulation signal (144) based on the received output signal (142). The stimulation signal (144) may be applied to an anatomical target (153), such as for example a lacrimal gland, via one or more of the electrodes (147) and, in some instances, one or more leads (143). Stimulation of the anatomical target (153) may result in one or more physiological or other endocrinological outcomes (159), such as those described immediately above.

When the stimulation systems comprises a transmission line between a controller and microstimulator, or a lead connecting one or more electrodes to a microstimulator, the transmission line and/or leads may be tunneled. The tunneling pathway may depend on where the microstimulator, controller, and/or electrodes are implanted. For example, a tunneling pathway may extend from the ear region (superficial to the temporal bone) to the temporal aspect of the orbit into the superior lateral aspect of the orbit, through the orbital septum and to the anatomical target.

Microstimulators

As mentioned above, the stimulation systems described here comprise one or more microstimulators. The microstimulator may be any device suitable for delivering stimulation to tissue. In some variations, the microstimulator may comprise one or more passive stimulation circuits in which the device does not include any internal logic or intelligence (e.g., ASICs, microcontrollers or the like). In some of these variations, the microstimulator does not have an internal battery. In these variations, the microstimulator may include only a dissipation circuit that receives an output signal from a controller, generates a current based on the received signal, and delivers the generated current. The dissipation circuit may contain one or more signal conditioning units which may shape or otherwise modify the signal received from a controller. In some variations, the circuit may be configured to receive energy from an external source, rectify the energy into a stimulation pulse, and allow for passive charge balancing. In some variations the stimulation circuit may comprise one or more current rectifiers, one or more amplitude limiting units, and one or more ramping control units, combinations, thereof, or the like. In some variations, the dissipation circuit may comprise one or more adjustable/tunable components.

In other variations, a microstimulator may include internal logic which may be used to shape or modify a signal received from a controller. In some of these variations, the microstimulator may not include an internal battery, such that operating power is received by the output signal of a controller. In still other variations, the microstimulator may comprise an implantable pulse generator, which may include all of the circuitry necessary to generate and deliver electrical pulses to tissue. The stimulation circuits described here may contain elements which allow a controller to detect one or more operating parameters of the stimulation circuit.

Figure 2:
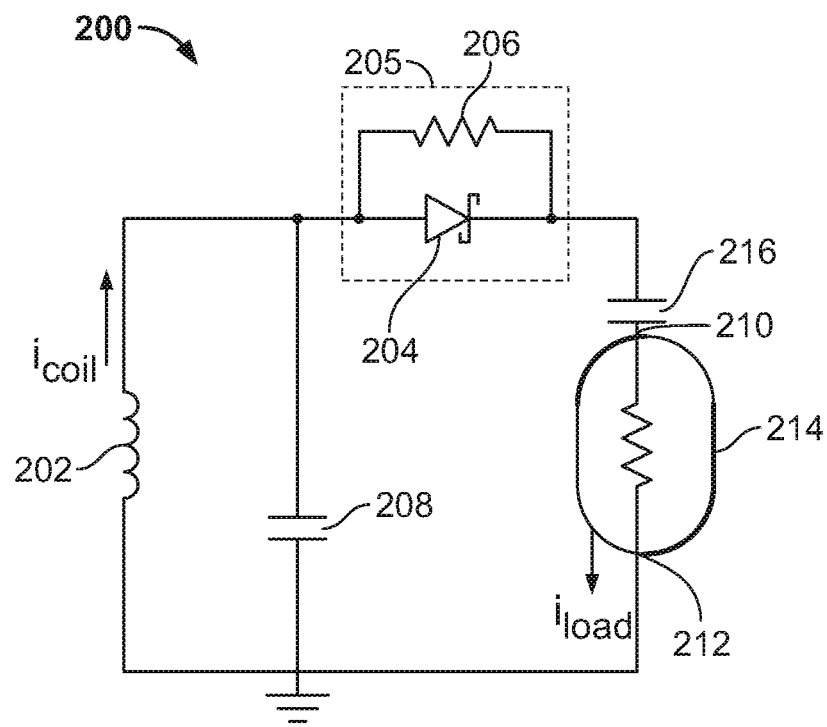
FIG. 2 depicts an illustrative variation of a passive stimulation circuit that may be used with the stimulation devices described here.

FIG. 2 depicts one variation of a passive stimulation circuit (200) which may be used with the stimulation devices described here. As shown there, the stimulation circuit (200) may include a microstimulator coil (202) (e.g., a conductive coil), a rectifying circuit (205) including a diode (204) and a resistor (206), a tuning capacitor (208), and a coupling capacitor (216). As shown there, one end of the microstimulator coil (202) may be connected to a first end of tuning capacitor (208), and a first end of the rectifying circuit (205). The resistor (206) and diode (204) may be connected in parallel, with a first end of the rectifying circuit (205) connected to the tuning capacitor (208) and the microstimulator coil (202) and the second end of the rectifying circuit (205) connected to the coupling capacitor (216). The coupling capacitor (216) may be connected to a first electrode (210). It should be appreciated that the rectifying circuit (205) may comprise a half-wave rectifier, a full-wave rectifier, or the like. The second end of microstimulator coil (202) may be connected to the other end of the tuning capacitor (208) and a second electrode (212).

In operation, a magnetic field generated by a controller (not shown) may be applied to microstimulator coil (202). The microstimulator coil (202) may generate a current $i_{coil}$ as a result of the applied magnetic field (e.g., via inductive coupling). The tuning capacitor (208) may form a tuning circuit with the microstimulator coil (202) such that the microstimulator coil (202) only receives magnetic fields generated using a specific frequency or range of frequencies. The current may pass through the rectifying circuit of resistor (208) and diode (204) and deliver a current $i_{load}$ between first (210) and second (212) electrodes. The current $i_{load}$ may pass through tissue (214) (represented in FIG. 2 as a resistor). The coupling capacitor (216) may provide AC-coupling and charge-balancing for the stimulation applied to the tissue (214). The coupling capacitor (216) may charge when an active stimulation pulse is passed through the rectifying circuit (205), and may discharge through the resistor (208) of the rectifying circuit during an inactive phase following the delivery of the active stimulation pulse.

Because the passive stimulation circuit is configured to condition and deliver the output signal received from a controller, one or more characteristics of the stimulation signal delivered by a microstimulator may be at least partially dependent on one or more characteristics of the stimulation signal. The controller may adjust one or more characteristics of the output signal (e.g., the amplitude, burst width, burst frequency, etc.) to alter the one or more characteristics (e.g., amplitude, pulse width, pulse frequency, etc.) of the stimulation signal produced by the microstimulator. For example, the amplitude of a signal applied generated by a microstimulator may be adjusted by modifying the amplitude of an alternating magnetic field produced by a controller coil.

While the stimulation circuit (200) is shown in FIG. 2 as comprising a coil (202), it should be appreciated that the stimulation circuits described here may receive energy in any suitable manner. For example, in some variations the stimulation may be configured to receive magnetic energy. In these variations, the microstimulator may comprise one or more coils (such as shown in FIG. 2) and/or magneto-electrical elements which may be formed from a material that generates a current when a magnetic field is applied thereto. The magneto-electrical elements may be formed from one or more materials such as $Cr_2O_3$, one or more mutiferroic materials, combinations thereof and the like. Magneto-electrical elements may allow for current generation with a smaller volume or device footprint than may be required for a coil. The magneto-electrical elements may further be shaped such that it may be capable of generating a current when positioned in multiple orientations relative to a magnetic field.

In some variations, the stimulation circuit may be configured to receive ultrasound energy. For example, in some variations the microstimulator may comprise one or more ultrasound transducers which may generate current in response to a transmitted ultrasound signal. In some variations, the ultrasound signal may be focused on the microstimulator using one or more ultrasound transmitters. In other variations, the microstimulator may be configured to receive optical energy (e.g., infrared, ultraviolet, visible wavelengths, or the like) and generate a current in response thereto. For example, in some variations a stimulation circuit may comprise one or more photo-voltaic elements that generate a current in response to received optical energy. In other variations, the microstimulator may be configured to receive far-field RF energy. For example, high-frequency RF energy may be received by the microstimulator using an antenna, and may allow for tolerate for a variety of microstimulator orientations. It should be appreciated that in some variations, the microstimulators described here may be capable of receiving energy from a plurality of sources, such as a combination of magnetic, ultrasound, optical, and/or RF signals.

Figure 3A:
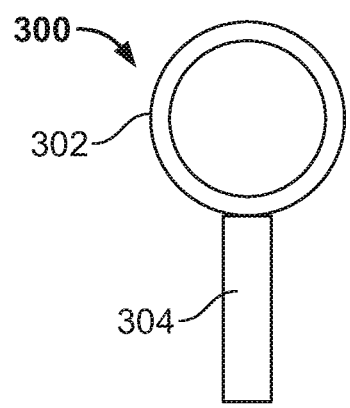
FIGS. 3A-3F depict illustrative variations of coil arrangements suitable for use with the microstimulators described here.
Figure 3B:
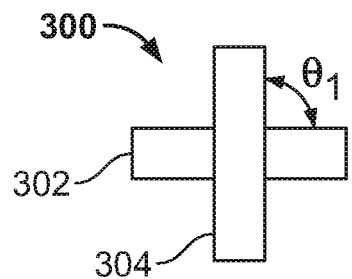

In variations where a stimulation circuit is configured to generate a current using inductive coupling, the stimulation circuit may be configured to improve tolerance to angular misalignment between internal and external components. In some of these variations, a microstimulator may include two or more coils positioned in non-parallel orientations. FIGS. 3A-3F illustrate three variations of coil arrangements having multiple coils. For example, FIGS. 3A and 3B show a side view and a top view, respectively, of a coil arrangement (300) comprising a first coil (302) and a second coil (304). As shown there, the first coil (302) may be positioned in a plane that is at an angle ($\theta_1$) relative to a plane of the second coil (304). The angle ($\theta_1$) between the planes of the first and second coils is shown in FIGS. 3A and 3B as being approximately 90 degrees, but it should be appreciated that this angle may be any suitable angle (e.g., about 45 degrees, about 60 degrees, etc.). By positioning the coils in different planes, the coil arrangement may still be able to generate a current even if one of the coils is positioned perpendicularly to an external coil.

Figure 3C:
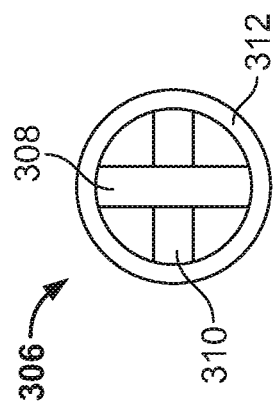
Figure 3D:
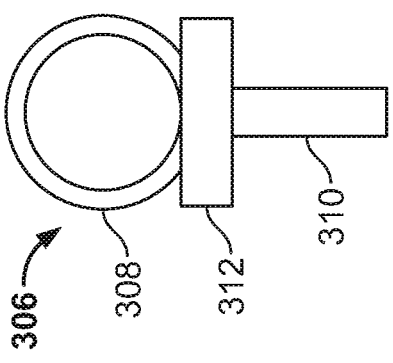
Figure 3F:
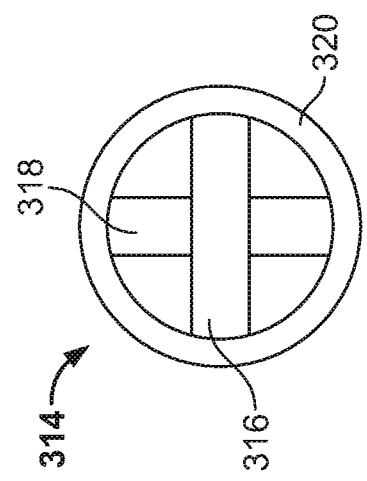
Figure 3E:
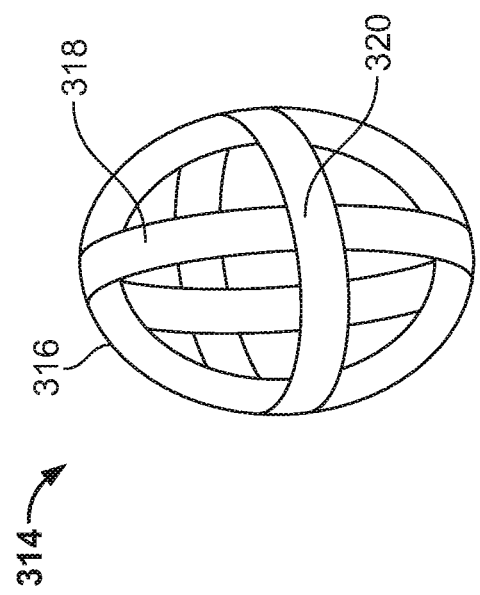

FIGS. 3C and 3D illustrate a side view and a top view, respectively, of another variation of a coil arrangement (306) having a first coil (308), a second coil (310), and a third coil (312). The planes of each of the first (308), second (310), and third (312) coils may be angled relative to other coils. For example, in the variation shown in FIGS. 3C and 3D, the plane of the first coil (308) may be perpendicular to the plane of the second coil (310), and the plane of the third coil (312) may be perpendicular to the planes of both the first (308) and second coils (310). It should be appreciated that the angle between any of the two coils may be any suitable angle. FIGS. 3E and 3F depict a perspective view and a side view, respectively, of another variation of a coil arrangement (314) having a first coil (316), a second coil (318), and a third coil (320). The planes of each of the first (316), second (318), and third (320) coils may be angled relative to the other coils, as described immediately above. Additionally, to help reduce the overall profile of the coil arrangement (314), the first coil (316) may be positioned within the second coil (318), and the first (316) and second (318) coils may be positioned within the third coil (320). In instances where a stimulation circuit comprises a coil arrangement comprising a plurality of coils, the stimulation circuit may comprise a plurality of tuning circuits, and the currents produced by the plurality of coils may be summed using rectifiers.

While the passive stimulation circuit (200) described above with respect to FIG. 2 as being configured to deliver electrical stimulation to a patient, it should be appreciated that the microstimulators described here may be configured to apply any suitable stimulation to a patient. In some variations, a microstimulator may be configured to deliver one or more optical signals, acoustic signals, or the like to a patient.

The stimulation circuits described here may comprise one or more electrical safety features. The electrical safety features may limit one or more parameters of the signals received or generated by the microstimulator, which may prevent a potentially harmful stimulation circuit from being supplied to a patient. Electrical safety features may include one or more elements such as a capacitor in series with the electrodes to limit charge delivery, one or more elements such as a capacitor in series with the electrodes to ensure DC charge-balanced stimulation, one or more resistors in parallel with the electrodes and/or series capacitor to allow for DC charge-balanced stimulation by capacitive discharge, one or more current-limiting diodes in series with the electrodes to limit maximum stimulation current amplitude, one or more zener diodes to limit maximum output voltage, combinations thereof or the like. The resistor in parallel with the electrodes may be of a larger impedance than the tissue load impedance to ensure power efficient stimulation.

Figure 4:
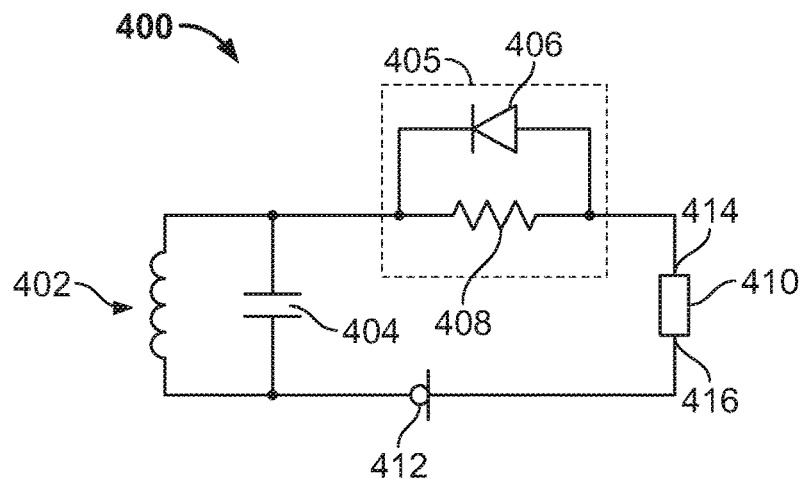
FIGS. 4, 5A and 5B depict variations of passive stimulation circuits suitable for use with the microstimulators described here.

FIG. 4 shows one variation of a stimulation circuit (400) comprising a current-limiting device. As shown there, stimulation circuit (400) may comprise a coil (402), a tuning capacitor (404), and a rectifying circuit (405) consisting of a diode (406) and a resistor (408), and first (414) and second (416) electrodes. These elements may be the same as the components of stimulation circuit (200) and may be positioned as described above in relation to FIG. 2. Additionally shown in FIG. 4 is a current-limiting diode (412), where the current-limiting diode (412) separates the second electrode (416) from the coil (402) and tuning capacitor (404). Current limiting diode (412) may limit the current that passes through the diode (412), which may also limit the current that is passed through a tissue load (410) between first (414) and second (416) electrodes. For example, when a pulse is delivered through the tissue load (410), as will be described in more detail below, a recharge current that provides charge balancing may initially have an amplitude that causes discomfort or stimulation of unintended tissues. A current-limiting device (or one or of the electrical safety features described above, such as a high-impedance recharge circuit or a zener diode or voltage limiting element in parallel with the tissue load) may limit the magnitude of the recharge current, and may thereby prevent unintended tissue stimulation or discomfort/pain.

In some variations, the stimulation circuits described here comprises one or more adjustable elements. For example, the stimulation circuit may comprise one or more variable resistance elements, variable capacitive elements, variable inductance elements, variable non-linear elements, or the like. The variable resistive elements, capacitive elements, inductive elements, or nonlinear elements may be used to alter a characteristic of the stimulation circuit, such as the resonant frequency, or stimulation parameter such as for example amplitude. In variations that include a variable component, the variable components may be reversibly varied, or irreversibly varied. In some instances, one or more of the variable components may be controlled and varied by an external controller, as described in more detail below. The variable components may be adjusted to adjust or otherwise alter one or more functions of the microstimulator. For example, an adjustable element may be used to alter the resonant frequency of a receiving unit or output unit of the microstimulator, which may control the frequency of output signals that the receiving unit is capable of receiving and the frequency of stimulation signals generated by the microstimulator. Additionally or alternatively, an adjustable element may be used to alter one or more parameters of stimulation provided by a microstimulator (e.g., amplitude, pulse width, etc.).

Figure 5A:
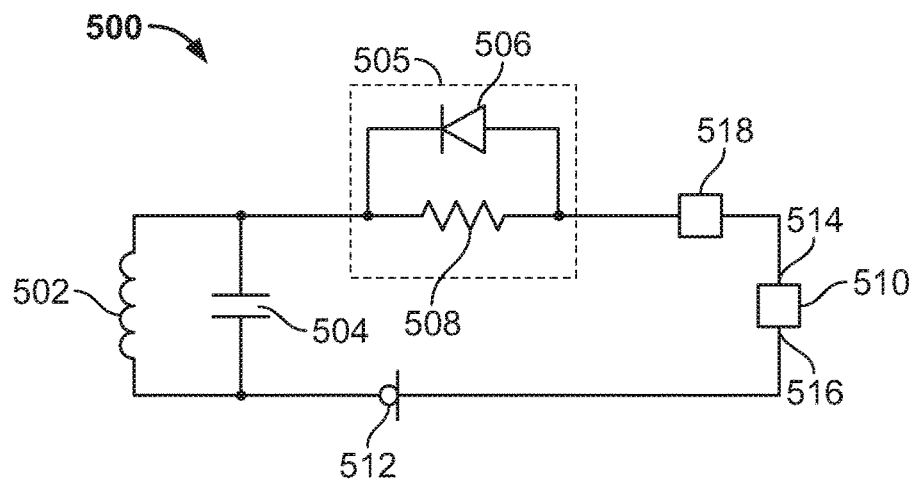
Figure 5B:
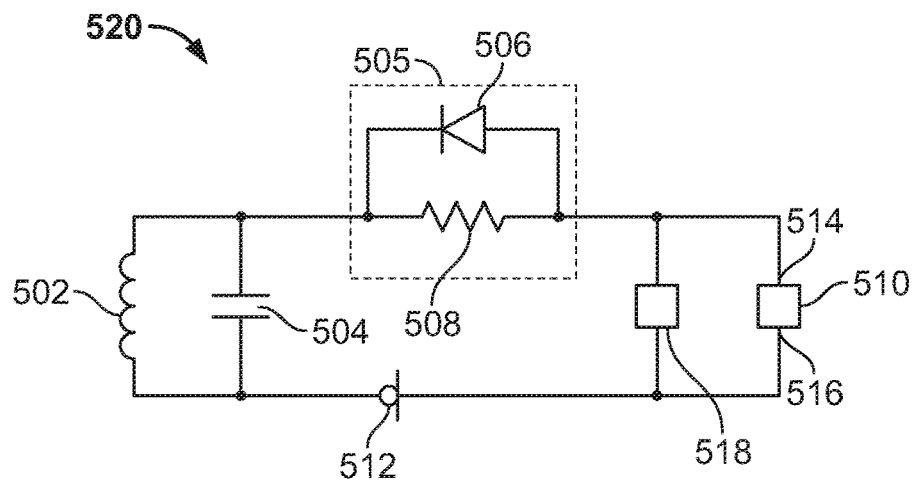

Any of the components of the stimulation circuits described here may be adjustable. For example, in some variations the tuning capacitor (208) from the stimulation circuit (200) may be tuned to adjust the output of the stimulation circuit (200). FIGS. 5A and 5B show two examples of stimulation circuits comprising adjustable elements. FIG. 5A shows a variation of stimulation circuit (500). As shown there, stimulation circuit (500) may comprise a coil (502), a tuning capacitor (504), and a rectifying circuit (505) consisting of a diode (506) and a resistor (508), first (514) and second (516) electrodes, and a current limiting diode (512). These elements may be arranged as described above in relation to FIGS. 2 and 4. Additionally shown there is a variable element (518) positioned in series between the rectification circuit and the first electrode (514). The variable element (518) may comprise a variable impedance element such as an opto-FET, an optically tunable resistor, a capacitor, a programmable current limiter, or the like. The variable element (518) may be adjusted (e.g., via a controller) to alter the current that flows therethrough, which may alter the current that is delivered through a tissue load (510) between the first (514) and second (516) electrodes. FIG. 5B shows another variation of a stimulation circuit (520), which includes the same components as FIG. 5A, but wherein the variable element (518) is positioned in parallel with the first (514) and second (516) electrodes.

Figure 36:
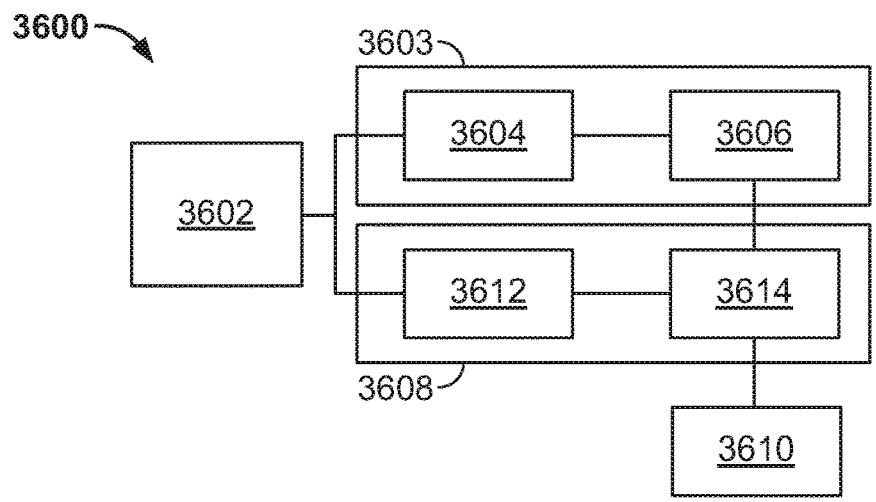
FIG. 36 shows a block diagram of one variation of a passive stimulation circuit for use with the microstimulators described here.

In some variations, a microstimulator may comprise a passive stimulation circuit configured to passively ramp up the amplitude of stimulation signal that is supplied to the patient during stimulation. In some of these variations, the passive stimulation circuit may further be configured to limit the maximum amplitude of the stimulation signal provided to the patient. FIG. 36 shows a block diagram of one variation of a passive stimulation circuit (3600) which may be configured to passively ramp up the stimulation signal produced by the stimulation circuit. As shown there, the passive stimulation circuit (3600) may comprise a receiving unit (3602), a signal conditioning unit (3603), a ramping control unit (3608), and an output unit (3610). The signal receiving unit (3602) may receive one or more output signals from a controller, which may be used to power the signal conditioning unit (3603) and the ramping control unit (3608). In some variations, the signal receiving unit (3602) may be a tuned circuit, such that the signal receiving unit (3602) only receives output signals of a certain frequency or range of frequencies.

The signal conditioning unit (3603) may include an amplitude limiting unit (3604) and a rectification unit (3606), although it should be appreciated that the signal conditioning unit (3606) may comprise any combination of units which may shape or otherwise alter the output signal received by the receiving unit (3602). In variations where the signal conditioning unit (3603) comprises a rectification unit (3606), the rectification unit (3606) may rectify the signal being received by the signal receiving unit (3602), and may comprise a full-wave rectifier or a half-wave rectifier. In variations that include an amplitude limiting unit (3604), the amplitude limiting unit (3604) may limit the amplitude of the stimulation current that is delivered to tissue. For example, the amplitude limiting unit (3604) may comprise one or more zener diodes, current limiting elements, or the like, which may clip or otherwise limit the amplitude of the signals within the stimulation circuit. For example, in some variations the output signal produced by a controller may be larger than the intended stimulation signal amplitude to account for potential alignment differences between the output stage of the controller and the receiving unit of the microstimulator. In these variations, an amplitude limiting unit (3604) may clip the excess power received by the receiving unit (3602). While shown in FIG. 36 as being included in the signal conditioning unit (3603), it should be appreciated that an amplitude limiting unit (3604) may be included in any unit of the stimulation circuit (3600).

The signal conditioning unit (3603) may provide the conditioned output signal to output unit (3610), which may deliver a stimulation signal to tissue via one or more electrodes. The amplitude of the stimulation signal delivered to the output unit (3610) from the signal conditioning unit (3603) may be at least partially controlled by the ramping control unit (3608). In some variations, the ramping control unit (3608) may comprise a charging unit (3612) and a field-effect transistor (3614). The signal conditioning unit (3603) and the output unit (3610) may be connected to the source and drain terminals of the field-effect transistor (3614), and the charging unit (3612) may be connected to the gate terminal of the field-effect transistor (3614). The voltage provided by the charging unit (3612) to the field-effect transistor (3614) may determine the current that flows between the signal conditioning unit (3603) and the output unit (3610). For example, when the charging unit (3612) is uncharged (which may occur when the receiving unit (3602) initially begins receiving an output signal from a controller), the field-effect transistor (3614) may prevent current flow between the signal conditioning unit (3603) and the output unit (3610), thereby preventing delivery of a stimulation signal to the patient. As the receiving unit (3602) provides power to the charging unit (3612), the voltage provided to the gate of the field-effect transistor (3614) increases (e.g., by charging a chargeable component, as will be described in more detail below), which increases the amount of current that may flow between the signal conditioning unit (3603) and the output unit (3610). Accordingly, the amplitude of the stimulation signal provided by the output unit (3610) may increase as the charging unit (3612) charges, and the amplitude of the stimulation signal may automatically be ramped upward until the charging unit (3612) is fully charged. The speed of this ramping may be determined by the rate at which the charging unit (3612) is charged. Additionally, the charging unit (3612) may be configured to discharge when power is not being supplied thereto. This may allow the ramping unit (3602) to reset between different treatment sessions, such that the stimulation circuit can ramp subsequent stimulation signals produced in subsequent treatments.

Figure 43:
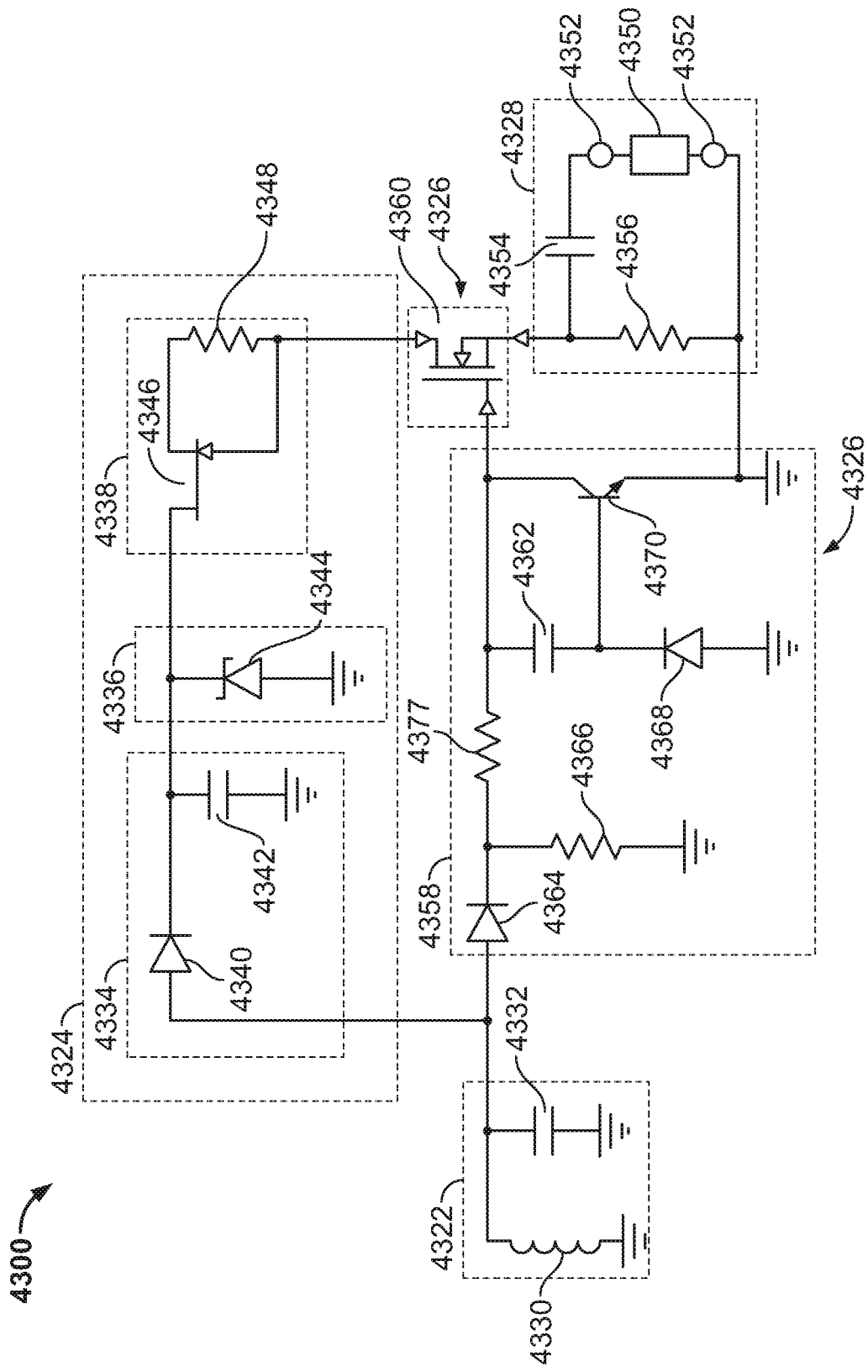
FIG. 43 illustrates a variation of a passive stimulation circuit suitable for use with the microstimulators described here.

FIG. 43 depicts a variation of a stimulator circuit (4320) which may be configured to passively ramp a stimulation signal provided by the stimulation circuit. As shown there, stimulator circuit (4320) may comprise a receiving unit (4322), a signal conditioning unit (4324), a ramping control unit (4326), and an output unit (4328). As described in more detail above with respect to FIG. 36, the receiving unit (4322) may be configured to receive an output signal from a controller (not shown), and may transmit the received signal to the signal conditioning unit (4324) and the ramping control unit (4326). In the variation shown in FIG. 43, the receiving unit (4322) may comprise a resonant circuit comprising a coil (4330) connected in parallel with a tuning capacitor (4332). This resonant may be tuned or otherwise configured to receive an output signal that is transmitted at a certain frequency or range of frequencies. It should be appreciated, however, that the receiving unit (4322) may comprise any suitable components that receive an output signal (e.g., a magnetic field, RF signal, optical signal, ultrasound signal, or the like) and generate a current or voltage therefrom.

As mentioned above, the signal received by the receiving unit (4322) may be passed to the signal conditioning unit (4324) and the ramping control unit (4326). In the variation shown in FIG. 43, the signal conditioning unit (4324) may comprise a rectification unit (4334), an amplitude control unit (4336), and a current source unit (4338). It should be appreciated that the signal conditioning unit (4324) may include only some of these individual components and/or may contain additional components as desired. In variations that include a rectification unit (4334), the rectification unit (4334) may be configured to convert any alternating current signals to direct current signals. The rectifying unit may be a half-wave rectifier or a full-wave rectifier, and in some instances may be configured to smooth the rectified signal. For example, the variation of rectification unit (4334) shown in FIG. 43 may comprise a half-wave rectifier comprising a diode (4340) and a smoothing capacitor (4342) placed at the output of the half-wave rectifier.

In variations that include an amplitude control unit (4336), the amplitude control unit (4336) may be configured to limit the maximum amplitude of the signal delivered by the output stage (4328). For example, the amplitude control unit (4336) shown in FIG. 43 may comprise a zener diode (4344), which may shunt current away from the signal conditioning unit (4324) when the voltage across the zener diode (4344) exceeds a threshold voltage. It should be appreciated that the amplitude control unit (4336) may comprise any suitable current or voltage limiting elements, which may be positioned in any suitable portion of the stimulator circuit (4300) (e.g., as part of the receiving unit (4322), the signal conditioning unit (4324), the ramping control unit (4326), the output unit (4328), combinations thereof, and the like). In some variations, a stimulation circuit may comprise a plurality of amplitude control units, each of which may limit a different aspect of the generated stimulation signal, or may limit aspects of the generated control signal at different locations.

In variations where the signal conditioning unit (4324) comprises a current source unit (4338), the current source unit (4338) may be configured to act as a voltage-controlled current source which may output a current based on a voltage input received by the current source unit (4338). For example, in some variations (such as that shown in FIG. 43), the current source unit (4338) may comprise a transistor (4346) (e.g., a JFET, MOSFET, BJT) where the gate and the source of the transistor (4340) are connected (e.g., via a resistor (4348) or the like). In some variations, the current source unit (4338) may act as a constant-current source that may provide a constant current when any voltage above a certain threshold is applied to an input of the current source unit (4338). In some variations, a current source unit may comprise one or more current-limiting diodes or the like. In some variations the current source unit (4338) may comprise a current mirror circuit. The current mirror circuit may be symmetric or asymmetric.

Once the received output signal has been conditioned by the signal conditioning unit (4324), the signal may be passed to the output unit (4328). The output unit (4328) may thus deliver the processed signal as an output signal to tissue (4350) via electrodes (4352). In some variations, the output unit (4328) may be configured to allow for passive charge balancing. For example, output unit (4328) may comprise a capacitor (4354) and resistor (4356). The capacitor (4354) may charge when signal conditioning unit (4324) is delivering current to the output unit (4328) and tissue (4350), and may discharge when the signal conditioning unit (4324) is not delivering current to the output unit (4328), which may allow the output unit (4328) to provide a biphasic, charge-balanced, stimulation signal to tissue (4350). In some variations, the output unit (4328) may comprise a current-limiting device (not shown) or the like, which may limit the magnitude of the balancing current produced by the capacitor (4354).

As mentioned above, the ramping control unit (4326) may be configured to ramp the signal provided from the signal processing unit (4324) to the output unit (4326). As shown in FIG. 43, the ramping control unit (4326) may comprise a charging unit (4358) and a field-effect transistor (4360). The field-effect transistor (4360) may be any suitable transistor (e.g., a MOSFET, BJT, or the like). The signal conditioning unit (4324) and the output unit (4328) may be connected to the source and drain terminals of the field-effect transistor (4360), and the charging unit (4326) may be connected to the gate terminal of the field-effect transistor (4360). As mentioned above, the current that passes between the signal conditioning unit (4324) and the output unit (4328) through the field-effect transistor (4360) may be dependent on a voltage provided by the charging unit (4326) to the gate terminal of the field-effect transistor (4360). As such, the ramping control unit (4326) may be configured to increase the amplitude of the stimulation signal as the charging unit (4326) charges.

Charging unit (4326) may be configured to increase the voltage provided to the field-effect transistor (4360) as the receiving unit (4322) receives an output signal generated by a controller. For example, as shown in FIG. 43, the charging unit (4326) may comprise a capacitor (4362) which may be charged as receiving unit (4322) receives the output signal. As the capacitor (4362) charges, the voltage applied to the field-effect transistor (4360) may increase, which may thereby increase the current that may pass from the signal conditioning unit (4324) to the output unit (4328). This may result in a ramped stimulation signal produced by the microstimulator. In some instances, the charging unit (4326) may comprise a rectifying diode (4364) or other rectification circuit which may rectify the signal received from the receiving unit (4322). Additionally, the charging unit (4326) may comprise one or more additional components (e.g., resistors (4366) and (4377), diode (4368) and transistor (4370), which may control the rate at which the capacitor (4362) charges and discharges. While the stimulator circuits described above with respect to FIGS. 36 and 43 are passive circuits that passively ramp a stimulation signal without the use of internal logic or intelligence, it should be appreciated that in some variations a stimulation circuit as described here may comprise an microcontroller or other internal logic that may control the ramping of a stimulation signal.

The microstimulators described above may take any of several shapes and forms. FIGS. 6A-6H illustrate exemplary microstimulators suitable for use with the stimulation systems described here. It should be appreciated that each of the microstimulators shown in FIGS. 6A-6H may include any of the circuitry or functionality described in more detail above (e.g., a passive stimulation circuit), and may be hermetically sealed. The microstimulators may comprise any suitable materials or combinations of materials, such as, for example, one or more metals (titanium, niobium, stainless steels, platinum, alloys thereof, combinations thereof, or the like), one or more polymers, one or more ceramics, combinations thereof or the like. FIG. 6A depicts one variation of a microstimulator (600) that is shaped like a capsule with a body and two ends. The body may be relatively straight with a cylindrical, square, rectangular, trapezoidal or other shaped cross section and rounded, pointed, or other shaped ends. The capsule-shaped microstimulator (600) may include electrodes (not shown) at one or more ends and/or along the length thereof, as will be described in more detail below. The microstimulator may have any suitable dimensions. For example, in some variations, the length of the stimulator may be between about 6 millimeters to about 30 millimeters. In some of these variations, the length of the stimulator may be about 16 millimeters. In some variations, the height of the microstimulator may be between about 0.5 millimeter and about 2 millimeters. In some of these variations, the height of the microstimulator may be about 1.5 millimeters. In some variations, the width of the microstimulator may be between about 3 millimeters and about 10 millimeters. In some variations, the width of the microstimulator may be about 5 millimeters.

FIG. 6B depicts another variation of a microstimulator (602) that is shaped like a capsule having a curved body. In these variations, the curvature of the body may be configured to accommodate an anatomical structure of a patient, such as a fossa for a lacrimal gland. It should be appreciated that the body of the microstimulator (602) may have any suitable ends and cross-sectional shape as described above in relation to the microstimulator (600) shown in FIG. 6A. Additionally, the microstimulator (602) may comprise one or more electrodes (not shown), as will be described in more detail below.

While shown in FIG. 6B as having a single curve, it should be appreciated that the microstimulator (602) may comprise multiple curves. For example, FIG. 6C shows a microstimulator (604) comprising multiple curves. As shown there, the microstimulator (604) includes a first curve in one direction and a second curve in a second direction. The curves may be formed in a single plane, as shown in FIG. 6C, or may be formed in different planes. Additionally, the microstimulator (604) may be a flexible device or may be configured to conform to an anatomical structure of a patient, such as a fossa for the lacrimal gland.

FIG. 6D depicts another variation of a microstimulator (606) that is configured as a planar structure. In some of these variations, the microstimulator (606) may have a first form when it is being inserted into a patient and manipulated to have a second form during or after delivery, as will be described in more detail below. The planar microstimulator (606) may be flexible and/or may be configured to conform to one or more anatomical structure, such as a fossa for a lacrimal gland.

FIG. 6E illustrates a flexible segmented microstimulator (608) for use with the stimulation systems described here. The flexible segmented microstimulator (608) may include multiple electrodes (610) separated by body segments (612). The electrodes may be implemented as part of a stimulation circuit for stimulating one or more anatomical targets such as a lacrimal gland. While the microstimulator (608) is shown in FIG. 6E as forming a single curved such that the electrodes (610) are aligned along the curve, it should be appreciated that the microstimulator need not form a single curve. For example, FIG. 6F shows a variation of a flexible segmented microstimulator (614) comprising a plurality of electrodes (616) connected by body segments (618) such that electrodes (616) extend approximately parallel to other electrodes (616).

FIGS. 6G and 6H illustrate one variation of a microstimulator (620) that is incorporated into a contact lens (622). As shown there, the contact lens (622) may be positioned over an iris (626) of an eye (630) and may comprise one or more electrodes (628). The contact lens (622) may be in contact with the cornea, and its inner surface may conform to the shape of the cornea and/or the conjunctiva. The microstimulator (620) may contain any suitable number of electrodes (628) (e.g., one, two, or three or more electrodes), and may deliver an electrical current to the surface of the eye, which may result in reflex activation.

In some variations, the contact lens (622) may have a power supply (e.g., a battery or the like). Additionally or alternatively, the contact lens (622) may comprise one or more coils (624) or other elements which may receive energy from a controller. FIG. 6H is an enlarged view of the coils (624) shown in FIG. 6G. The microstimulator (620) may be powered in any suitable manner, such as by one or more of the controllers as described below. In some variations, the microstimulator (620) may be powered by a magnet placed within the eyelids. In some variations, the microstimulator may be activated by blinking an eye, in which case a blink detection mechanism may be used in conjunction with the microstimulator.

Figure 7F:
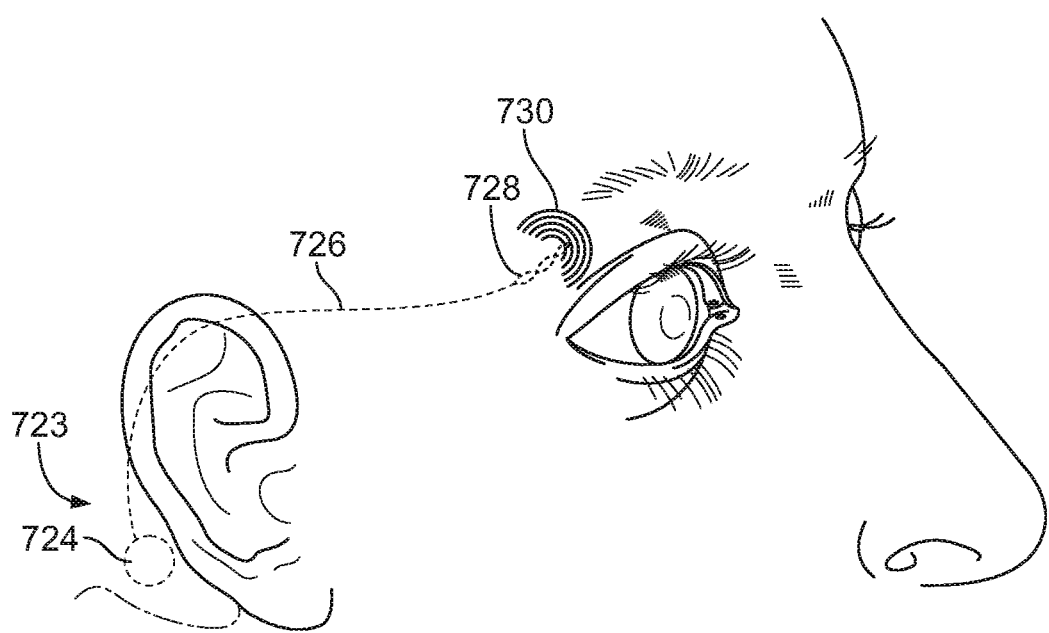

As mentioned above, the microstimulators described here may comprise one or more electrodes. The electrodes may be attached to any suitable portion or portions of the microstimulator, and in some instances may be connected to the microstimulator via one or more leads. In some variations, the electrodes may be configured to allow for capacitive charge transfer, but not faradaic charge transfer. When the microstimulator comprises a planar body, such as the microstimulator (606) described above with respect to FIG. 6D, the microstimulator may include electrodes on both sides of the planar structure, or may only include electrodes on one side of the planar structure. The microstimulators may comprise any suitable number of electrodes (e.g., one, two, three, or four or more electrodes). FIGS. 7A-7F depict illustrative microstimulators having different electrode configurations. For example, FIG. 7A illustrates a microstimulator (700) including a stimulation circuit (702) with electrodes (704) coupled thereto. It should be appreciated that the stimulation circuit (702) shown in FIG. 7A may be any suitable stimulation circuit, such as one or more of the stimulation circuits described in more detail above. Electrodes (704) may be coupled to the stimulation circuit (702) at the ends of the microstimulator (700), as shown in FIG. 7A, or may be connected along the body of the microstimulator (700).

FIG. 7B shows another variation of a microstimulator (706) which includes electrodes (708) that are attached to the microstimulator (706) via small round contact points on the exterior of the microstimulator (706). While shown in FIG. 7B as being attached to the ends of the microstimulator (706), one or more of the electrodes may be attached along the body of the microstimulator (706). In other variations, the electrodes may be at least partially embedded or nestled into a surface of the microstimulator. For example, FIG. 7C illustrates a microstimulator (708) having nestled electrodes (710). While the electrodes (710) are shown in FIG. 7C as being configured as a circular pattern, it should be appreciated that a nestled electrode (710) may have any suitable shape and/or pattern.

In some variations, one or more electrodes may be attached to a microstimulator via one or more leads. The leads may or may not be flexible or comprise one or more flexible portions. For example, FIG. 7D depicts one variation of a microstimulator (712) comprising electrodes (714) attached to the microstimulator (712) via flexible leads (716). The flexible leads (716) may be manipulated into one or more shapes to traverse through one or more regions of the body and/or conform thereto. FIG. 7E shows another variation of a microstimulator (718) that includes electrodes (720) attached to the microstimulator (718) via rigid leads (722). It should be appreciated that in variations where a microstimulator comprises a lead, the microstimulator may comprise any suitable number of leads (e.g., one, two, three, or four or more leads), and each lead may include any suitable number of electrodes (e.g., one, two, three, or four or more electrodes).

In variations where a microstimulator includes electrodes attached to the body of the microstimulator via one or more leads, the leads may allow for the body of the microstimulator to be located remotely from the site of stimulation. For example, FIG. 7F shows one variation of an implanted microstimulator (723) comprising a body (724) and a plurality of electrodes (728) attached to the body (724) via a lead (726). As shown there, the electrodes (728) may be configured to deliver a stimulation signal (730) to tissue around the eye (e.g., the lacrimal gland), but the body (724) (which may include one or more stimulation circuits) may be remotely positioned (e.g., behind the ear as shown in FIG. 7F, or at another location in the head, neck, or torso).

Figure 8A:
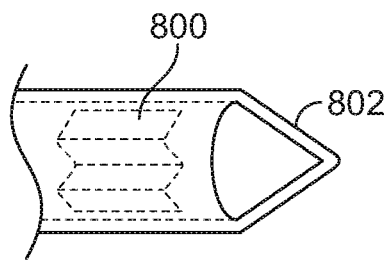
FIGS. 8A and 8B depict one variation of a microstimulator that is configured to change shape upon release from a delivery device.
Figure 8B:
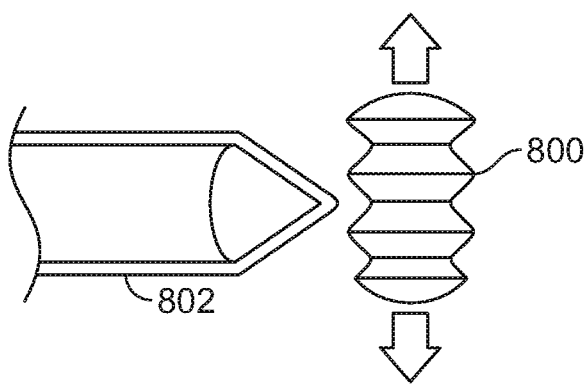

As mentioned above, a microstimulator may be configured to change shape upon implantation from a delivery device. For example, FIGS. 8A and 8B depict one variation of a microstimulator (800) that is configured to change shape upon implantation from a delivery device (802) (e.g., a needle or the like). Specifically, the microstimulator (800) may have a first low-profile form when placed inside of a delivery device. The microstimulator (800) may be rolled, crimped, folded or otherwise manipulated to achieve this low-profile form. For example, in FIG. 8A, the microstimulator (800) is shown as being folded into the first low-profile form.

When the microstimulator (800) is released from the delivery device (802) (e.g., via a pusher or the like), the microstimulator (800) may take on a second form. When in its second form, the microstimulator (800) may conform to one or more anatomical structures, such as a fossa for the lacrimal gland. The microstimulator (800) may transition between the first and second forms in any suitable manner. For example, in some variations the microstimulator (800) may unfold, unfurl, or otherwise change shape due to release of stored energy in the microstimulator (800) (e.g., shape memory energy, spring or coil energy, or the like). In other instances, the microstimulator (800) may change shape due to mechanical manipulation, or by virtue of degradation or other removal of a structure holding the microstimulator (800) in the low-profile form.

In some variations, the microstimulators may comprise one or more components which may aid in insertion of the device into tissue. For example, in some variations a microstimulator may comprise one or more rounded edges which may reduce tissue damage as the microstimulator is advanced into or past tissue. Additionally or alternatively, a microstimulator may comprise one or more sharpened tips which may aid in advancing the microstimulator at least partially into or through tissue. For example, FIGS. 9A and 9B show one such variation of a microstimulator (900). As shown in FIG. 9A, the microstimulator (900) may comprise a beveled tip (902). In some instances, the microstimulator (900) may be advanced using a delivery device (904), as shown in FIG. 9B, and the narrowed edge (906) of the beveled tip (902) may cut or otherwise separate tissue as the microstimulator (900) is advanced using the delivery device (904). While shown in FIG. 9A as being beveled, the tip of a microstimulator may be pointed or otherwise sharpened. It should also be appreciated that the sharpened tip may comprise one or more barbs, as will be described in more detail below, which may help to prevent migration after delivery of the microstimulator.

FIG. 10 shows another variation of a microstimulator (1000) which comprises a helical barb (1002) extending therefrom. The helical barb (1002) may be configured such that the microstimulator (1000) may be rotated during delivery to screw the helical barb (1002) into tissue. This may assist in advancing the microstimulator, and also may anchor the microstimulator in place relative to tissue.

In variations where a microstimulator comprises a sharpened tip, the tip may be formed as a single device or may be formed separately from and attached to the microstimulator. In some variations, the tip may be configured to degrade or otherwise detach from the microstimulator after implantation. For example, FIGS. 11A and 11B show one such variation of a microstimulator (1100). As shown in FIG. 11A, microstimulator (1100) may comprise a body (1102) and a biodegradable pointed tip (1104). The pointed tip (1104) may aid in delivery of the microstimulator (1100) by puncturing or otherwise separating tissue during advancement of the microstimulator (1100). Once in place in the body, the tip (1104) may biodegrade such that the body (1102) of the microstimulator (1100) is left in place, such as shown in FIG. 11B. The biodegradable tip may be made from any suitable biocompatible, biodegradable material or materials, such as one or more biodegradable sugars or polymers (e.g., PLA, PLGA, or the like).

The microstimulators described here may also comprise one or more elements which may help to maintain the microstimulator in place relative to tissue. In some variations, the microstimulator may comprise one or more coatings (e.g., an adhesive coating or the like) which may help hold in the microstimulator in place relative to tissue. In other variations, the microstimulator may comprise one or more materials (e.g., a Dacron covering) or structures that may promote tissue ingrowth. In some variations, the microstimulator may comprise one or more fixation elements, such as hooks, barbs, anchors, bumps, or other protrusions. For example, FIG. 12 illustrates a microstimulator (1200) having a plurality of barbed fixation elements (1202). While the fixation elements (1202) are shown in FIG. 12 as being attached to the body of the microstimulator, it should be appreciated that fixation elements may be affixed to any suitable portion of the microstimulator. In variations where the microstimulator comprises a sharpened tip, the tip may comprise one or more fixation elements. In variations where the microstimulator comprises one or more leads, one or more of the leads may comprise one or more fixation elements. For example, FIG. 13 depicts another variation of a microstimulator (1300) which comprises leads (1302) having barbed fixation elements (1304) located thereon. It should be appreciated that the leads may comprise any suitable fixation element, such as those described immediately above.

It should be appreciated that a microstimulator may comprise a plurality of different fixation elements. For example, FIG. 14 illustrates a variation of a microstimulator (1400) comprising a plurality of bumps (1402) and ring members (1404) protruding from the microstimulator (1400). In these variations, the bumps (1402) and the ring members (1404) may resist movement of the microstimulator (1400) relative to tissue. Additionally, the ring members (1404) may promote tissue ingrowth which may further help hold microstimulator (1400) in place relative to tissue. Additionally or alternatively, one or more sutures (not shown) may be threaded through the ring members to help sew the device in place relative to tissue. The microstimulator may comprise any suitable combination of fixation elements as described above.

In some variations of the microstimulators described here, the microstimulator may comprise one or more features to facilitate minimally invasive retrieval. For example, FIGS. 15A-15C depict illustrative variations of microstimulators that include retrieval features. 15A shows a variation of a microstimulator (1500) comprising a recapture loop (1502). The recapture loop (1502) may comprise an aperture (1504), and may aid in retrieval of the microstimulator (1500). Specifically, during retrieval, a physician may use a retrieval device such as forceps or a hook device to engage recapture loop (1502) and remove the microstimulator (1500) from its position within the body. In some variations, a suture (not shown) may be attached to the recapture loop (1502), and the suture may be engaged by a physician (e.g., via a retrieval device) to pull the microstimulator (1500) from its position. A microstimulator may or may not comprise multiple recapture loops (1502), and these recapture loops may be located at one or both ends of the microstimulator (1500), and/or along the length of the body of the microstimulator (1500). While the microstimulator is shown in FIG. 15A as having a capsule-shaped body similar to the microstimulator (600) described above with respect to FIG. 6A, it should be appreciated that any microstimulator described here may comprise a recapture loop.

FIG. 15B illustrates another variation of a microstimulator (1510) having a recapture magnet (1512). Recapture magnet (1512) may be engaged by another magnetic device to assist in removal or repositioning of the microstimulator (1510). It should also be appreciated that the recapture magnet (1512) may also be engaged by a delivery device and may assist in positioning the microstimulator (1510) during delivery.

FIG. 15C illustrates another variation of a microstimulator (1520) having a shaped retrieval tab (1522). Also shown there is a retrieval device (1524) having an aperture (1526) at a distal end thereof. To aid in retrieval of the microstimulator (1520), the retrieval device (1524) may be advanced so that the aperture (1526) receives a portion of the retrieval tab (1522) in the aperture (1526), and may be rotated to temporarily connect the microstimulator (1520) and the retrieval device (1524). Once connected, the retrieval device (1524) may be manipulated or withdrawn to reposition or remove the microstimulator.

FIGS. 42A-42C illustrate another variation of a microstimulator (4200) described here. Specifically, FIG. 42A shows a perspective view of the microstimulator (4200). As shown there, the microstimulator (4200) may comprise a housing (4202) and a flexible extension (4204) connected to the housing (4202). The housing (4202) may be hermetically sealed, and may contain some or all of the stimulation circuitry therein. The microstimulator (4200) may comprise any stimulation circuits, such as those described above. The housing (4202) may be formed from one or more metals (e.g., titanium) or other biocompatible materials.

The extension (4204) may be formed from a flexible material such as silicon, and may comprise a first electrode (4206), a second electrode (4208), and a coil (4210). In some variations, the extension (4204) may be a molded component, such as molded silicon. The flexible extension (4204) may conform to one or more portions of the anatomy (e.g., the orbit or the lacrimal gland) when implanted in tissue. FIG. 42B shows a side view of the microstimulator (4200). As shown there, the thickness of the extension (4204) may be less than that of the housing (4202), and may taper to the thickness of housing (4202). It should be appreciated that in some variations the thickness of the extension (4204) may be the same as or greater than the thickness of the housing (4202). Additionally, the width of the extension (4204) is shown in FIG. 42A as being greater than the width of the housing (4202), and may taper to the thickness of the housing (4202). In some variations, however, the housing may have the same width, or may be wider than the extension.

While shown in FIG. 42A as having two electrodes, it should be appreciated that the microstimulator (4200) may comprise any suitable number of electrodes (e.g., one, two, three, or four or more electrodes). Some or all of the electrodes may be textured or patterned, which may enhance the effective surface area of the electrodes. One or more of the electrodes may be recessed, which may provide for more uniform charge density on the electrode surface. In the variation shown in FIG. 42A, the first electrode (4206) and second electrode (4208) are positioned on the same side of the extension (4204), although in some variations the first (4206) and second (4208) electrodes may be positioned on opposite sides of the extension (4204). Additionally, while shown in FIG. 42A as having a coil (4210), it should be appreciated that the microstimulator (4200) may comprise any energy receiving element or elements as described in more detail below.

The electrodes (4206) and (4208) and coil (4210) may be connected to the microstimulator circuitry via one or more feedthroughs. For example, FIG. 42C shows a perspective view of the housing (4202) with the extension (4204) removed. As shown there, housing (4202) may comprise a plurality of feedthroughs (4212) that extend through the housing (4202). One or more elements (e.g., one of the electrodes (4206) or (4208) or the coil (4210)) may be electrically connected to the hermetically-sealed stimulation circuitry by connection to the feedthroughs (4212). Additionally, some of the feedthroughs (4212) may comprise an insulating member (4214) which may electrically isolate the feedthrough (4212) from the housing (4202).

The microstimulators described here may be made from any materials or combinations of materials. For example, the composition of the electrode may include, but is not limited to, platinum, iridium, platinum iridium, iridium oxide, sputtered iridium oxide, titanium nitride, tantalum, and combinations thereof. In some variations, the implantable microstimulators described here may be configured to be compatible with magnetic resonance imaging (MRI) machines. In some of these variations, the device may be configured to minimize device movement that may result from magnetic forces created during MRI imaging or minimize heating that may occur in the components of the microstimulator. For example, in some variations, the microstimulator may be made from non-ferromagnetic or reduced-ferromagnetic materials. In other variations, the microstimulator may comprise ferromagnetic materials, but the relative amount of these components may be small enough such that forces provided on these components during MRI imaging do not substantially move the device. In other variations, the microstimulators may be configured such that MRI imaging does not cause inadvertent stimulation or other activation of the microstimulator. For example, when the microstimulators comprise a receiving circuit having a resonant frequency (as discussed in more detail above), the microstimulator may be configured such that the resonant frequency is outside of the frequency ranges produced during MRI imaging (e.g., the frequencies produced by the main field, gradient field, and/or RF fields of an MRI scanner).

Figure 37:
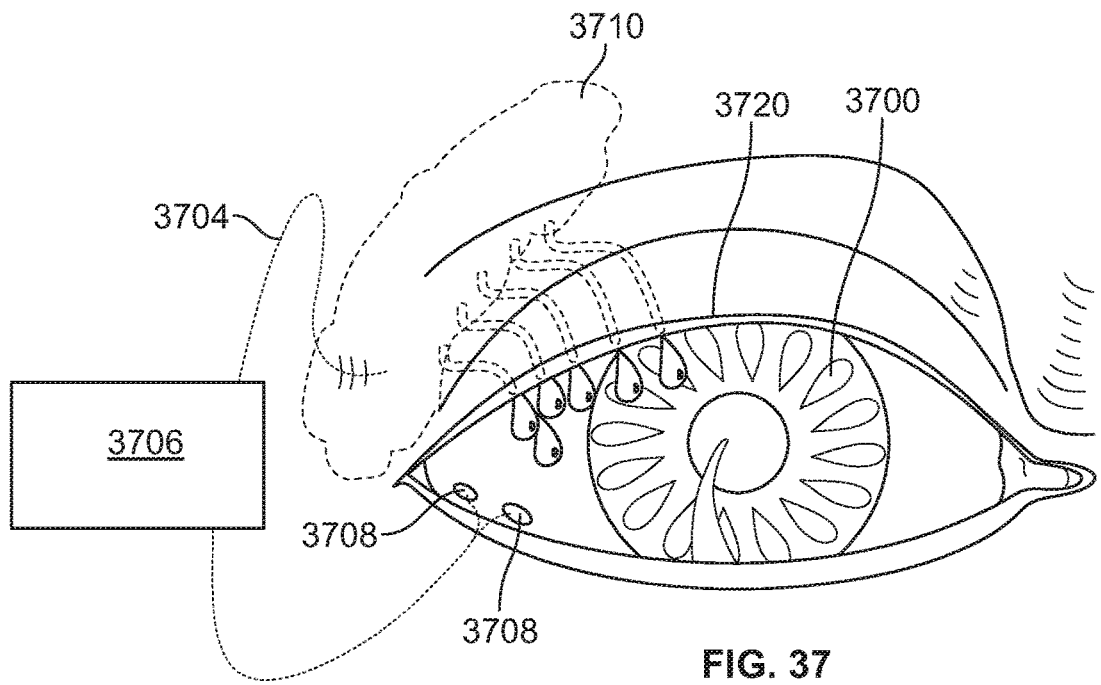
FIG. 37 shows a variation of a microstimulator suitable for use with the stimulation systems described here.

In some variations, the microstimulator may comprise one or more sensors which may measure one or more physical parameters of the patient. In some variations, the sensors may be used to implement closed loop stimulation of one or more anatomical structures. FIG. 37 illustrates a microstimulator implemented with closed loop control of lacrimal stimulation. As shown there, a microstimulator (3706) may include sensors (3708) and an electrode-bearing lead (3704). The sensors (3708) may be positioned on the patient's eyeball, and the lead (3704) may extend between microstimulator (3706) and one or more anatomical targets, such as a lacrimal gland (3710). The microstimulator (3706) may be configured to stimulate the anatomical targets via lead (3704) based on closed-loop stimulation using signals measured by the sensors (3708). When stimulated by one or more signals, tears may be produced under the upper eye lid (3720) and may travel over an iris (3700) of the patient's eye assembly. In variations where the microstimulator comprises a sensor, the microstimulator may be configured to transmit information received from the sensor to a controller.

Closed loop stimulation may work by detecting a condition (surface impedance to detect wetness) that provides information about the requirement of tear production and generating a condition signal. The microstimulator (or controller) may then modulate its output in response to this condition signal to modify its output in tear production. Detecting the condition may include measurement of one or more variables. Measured variables for use in the closed loop stimulation may include one or more of tear conductivity, tear volume, and gland conductivity. A sensing element may be part of an implantable microstimulator, or could be separate (e.g., provided in a contact lens, part of the controller, etc.) from the implanted microstimulator. The adjustment of stimulation output may be based on an algorithm.

Controller

As mentioned above, the stimulation systems described here may comprise a controller, which may communicate with the stimulation devices described here to transmit and/or receive power, information, or the like. The components of the controller and the microstimulator may be implemented as a single device or as separate devices. The controller may communicate with the microstimulator wirelessly and/or via a wired connection. The controller may be configured for implantation within the body, or may be configured to remain external to the body. The controller may be disposable, may be reusable, or may be partially reusable. In some instances, one or more components of the microstimulator may be reusable, while other components may be disposable. In some instances, the controller may be rechargeable.

When the controller is configured to remain external to the body, the controller may be configured to be at least temporarily affixed to the patient. For example, the controller may be configured to adhesively affix to the patient's skin, may be magnetically attached to a patient's skin (e.g., via one or more magnets positioned in the patient's head), may be incorporated into a pair of eyeglasses, may be configured to be worn over or otherwise attach to the ear, may be incorporated into or otherwise couple to a wristwatch or bracelet, or the like. The controller may be configured for placement against any suitable skin surface, such as the temple, forehead, brow, ear, neck, or the like, as may be appropriate to position a controller in proximity to an implanted stimulator. In other variations, the controller may comprise one or more hand-held devices, such as a key fob.

Figure 16A:
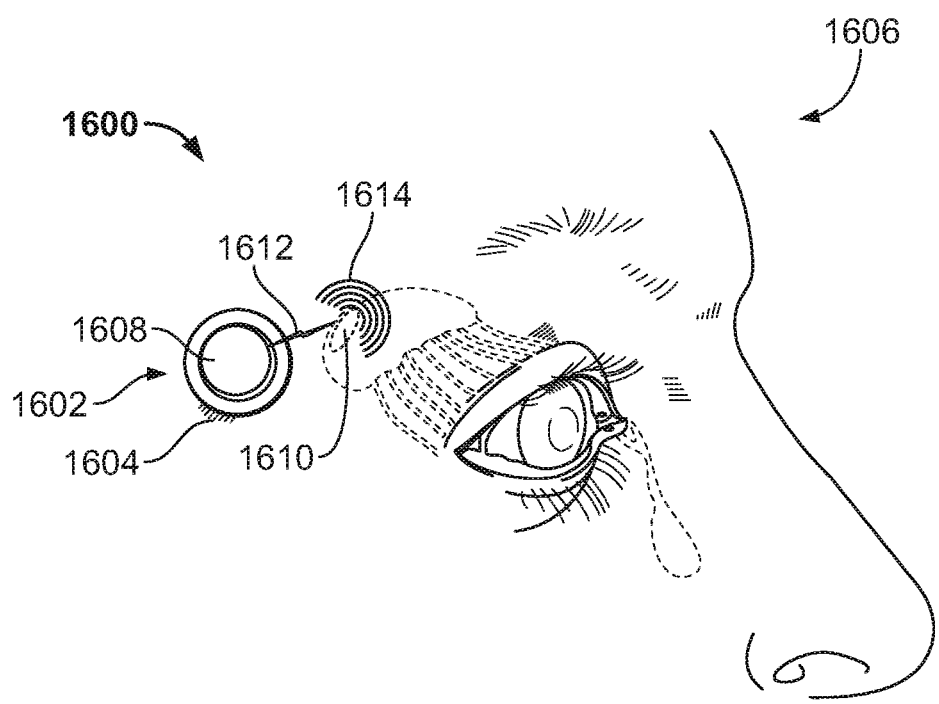
FIGS. 16A-16C depict variations of controllers suitable for use with the stimulation systems described here.

In some variations, the controller may comprise a patch or similar structure which may be configured to at least temporarily affix the controller to a patient. FIG. 16A shows one such variation of a stimulation system (1600) which includes a controller (1602) configured to adhesively affix to the skin (1604) of a patient (1606). As shown there, the controller (1600) may comprise a patch (1608) with one or more adhesive layers (not shown) which may temporarily connect the patch (1608) to the patient (1606). The controller (1602) may communicate with a microstimulator (1610) via a wireless signal (1612), as described in more detail below. The microstimulator (1610) may in turn provide an output signal (1614) for stimulating one or more anatomical targets of a patient, as described hereinthroughout.

Figure 16B:
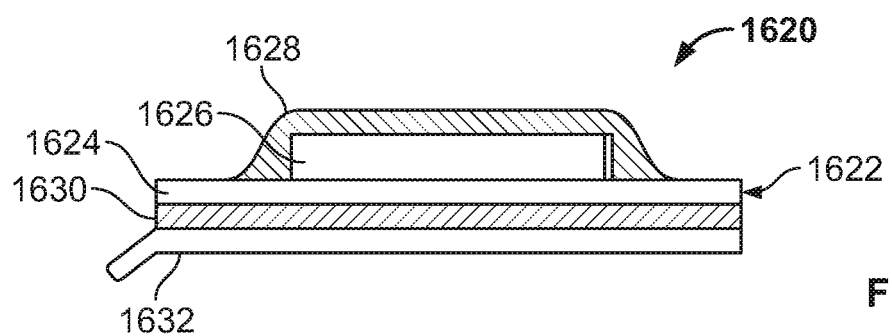

FIG. 16B shows a cross-sectional side view of one variation of a controller (1620) which comprises a patch (1622). As shown there, the patch (1622) may comprise a base layer (1624), controller circuitry (1626), a coating layer (1628), an adhesive layer (1630), and a release liner (1632). The release liner (1632) may be peeled off or otherwise removed from adhesive layer (1630), and the patch (1622) may be placed against a surface (e.g., the skin of a user) to temporarily affix the patch (1622) thereto via the adhesive layer (1630).

While the controller circuitry (1626) is shown in FIG. 16B as being separate from base layer (1624) and coating layer (1628), it should be appreciated that the circuitry of a controller may be incorporated into any portion of the patch. For example, in some instances at least some of the controller circuitry may be incorporated into one or more layers of the patch (e.g., a base layer, coating layer, adhesive layer, combinations thereof, or the like). In variations where a patch comprises a base layer, the base layer (or one of the other patch layers) may include one or pads or fabric layers, which may provide additional comfort to a patient when a controller is attached thereto. Additionally or alternatively, the base layer may comprise a printed circuit board which incorporates one or more components of the controller circuitry.

While the patch (1622) is shown in FIG. 16B as having a coating layer (1628), it should be appreciated that a patch need not have any coating layer, or may be have multiple coating layers. In variations where a patch comprises one or more coating layers, the coating layers may provide one or more useful functions. In some instances, a coating layer may comprise a material (which may be a soft durometer material) such as silicone, latex, parylene, one or more plastics, etc., and may be configured to protect one or more device components, such as the controller circuitry. The coating layer may, in some instances, be configured to provide additional comfort to a patient. In some variations, the coating layer may be configured to prevent accidental removal of the patch. Additionally or alternatively, the patch may comprise an insulating coating layer (e.g., a layer made from latex, parylene, or the like), which may help maintain hermeticity of the patch and/or insulate a patient from voltages generate within the device. Additionally or alternatively, the patch may comprise a layer which may intensify or direct a magnetic field produced by the controller, and/or may reduce eddy current loss. These layers may comprise one or more ferrites, patterned ferrites, or the like.

Figure 44:
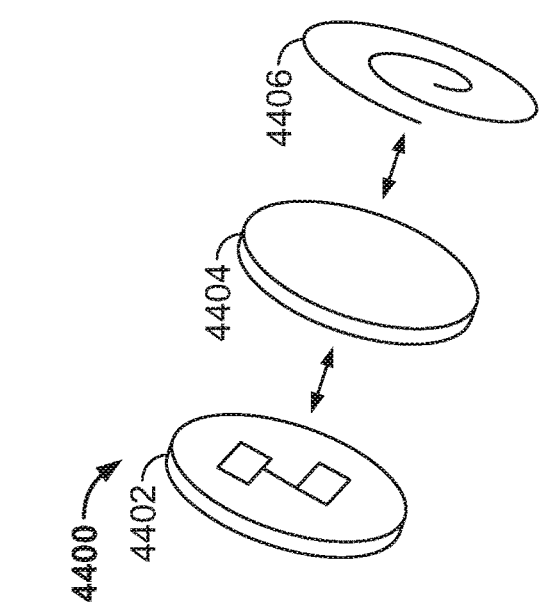
FIG. 44 depicts a variation of a controller suitable for use with the stimulation systems described here.

In some variations, a coating layer may be disposed between different components of the controller circuitry. For example, FIG. 44 shows an exploded view one such variation of a patch (4400). As shown there, patch (4400) may comprise a circuit board (4402), a reflective layer (4404), and a coil (4406). The reflective layer (4404) may be positioned between the circuit board (4402) and the coil (4406), and may be configured to shield the components of the circuit board (4402) from a magnetic field created by the coil (4406) during generation of an output signal. For example, the reflective layer (4404) may minimize eddy currents that may be created in circuit components of the circuit board (4402). Additionally, the reflective layer (4404) may shape or otherwise direct the generated magnetic field away from the reflective layer (4404), which may increase the power transmission to an implanted microstimulator. The patch (4400) may comprise one or more adhesive layers or other layers as discussed in more detail hereinthroughout.

It should be appreciated that one or more of the patch components may be flexible and/or may be configured to at least partially conform to the contours of the patient. For example, the circuitry of the controller may be incorporated into a flexible substrate or layer (e.g., a flexible circuit board). In variations where a patch comprises one or more pads or fabric layers, these layers may be flexible. The patch may also be formed from one or more translucent materials, or may be colored to match a patient's skin tone, which may make the patch less noticeable.

As discussed above, the patch may comprise one or more adhesive layers for affixing the controller to a surface. In some variations, the adhesive layer may comprise a double-sided adhesive, in which one side of the adhesive adheres to one or more patch components (e.g., a fabric layer, printed circuit board, or the like) and the other side of the adhesive adheres to the skin. An adhesive layer may be configured to last any suitable amount of time. In some variations, the adhesive layer may be configured to last for one or more hours (e.g., one hour, four hours, eight hours, or the like), one or more days (e.g., one day, two days, three days, etc.), or one or more weeks (e.g., one week, two weeks, etc.). The patches described here may further comprise a release liner, but need not. In variations that do comprise a release liner, the release liner may comprise a wax-coated paper or other material that temporarily covers an adhesive layer. The release liner may be peeled off or otherwise removed to expose a surface of the adhesive layer, thereby allowing the adhesive layer to be placed against skin or another desired surface. In some variations, the controller may be configured such that removal of a release liner activates one or more functions of the device. For example, in some variations, removal of a release liner may initiate the generation of a timed output signal, as will be described in some detail below.

Figure 16C:
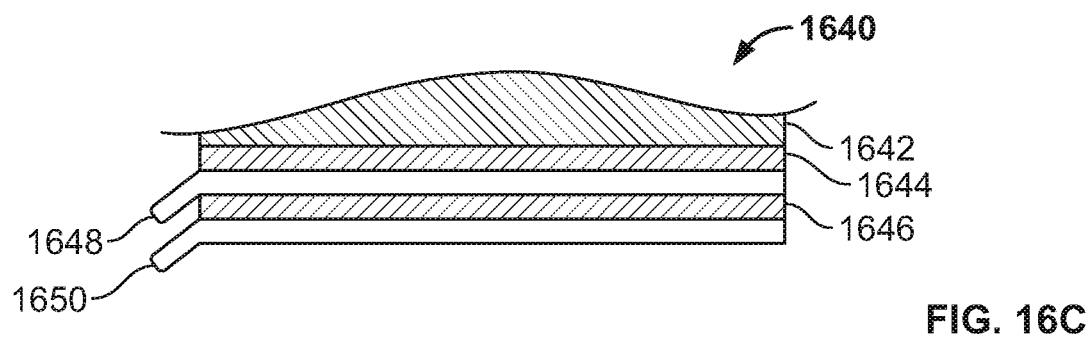

As mentioned above, in some variations a patch may comprise multiple adhesive layers. FIG. 16C shows on such example of a controller (1640) comprising a patch (1642) having a first adhesive layer (1644) and a second adhesive layer (1646). Also shown there is a first release liner (1648) positioned between the first and second adhesive layers, and a second release liner (1650) covering the second adhesive layer (1646). In these variations, the different adhesive layers may be used to attach the patch (1642) to a patient during different time periods. For example, the second release liner (1650) may be removed to expose second adhesive layer (1646), and the controller may be attached to a patient or other surface via the second adhesive layer (1646) for a first period of time. After this period of time, the first release liner (1648) may be removed to remove what may remain of the second adhesive layer (1646) and to expose the first adhesive layer (1644). The controller may then be reattached to the patient or other surface via the first adhesive layer (1644). In this way, multiple adhesive layers may allow for continued use of a controller, even after one or more of the adhesive layers have already been used. For example, in some variations a controller may comprise a plurality of adhesive layers separated by respective release liners. The patient may remove a release liner and use the exposed adhesive layer to attach the controller to the patient for one treatment period (e.g., at night while the patient sleeps). The controller may be removed following the treatment period, and a new adhesive layer may be utilized each time the patient wishes to reattach the controller. In some instances, one or more portions of the release liner may be labeled to indicate which day of the week a specific adhesive layer should be removed.

It should be appreciated that in variations where a patch comprises multiple adhesive layers, each adhesive layer may comprise the same adhesive, or different layers may comprise different adhesives. Additionally or alternatively, each of the adhesive layers may be configured to last the same amount of time, or different adhesive layers may be configured to last for different amounts of time. Additionally, when a controller comprises multiple release liners covering multiple adhesive layers, it should be appreciated that removal of some or all of the release liners may activate one or more functions of the controller. In some of these variations, removal of each release liner may activate a function of the controller. For example, removal of a first release liner may initiate the generation of a first timed output signal, and removal of a second release liner may initiate the generation of a second timed output signal. In other variations, removal of some release liners may activate one or more controller functions, while removal of other release liners does not alter the controller function. For example, in some variations, removal of a first release liner may initiate the generation a first timed output signal, but removal of subsequent release liners does not affect operation of the controller.

Figure 17A:
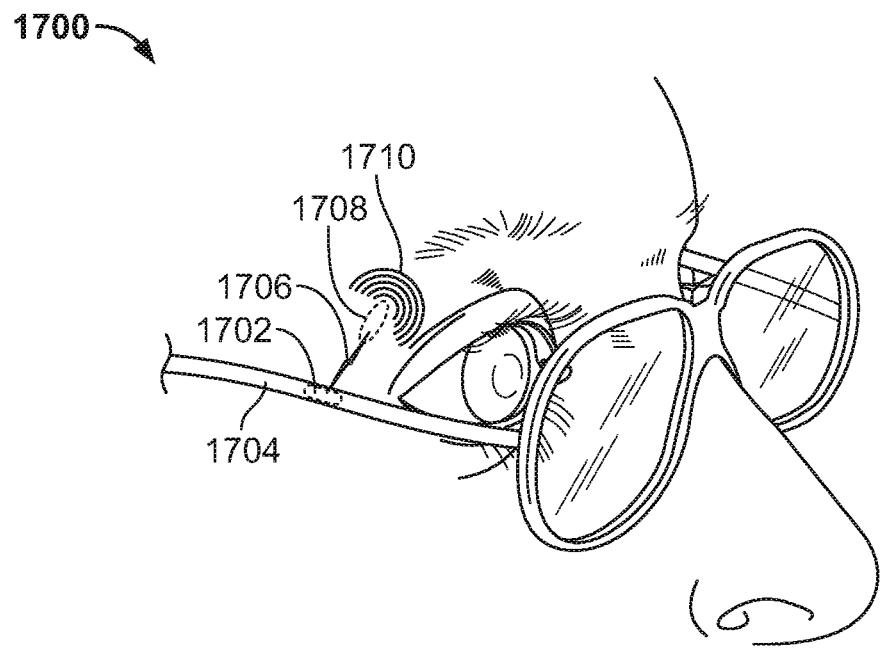
FIGS. 17A, 17B, 18, 19, 20, 21, 22, 23A and 23B depict variations of controllers suitable for use with the stimulation systems described here.
Figure 17B:
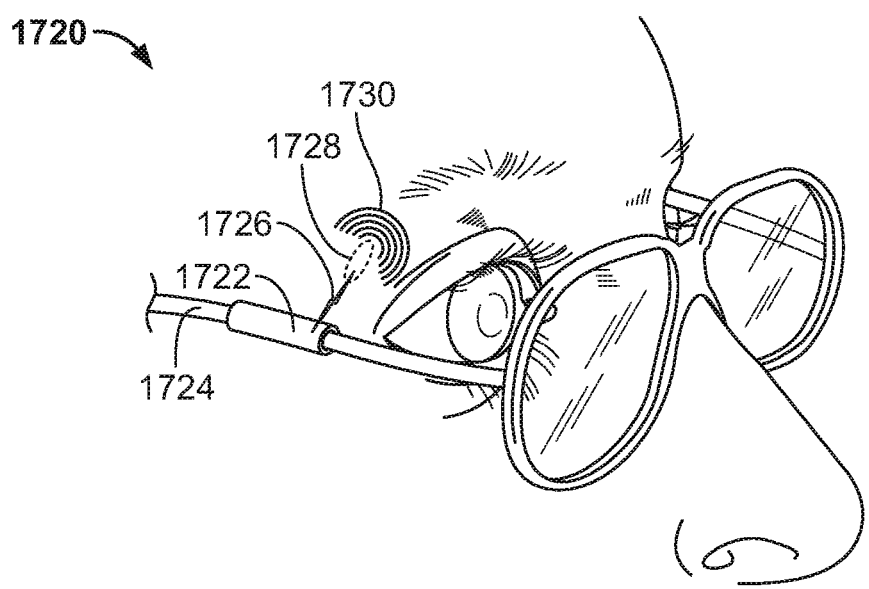

In some variations of the stimulation systems described here, a controller may be incorporated into a pair of eyeglasses. FIGS. 17A and 17B illustrate two such variations of controllers for use with the stimulation systems described here. FIG. 17A shows a stimulation system (1700) which includes a controller (1702) which is embedded within the frame of a pair of eyeglasses (1704). The controller (1702) may generate an output signal (1706) which may be received by an implanted microstimulator (1708). The implanted microstimulator (1708) may generate a stimulation signal (1710) used to stimulate an anatomical target, as described in more detail below. The controller (1702) may be embedded into any suitable portion of the eyeglasses (e.g., the frame, a nose piece, etc.).

While the controller (1702) shown in FIG. 17A is embedded within a pair of eyeglasses (1704), it should be appreciated that in some instances a controller may be attached to a pair of eyeglasses. For example, FIG. 17B shows another variation of a stimulation system (1720) comprising a controller (1722) which is attached to the frame of a pair of eyeglasses (1724). Controller (1722) may be temporarily or permanently attached to eyeglasses (1724), and may be attached in any suitable manner. In some variations, the controller (1722) may be attached to the pair of eyeglasses (1724) via one or more adhesives. In other variations, the controller (1722) may be configured to clip to or otherwise mechanically connect to the eyeglasses (1724). In some instances, the controller (1722) may be configured to slide over one or more portions of the eyeglasses (1724) In instances where a controller is releasably attached to a pair of eyeglasses, the controller can be replaced without needing to replace components of the eyeglass (1724). Additionally, if a patient wishes to switch between different pairs of eyeglasses (e.g., between un-tinted lenses and sunglasses), a releasably-attachable controller may be switched between the different eyeglasses. The controller (1722) may generate an output signal (1726), which may be received by an implanted microstimulator (1728). The implanted microstimulator (1728) may generate a stimulation signal (1730) which may be used to stimulate an anatomical target, as described in more detail below.

Figure 18:
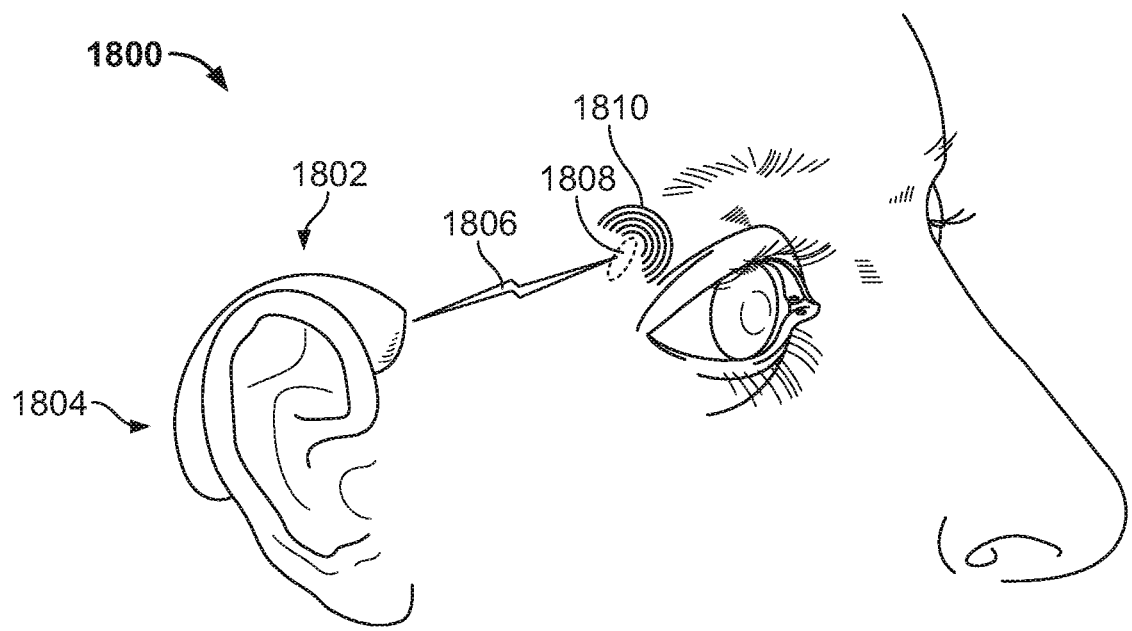

In other variations, a controller may be incorporated into a device which may be worn over or behind the ear of a user. For example, FIG. 18 shows one such example of a stimulation system (1800) comprising a controller (1802) which may be worn over the patient's ear near the mastoid region (1804) of the temporal bone. In some instances, the controller (1802) may comprise one or more adhesives to help hold the controller (1802) in place relative to the ear. The controller (1802) may generate an output signal (1806) which may be received by an implanted microstimulator (1808). The implanted microstimulator (1808) may generate a stimulation signal (1810) used to stimulate an anatomical target, as described in more detail below.

Figure 19:
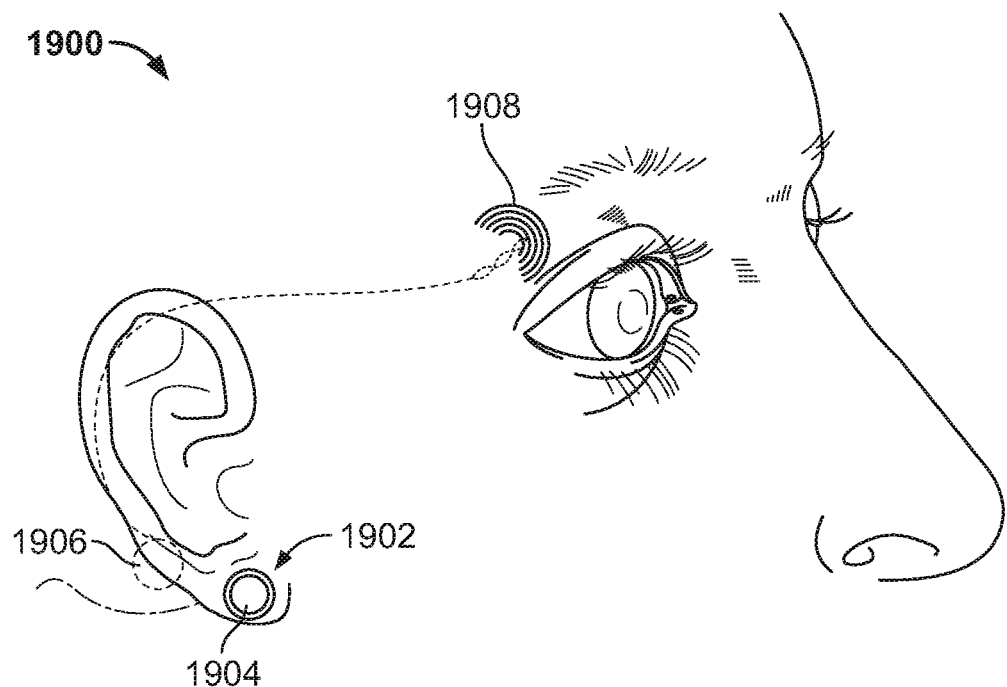

In still other variations, the controller may be attached to a portion of the ear itself. For example, FIG. 19 shows one such variation of a stimulation system (1900) that includes a controller (1902) comprising an earring (1904) which may be attached to the ear of a patient. The controller (1902) may generate an output signal (not shown) received by a portion of an implanted microstimulator (1906). The implanted microstimulator (1906) may generate a stimulation signal (1908) used to stimulate an anatomical target, such as the microstimulator (723) described above with respect to FIG. 7F.

Figure 20:
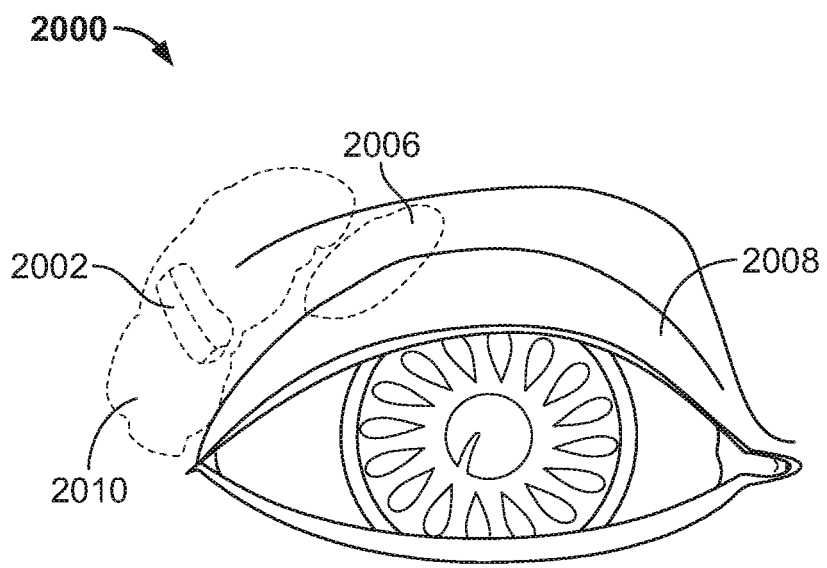

In some variations, a controller may be configured for placement in the fornix of an eye under the eyelid. For example, FIG. 20 shows one variation of a stimulation system (2000) that includes a microstimulator (2002) and an implantable microstimulator (2004) and a controller (2006) placed in the fornix under the upper eyelid (2008) of a patient. The controller (2006) may be flexible and/or conformable, and may be shaped to match or accommodate the curvature of the eyeball and/or fornix. In some variations, the controller (2006) may be rechargeable. In some variations, the controller (2006) may be disposable. While the microstimulator (2002) is shown in FIG. 20 as being positioned on the lacrimal gland (2010), it should be appreciated that a fornix-based controller may be used with a microstimulator positioned in any suitable location. In some variations, a fornix-based controller may be attached to or incorporated into a contact lens which may be worn by the patient. It should also be appreciated that one or more microstimulators may be configured for placement in the fornix.

Figure 21:
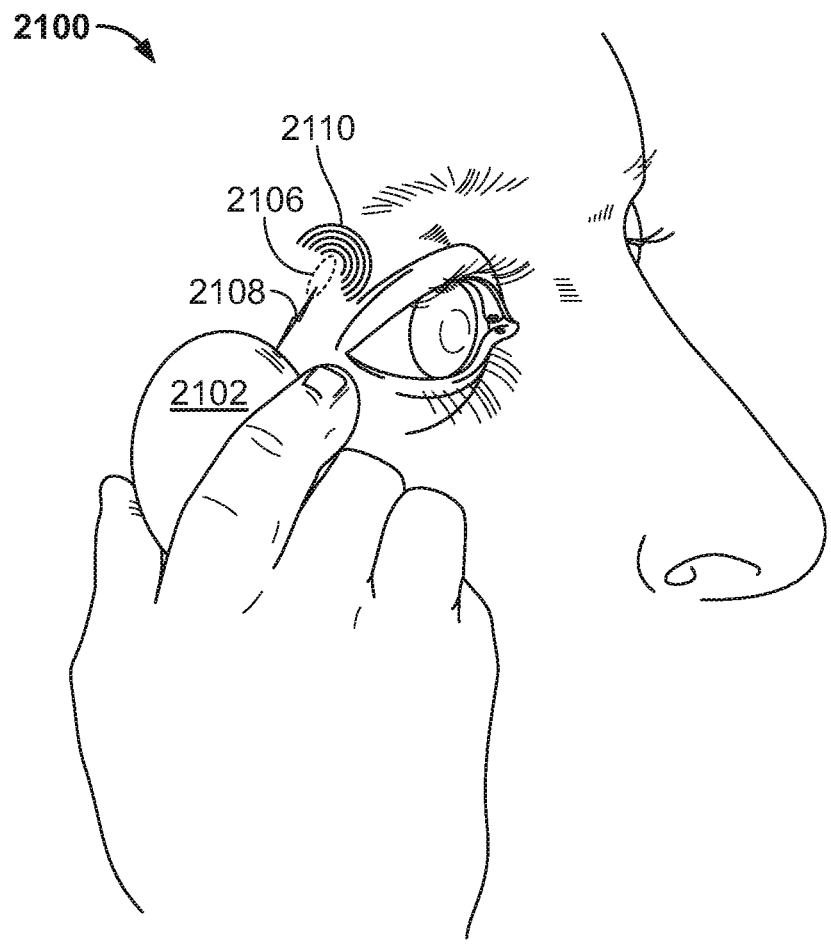

FIG. 21 depicts another exemplary external controller for use with the stimulation systems described here. As shown there, a stimulation system (2100) includes a controller (2102) comprising a hand-held device (2104). The controller (2102) may be brought to the vicinity of an implanted microstimulator (2106), and may produce an output signal (2108) received by the implanted microstimulator (2106). The implanted microstimulator may in turn generate a stimulation signal (2110) used to stimulate an anatomical target, as described in more detail below. The hand-held device may be configured as a key fob, a wrist watch, or another suitable structure.

Figure 22:
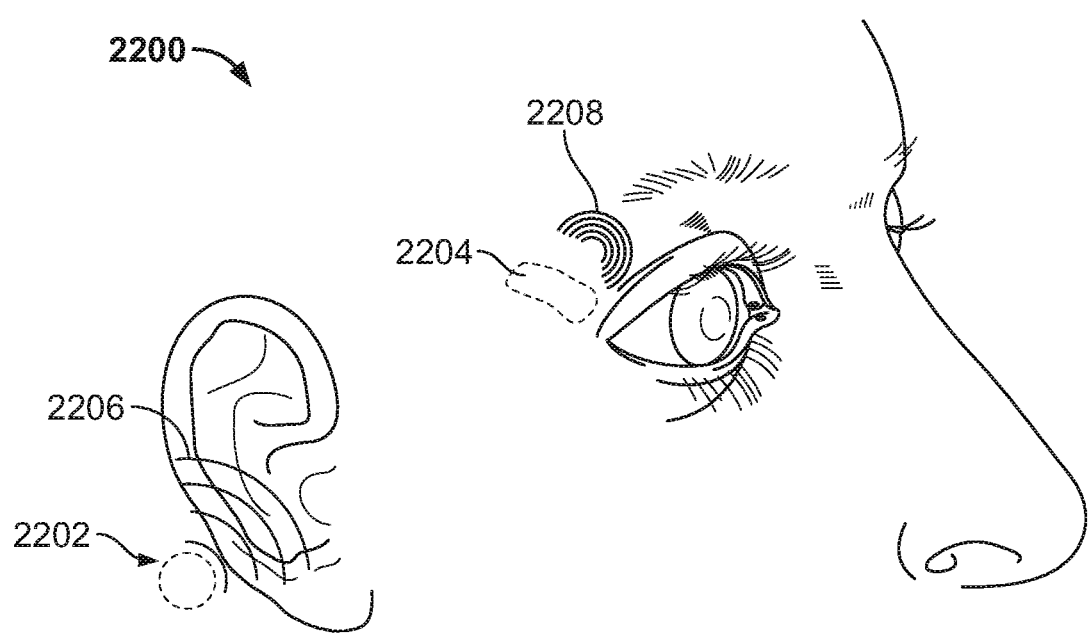

As mentioned above, some variations of the stimulation systems described here may comprise an implantable controller. For example, FIG. 22 depicts one variation of a stimulation system (2200) comprising an implantable controller (2202) and an implantable microstimulator (2204). Implantable controller (2202) may produce an output signal (2206), which may be received by the implantable microstimulator (2204). The implantable microstimulator (2204) may in turn generate a stimulation signal (2208) used to stimulate an anatomical target. In instances where the implantable microstimulator (2204) is implanted in a target location where space is limited, a remotely positioned implantable controller (2202) may allow for circuitry or other components to be implanted in a patient without having to be positioned at the target location. While the implantable controller (2202) is shown in FIG. 22 as being implanted in the head of a patient, it should be appreciated that the implantable controller (2202) may in any suitable location of the body (e.g., the head, neck, torso, or the like). It should be appreciated that in instances where a stimulation system (2200) comprises an implantable controller (2202), the stimulation system (2200) may comprise one or more external devices (such as one or more of the controllers described above) which may be configured to provide programming instructions to the implantable controller (2202) and/or may recharge the implanted controller (2202) in variations where the implanted controller (2202) comprises a rechargeable power source.

Figure 23B:
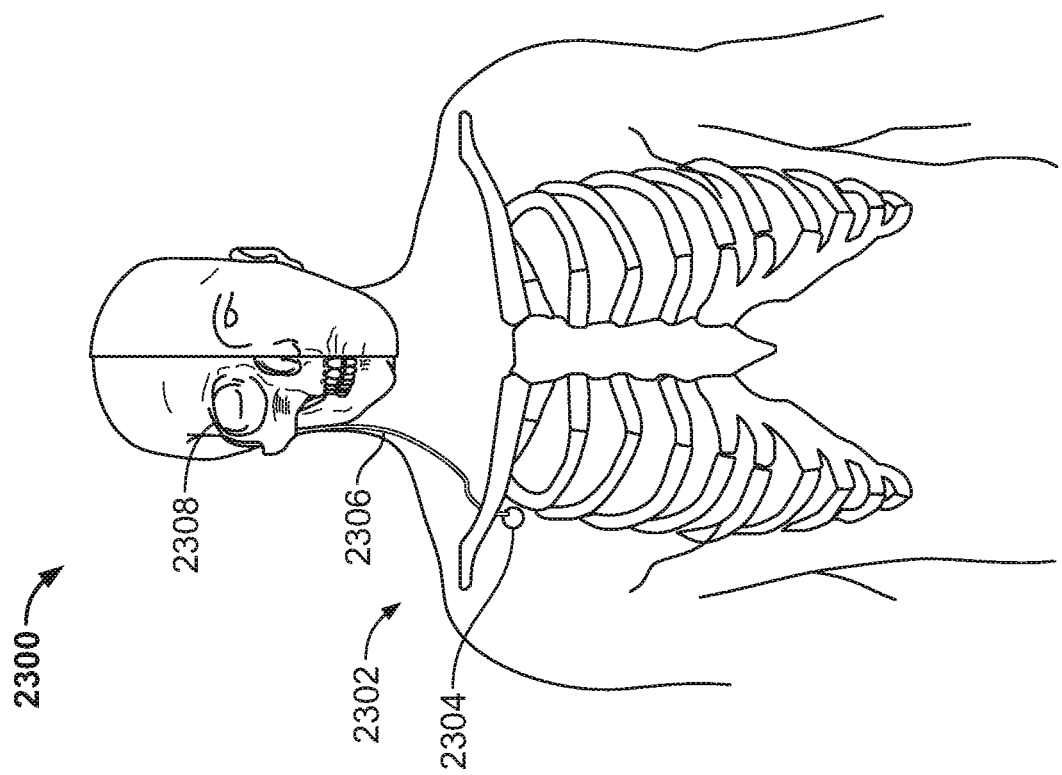
Figure 23A:
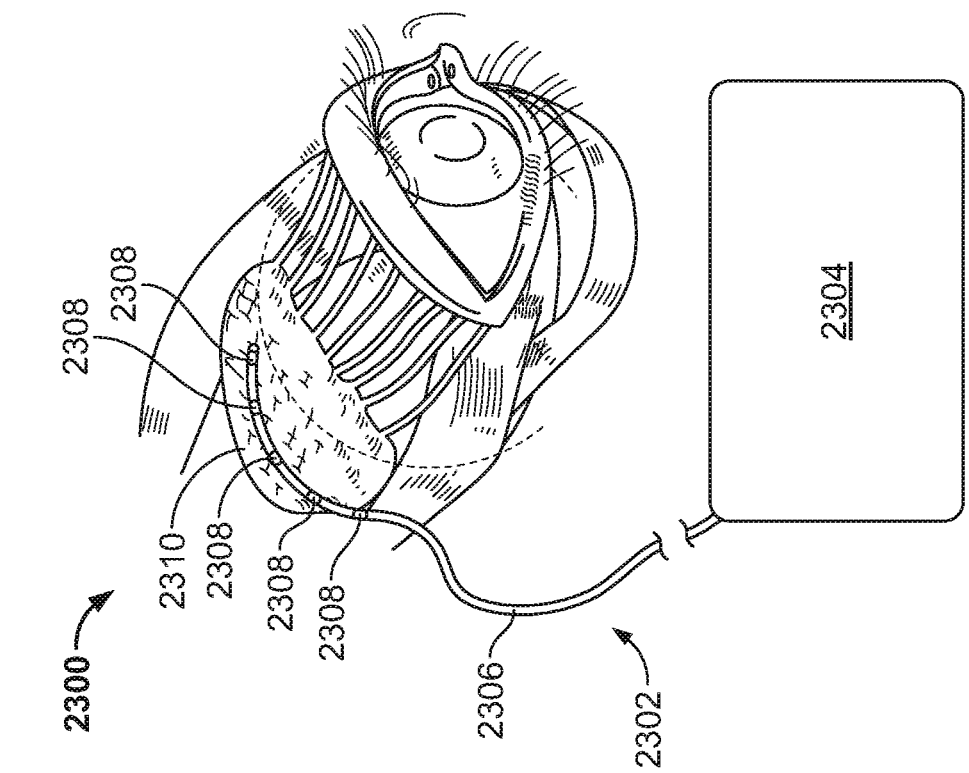

In still other variations, some or all of the controller components may be incorporated into an implantable stimulation device. For example, in some variations a stimulation device may comprise an implantable pulse generator with an internal power source. FIG. 23A depicts one variation of a stimulation system (2300) comprising an implantable microstimulator (2302). As shown there, the implantable microstimulator (2302) may comprise a pulse generator (2304) connected to a lead (2306) that comprises a plurality of electrodes (2308). The lead (2306) may be positioned such that the electrodes (2308) may be positioned adjacent to or in the lacrimal gland (2310), although it should be appreciated that the electrodes (2308) may be positioned near any suitable tissue as described in more detail below. The pulse generator (2304) may comprise one or more batteries or other power sources, and may be configured to produce one or more stimulation pulses or other signals that are applied to the electrodes to stimulate one or more desired anatomical targets. While shown in FIG. 23A as comprising a multi-electrode lead (2306), in some variations the stimulation device may comprise one or more monopolar electrode leads.

When an implantable stimulation device comprises an implantable pulse generator with an internal power source, the pulse generator may be implanted in any suitable location in the body. For example, FIG. 23B shows the stimulation system (2300) with the pulse generator (2304) implanted near a patient's clavicle bone. The lead (2306) may extend within the body of the patient from the pulse generator (2304) to a target location (e.g., the lacrimal gland). In other variations, the pulse generator (2304) may be positioned in the head or neck. It should be appreciated that in instances where a microstimulator (2302) comprises an implanted pulse generator (2304), the stimulation system (2300) may still comprise one or more external devices (such as those described above) which may be configured to provide programming instructions to the pulse generator (2304) and/or may recharge the pulse generator (2304) in variations where the microstimulator (2302) comprises a rechargeable power source.

As mentioned above, the controller may be configured to transmit one or more signals to an implanted microstimulator. In some variations, the output signal produced by the controller may provide power to the microstimulator. For example, in variations in which a stimulation system comprises a microstimulator having a passive stimulation circuit (or a stimulation circuit that does not otherwise include a battery or internal power supply), the controller signal may power the stimulation device. In variations in which a microstimulator of a stimulation system comprises a power source, the signal of the controller may temporarily provide power to the microstimulator to assist in microstimulator operation and/or to recharge the power supply of the microstimulator. In variations where a stimulation system comprises an implanted controller, an external controller may provide a signal to recharge or otherwise power the implanted controller.

In some variations, one or more of the signals produced by the controller may transmit information to one or more portions of the stimulation system. For example, in variations where a stimulation system comprises a microstimulator having an implantable pulse generator, the controller may provide programming instructions (e.g., stimulation parameters, stimulation times, etc.) to the implantable pulse generator. Similarly, in variations where a stimulation system comprises an in implanted controller, an external controller may be configured to provide one or more control signals or other information to the implanted controller. In variations where a microstimulator comprises an adjustable component, one or more output signals of the controller may be used to adjust the adjustable component.

Figure 30:
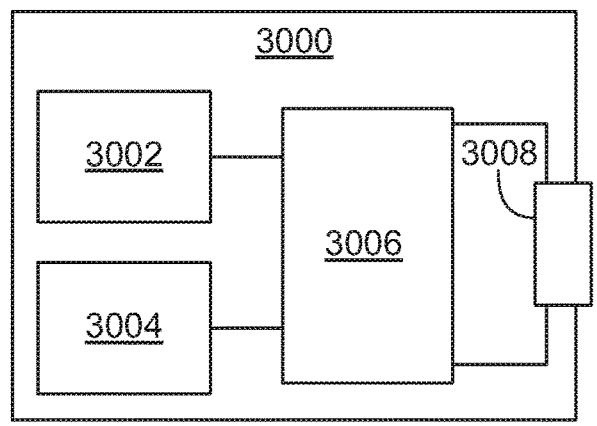
FIG. 30 depicts a block diagram of a variation of a controller suitable for use with the stimulation systems described here.

FIG. 30 depicts a schematic diagram of one variation of a controller (3000) circuit suitable for use with the stimulation systems described here. As shown there, the controller (3000) may include a power source (3002), an input module (3004), a controller (3006), and a transmission component (3008). The power source (3002) may provide a voltage or current to the controller (3006). The supplied power may be a constant voltage or current or an alternating voltage or current.

Input module (3004) may provide one or more inputs signals to controller (3006) based on input received from a user such as a patient, a health professional, or other external source. For example, the user input may be a depressed button, an input along a slide bar, or some other input that indicates whether to apply stimulation to one or more anatomical targets (such as a lacrimal gland), what type of stimulation to apply, and/or what stimulation parameters to apply. The input signals may also be generated from logic inside the input module (3004). For example, input module (3004) may include logic to apply stimulation to a lacrimal gland periodically, in a ramped fashion, continuously, in a patterned fashion, in response to detecting a condition of low or decreased tear production, or some other condition. In some variations the stimulation may be ramped to prevent activation of pain sensation.

Controller (3006) may receive power from power source (3002) and input signals from input module (3004) to generate an output signal. The output signal may be a voltage signal or a current signal applied to transmission element (3008). The output signal may vary in frequency, amplitude, period and/or phase based on the input received from input module (3004) and power received from controller (3002). The transmission element (3008) may be any element suitable for conveying energy and/or information to a microstimulator (not shown), such as one or more coils, ultrasound generators, optical energy generators, or the like. When the output signal is applied to a transmission element (3008) including a coil, the coil may generate a magnetic wave having a radio frequency and amplitude based on the output signal and coil. In some variations, the controller (3006) may detect one or more operating parameters of the microstimulator.

While the controller (3006) is shown in FIG. 30 as having an input portion, it should be appreciated that the controller need not have an input portion. FIG. 45A depicts a block diagram of another variation controller circuit (4500) comprising a power source (4502), a controller (4504), and a transmission portion (4506). As described in more detail above, the power source (4502) may provide power to the controller (4504). The controller (4504) may be programmed or otherwise configured to produce one or more output signals, which may be transmitted to a microstimulator via transmission portion (4506).

Figure 45B:
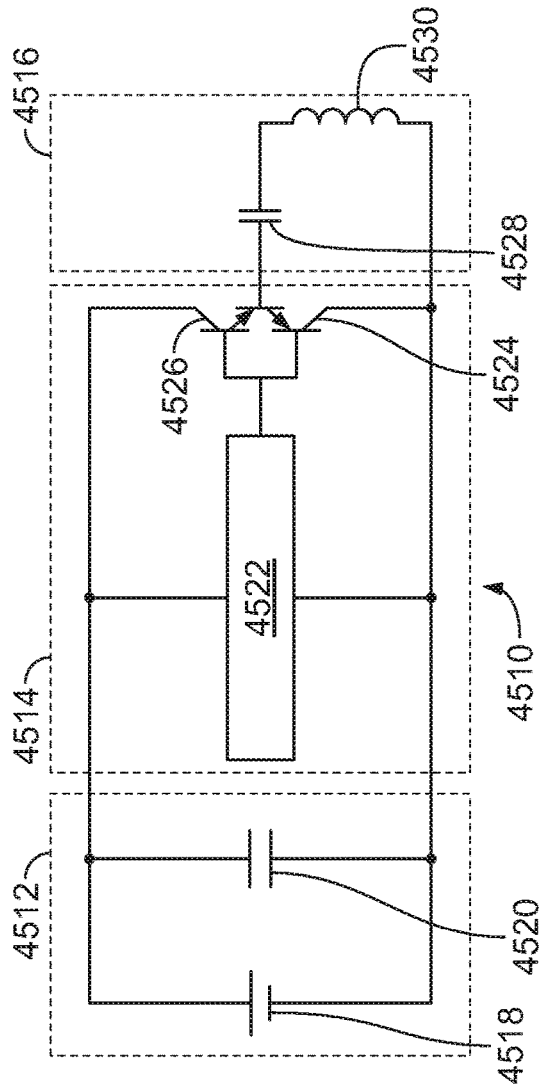
Figure 45A:
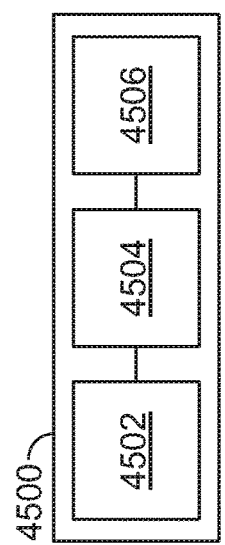

FIG. 45B depicts one variation of a controller circuit (4510) comprising a power source (4512), a controller (4514), and a transmission portion (4516) as described immediately above. As shown there, the power source (4512) may comprise a battery (4518) in parallel with a capacitor (4520), although it should be appreciated that the power source (4512) may include any suitable elements. In this variation, the battery (4518) may continuously charge the capacitor (4520), and the capacitor (4520) may provide current to the controller (4514) during generation of an output signal when the electrochemical reactions of the battery (4518) is not fast enough to provide the amount of current required to generate the output signal. The power source (4512) may or may not be rechargeable.

The power source (4512) may provide power to the controller (4514), which may generate an output signal. In the variation shown in FIG. 45B, the controller may comprise a pulse generator (4522), a first transistor (4526) and a second transistor (4524). The pulse generator (4522) may be connected to the first and second transistors such that current may flow through only the first transistor (4526) when the pulse generator (4522) is generating a pulse and may flow only through the second transistor (4525) when the pulse generator (4522) is not generating a pulse. This may allow for an alternating current to be generated in the transmission portion (4516). While shown in FIG. 45B as having a pulse generator (4522) connected to first and second transistors, it should be appreciated that the controller may comprise a pulse generator connected to an H-Bridge, a microcontroller, or the like.

The output signal produced by the controller (4514) may be transmitted to a microstimulator using transmission portion (4516). The transmission portion (4516) may comprise one or more coils, ultrasound generators, light sources, or the like which may transmit the output signal. For example, as shown in FIG. 45B, the transmission portion (4516) may comprise a tuning capacitor (4528) in series with a coil (4530). This circuit may be tuned such that the pulses generated by the controller (4514) are transmitted at a specific frequency (e.g., 1 Mhz, or the like).

Figure 46:
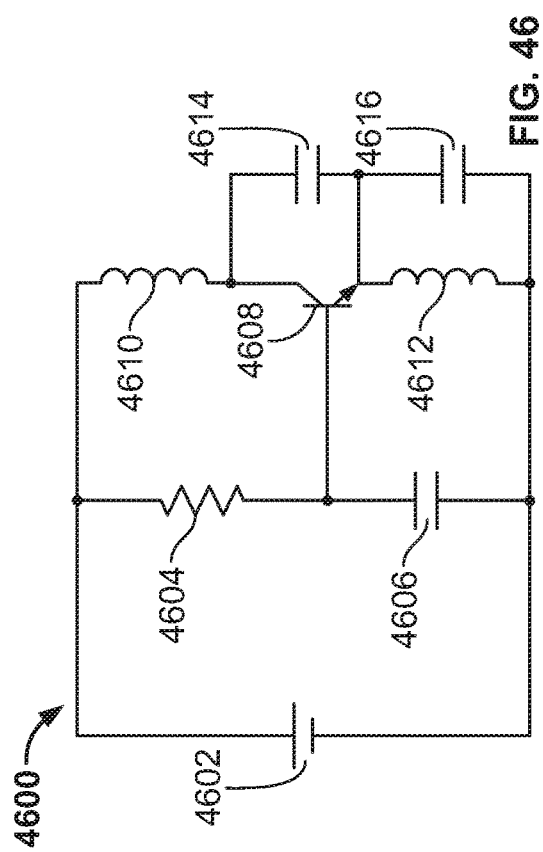
FIGS. 45A, 45B, and 46 illustrate variations of controller circuits suitable for use with the controllers described here.

FIG. 46 shows another variation of a controller circuit (4600) which may be used to generate a periodic oscillating output signal. As shown there, the controller circuit (4600) may comprise a voltage source (4602), a resistor (4604), a first capacitor (4606), a second capacitor (4614), a third capacitor (4616), a bipolar junction transistor (4608), a transmission coil (4610), and a choke (4612). The voltage source (4602) (e.g., a battery) may be connected in parallel with the resistor (4604) and the first capacitor (4606), and the base of the bipolar junction transistor (4608) may be connected between the resistor (4604) and the first capacitor (4606). A first end of the voltage source (4602) may also be connected to the transmission coil (4610). A second end of the voltage source (4602) may also be connected to the choke (4612) and the third capacitor (4616). The collector of the bipolar junction transistor (4608) may be connected to the transmission coil (4610) and the second capacitor (4614), and the emitter of the bipolar junction transistor (4608) may be connected to the second capacitor (4614), the third capacitor (4616), and the choke (4612).

When the voltage source (4602) is connected to the controller circuit (4600), the voltage source (4602) may charge the first capacitor (4606) until the bipolar junction transistor (4608) begins to conduct. While the bipolar junction transistor (4608) is conducting, an oscillating signal may be passed through the transmission coil (4610) to produce an oscillating magnetic field. The frequency of the oscillating output signal may be determined by the inductance value of the transmission coil (4610) and the capacitance values of the second (4614) and third (4616) capacitors. The choke (4612) may provide DC-biasing during generation of the oscillating output signal. The oscillating signal may continue until the first capacitor (4606) has discharged through the bipolar junction transistor (4608) and the bipolar junction transistor (4608) stops conducting. At this point, the voltage source (4602) may recharge the first capacitor (4606), thereby repeating the production of the oscillating output signal. In this way, the oscillating signal may be continually produced at set intervals until the voltage source (4602) is disconnected or otherwise depleted. The resistance of the resistor (4604) may determine the rate at which first capacitor (4606) charges, which may determine the delay between subsequent administrations of the oscillating output signal. In some variations, the resistor (4604) may be adjustable to vary the delay. Additionally, the capacitance of the first capacitor (4606) may at least partially determine the duration of the oscillating output signal. In some variations, the first capacitor (4606) may be adjustable to vary the oscillating output signal duration.

The voltage source (4602) may be selectively connected to the controller circuit to determine when the oscillating output signal is produced by the controller circuit (4600). For example, in variations where the controller circuit (4600) is incorporated into a patch having a release liner, such as described in more detail above, removal of the release liner may connect the voltage source (4602) to the controller circuit (4600) (or otherwise complete the circuit) to initiate the periodic generation of the transmission signal. In these variations, the voltage source (4602) may comprise one or more batteries which may power the controller circuit (4600) for a set period of time (e.g., about four hours, about eight hours, or the like). In other variations, the controller may be configured to disconnect the voltage source (4602) after a set period of time (or upon some input from a patient). In some variations, the controller may comprise one or more controllers and/or user inputs which may control the connection of the voltage source (4602) to the controller circuit (4602).

In some variations, a controller may be configured to output a signal independent of any feedback from an implanted microstimulator (or another controller). For example, in some variations, a controller may be configured to produce a pre-set signal for a pre-set amount of time when the controller is activated (e.g., by depressing a button on the controller, removing a release liner from an adhesive layer, or the like). In some variations, as will be described in more detail below, the pre-set signal may be modified by user input.

In other variations, a controller may be configured to alter its output in response to feedback received from an implanted microstimulator. In some instances, a controller may be configured to alter its output based on feedback to account for misalignment or other movement between the controller and the microstimulator. For example, in some variations, the implanted microstimulator may be configured to transmit to the controller information regarding the strength of the signal received by the microstimulator, and the controller may be configured to alter its output in response to the received information. In other variations, the controller may be configured to detect and measure a load positioned within a field produced by the controller, and may alter the strength of the produced field as a function of the measured load. Additionally or alternatively, the controller may be configured to receive one or more signals measured from the patient (e.g., a signal indicative of dryness of the eyes), and may be configured to alter the output of the controller in response to the measured signal. In variations where the implanted microstimulator comprises one or more adjustable/tunable components, altering the output of the microstimulator may comprise adjusting the adjustable components.

In still other variations, it may be desirable to allow for a patient to alter the intensity of stimulation by increasing or decreasing the output strength of the controller. In some variations, a controller may comprise one or more buttons, sliders, levers, knobs, or other mechanisms a patient may manipulate to alter the output strength of the controller. In other variations, a stimulation system may comprise one or more external programmers which may be used to alter the output of the controller. For example, the hand-held controller (2102) described above in relation to FIG. 21 may be configured to communicate with and provide programming instructions to one or more other controllers (e.g., an implanted controller).

In some variations, a controller may comprise one or more safety elements. For example, in some variations a controller may comprise a temperature sensor which measures the temperature inside the controller. In these variations, the controller may be configured to shut down when the temperature inside the controller exceeds a certain threshold. This may prevent the controller from reaching a temperature which may injure a patient (e.g., when the patient is holding the controller, when the controller is attached to the patient, etc.).

In some variations, a stimulation set may comprise a plurality of controllers, wherein each controller is configured to produce a different output signal. FIG. 24 shows one variation of a controller set (2400), which comprises a plurality of individual controllers. As shown there, controller set (2400) comprises a first controller (2402), a second controller (2404), a third controller (2406), and a fourth controller (2408), although it should be appreciated that a controller set (2400) may comprise any suitable number of controllers. The controllers of the controller set (2400) may be configured to generate output signals having different stimulation parameters (e.g., pulse width, stimulation duration, etc.), such that a patient may select a specific controller to achieve a certain physical effect. For example, the first controller (2402) may be configured to generate an output signal having a longer pulse width than an output signal generated by the second controller (2404), and the second controller (2404) may be configured to generate an output signal having a longer pulse width than an output signal generated by the third controller (2406). A patient may use the second controller (2404) to provide a stimulation signal to an implantable microstimulator. If the stimulation is too intense for the patient, the patient may switch the second controller (2404) for the third controller (2406) (or the fourth controller (2408), which may produce a weaker stimulation signal than the third controller (2406)). Conversely, if the stimulation provided by the second controller (2404) does not achieve the desired physical effect, the patient may switch the second controller (2404) for the first controller (2402).

In some instances, it may be desirable to deliver a particular stimulation signal to a patient for a predetermined amount of time. Accordingly, it may be desirable to configure the stimulation system to provide a controlled "dose" of stimulation to a patient. For example, it may be desirable to configure a stimulation system to provide stimulation for a set period of time (e.g., four hours, eight hours, twelve hours or the like). Accordingly, the controllers described here may be configured to generate an output signal for a predetermined period of time, which may result in the generation of a corresponding stimulation signal by a microstimulator implanted in the patient.

In variations where a controller comprises a patch having an adhesive layer covered by a release line, such as those described in more detail above, the removal of the release liner may initiate a dose of stimulation therapy. In variations where a stimulation system comprises a microstimulator having a passive stimulation system, the stimulation therapy may comprise generating and transmitting an output signal to a microstimulator, as described in more detail above. In variations where a stimulation system comprises a microstimulator having an implantable pulse generator, the stimulation therapy may comprise delivering one or more signals to the implantable pulse generator instructing the microstimulator to deliver stimulation to tissue. The controller may continue to output the signal or signals for the duration of the dose of stimulation therapy. In some instances, the controller may be programmed to shut down or otherwise cease producing signals after a set period of time. In other instances, a power source of the controller may only have sufficient charge to power the controller for the duration of the dose of stimulation therapy.

In variations where a patch controller has a plurality of adhesive layers separated by release liners, removal of each release liner may begin a different dose of stimulation therapy. For example, it may be desirable for a patient to receive one dose of stimulation therapy each day. To begin a stimulation dose on the first day, a patient may remove a first release liner from a first adhesive layer and may affix the controller to a skin surface via the first adhesive layer. Removal of the first release liner may initiate a first dose of stimulation therapy, which may be delivered to the patient while the controller is affixed thereto. The patch may be removed from the patient following administration of the first dose. On the next day, the patient may remove a second release liner from a second adhesive layer (which may initiate a second dose of stimulation therapy), and may reaffix the controller to the skin surface to allow for delivery of the second dose of stimulation therapy. This may be repeated until each of the adhesive layers of the patch controller has been used, or until the patient has administered a prescribed number of doses.

In other variations, a plurality of disposable controllers may be used to deliver a plurality of doses of stimulation therapy. For example, FIGS. 25A and 25B show a side view and a top view of a controller set (2500) which may be used to deliver a plurality of doses of stimulation therapy. As shown there, controller set (2500) may comprise a plurality of stacked patch controllers (2502) attached to a base (2504). Each patch controller (2502) may comprise a tab (2506) or other structure which may aid in removal of that controller from the stack. In some instances, one or more portions of each controller (2502) (e.g., the tab (2506)) may be labeled with a time or day for intended use of that controller (2502), and that controller (2502) may be configured to provide an output signal configured to provide a desired treatment for the time or day of intended use. For example, a set of seven controllers may be labeled Monday through Sunday. The stack of controllers (2502) may be configured such that removal of a controller from the stack activates the controller (2502) to direct the delivery of a dose of stimulation therapy (e.g. initiates generation of an output signal). Removal of the controller from the stack may also expose an adhesive layer that may be used to affix the patch controller to a skin surface of the patient. After the controller has completed its dose of stimulation therapy, the controller may be removed and discarded, and a new controller may be removed from the stack when it is desired to deliver a new dose of stimulation therapy.

While the controller set (2500) shown in FIGS. 25A and 25B comprises a stack of controllers, it should be appreciated that in some variations the plurality of disposable controllers need not be directly connected. For example, FIG. 26 shows another variation of a controller set (2600) in which a plurality of patch controllers (2602) are each attached to a base (2604). Each of the controllers (2602) may be configured to activate when removed from the base (2604) to direct the delivery of a dose of stimulation therapy, and may be affixed to a patient via an adhesive layer that becomes exposed when the controller (2602) is removed from the base (2604). In some of these variations, the controller set (2600) may comprise controllers (2602) that are configured to provide different doses of stimulation therapy. For example, some controllers of the set may be configured to provide different stimulation strengths and/or stimulation durations, such that a user may select a specific controller from the controller set (2600) depending on the desired stimulation.

As mentioned above, the controllers described here may be disposable, or may be reusable. In some variations, the controller may be configured to prevent tampering or other modification of device components. For example, in some variations one or more components of the controller (e.g., a battery, a coil, or the like) may be welded to or otherwise integrally formed within the controller body such that accessing and/or removing one or more of these components may disable functionality of the device. This may prevent a user from improperly trying to replace or modify one or more components of the controller. In some variations, the controller may be configured such that one or more components of the controller is disposable, while one or more components of the controller is reusable. For example, in some variations a controller may be configured such that one or more components of the controller, such as a battery, adhesive layer, or coil, may be replaced without needing to replace the entire controller.

Methods

Also described here are methods for stimulating tissue. In some variations, one or more of the stimulation systems described here may be used to deliver stimulation to one or more anatomical targets. Generally, a microstimulator of the stimulation system may be implanted within the patient, and may be used to generate a stimulation signal which is applied to tissue (e.g., via one or more electrodes). In some variations, the microstimulator comprises a passive stimulation circuit, and the stimulation signal is passively generated from an output signal generated by a controller. The stimulation systems and associated methods may be used to treat one or more conditions. In some variations, the stimulation systems may be configured to treat one or more ocular conditions. For example, the stimulation systems described here may be configured to treat dry eye.

Figure 27A:
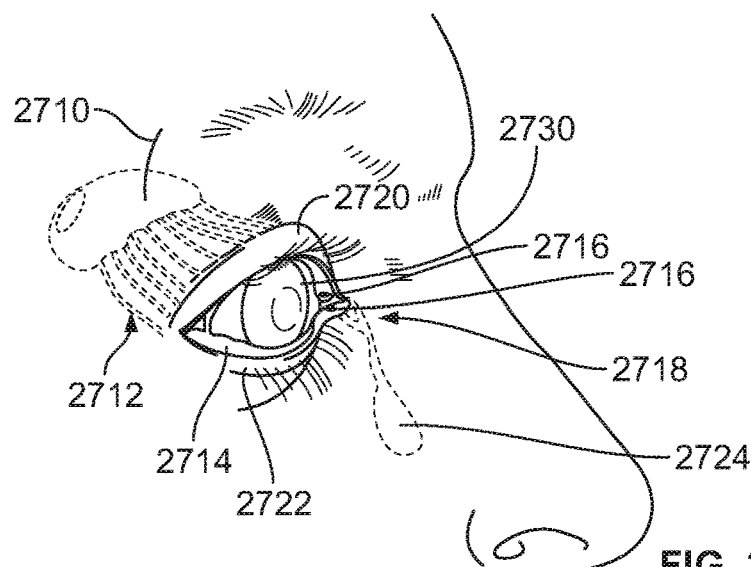
FIGS. 27A and 27B are perspective views of the lachrymal apparatus.

For the purposes of illustration, FIGS. 27A-27D depict various views of the anatomy of the head of a patient. FIG. 27A illustrates the lacrimal (or lachrymal) apparatus, the physiological system that contains the structures of the orbit for tear production and drainage. Shown there is an eye (2730) having an upper lid (2720) and a lower lid (2722). The lacrimal apparatus includes a lacrimal gland (2710), ducts (2712), puncta (2716), lacrimal ducts (2718), and nasolacrimal duct (2724). The lacrimal gland (2710) may be innervated by several nerves. These nerves may include the rami lacrimales, the lacrimal nerve, perivascular nerves of lacrimal artery, and sympathetic nerves fibers and neurites which innervate the lacrimal gland and its associated vasculature. The lacrimal gland (2710) may secrete lacrimal fluid (i.e., tears) (2714) which may flow through the ducts (2712) into the space between the eye (2730) and the upper (2720) and lower (2722) lids. When the eye (2730) blinks, the lacrimal fluid (2714) may be spread across the surface of the eye (2730). The lacrimal fluid (2714) may collect in the lacrimal lake (not shown), and may be drawn into the puncta (2716) by capillary action. The lacrimal fluid (2714) may flow through lacrimal canaliculi (not shown) at the inner corner of the upper (2720) and lower (2722) lids to enter the lacrimal ducts (2718) and drain through to the nasolacrimal duct (2724). The lacrimal fluid may drain from the nasolacrimal duct (2724) into the nasal cavity of the patient.

Figure 27B:
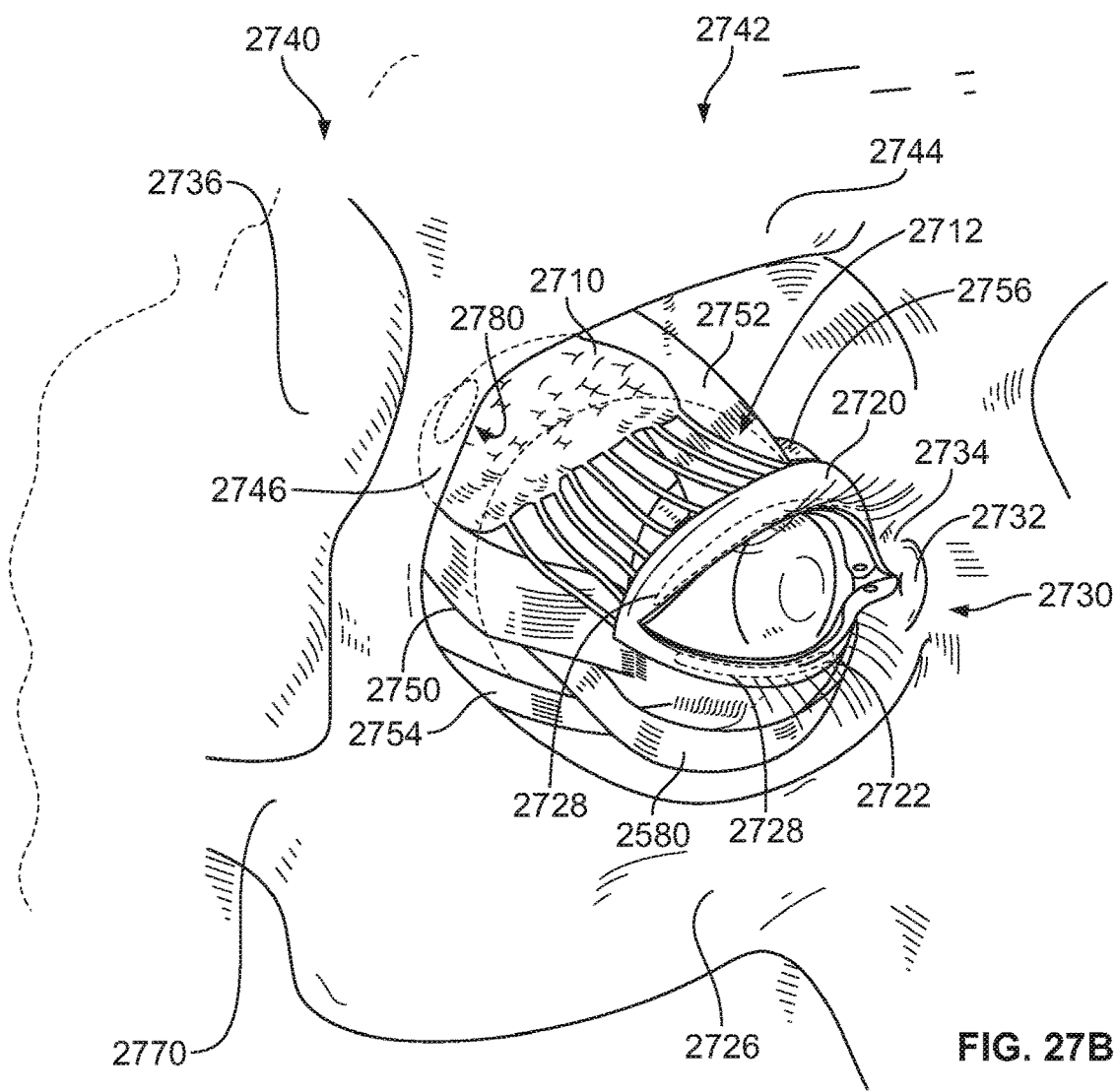

FIG. 27B illustrates additional anatomical structures around the lacrimal apparatus. As shown there, the rim of the upper lid (2720) and the lower lid (2722) contain meibomian glands (2728). The meibomian glands (2728) are sebaceous glands responsible for the supply of meibum (an oily substance that includes lipids and slows evaporation of the eye's tear film). Also shown in FIG. 27B is the posterior lacrimal crest (2734), which is a vertical ridge that divides the orbital surface of the lacrimal bone into two parts. In front of the posterior lacrimal crest (2734) is a longitudinal groove which unites with the frontal process (2746) of the skull (2740).

There are two bony depressions in the orbital cavity that may be referred to as the lacrimal fossa. The first is a smooth, concave shallow depression located on the inferior surface of each orbital plate of the frontal bone. This depression houses the lacrimal gland and is referred to as the "fossa for the lacrimal gland" (2730). The second is a smooth, more deeply concave depression on the lacrimal bone, which forms the medial wall of the orbital cavity. This depression houses the lacrimal sac and is referred to as the "fossa for the lacrimal sac" (2732).

The supraorbital process (2744) is a passage in the frontal bone for the supraorbital artery and nerve. The supraorbital process (2744) is located on the superior and medial margin of the orbit in the frontal bone. The orbit of the skull (2740) is lined with a periosteum (not shown) and contains the eye (2730), extraocular muscles for movement of the eye (2730), veins (not shown), arteries (not shown), and nerves (not shown) which traverse the orbit into the face and the lacrimal gland (2710).

The extraocular muscles include the lateral rectus (2750), the medial rectus (not shown), the superior rectus (2752), inferior rectus (2754), superior oblique (2756), inferior oblique (2758), and the levator palpebrae superioris (not shown). The lateral rectus (2750) abducts the eye away from the nose and the medial rectus adducts the eye towards the nose. The lateral rectus (2750) and the medial rectus move the eye only in a horizontal plane. The superior rectus (2752), inferior rectus (2754), superior oblique (2756), and inferior oblique (2758) control vertical motion. The levator palpebrae superioris originates on the sphenoid bone (2736) and is responsible for elevating the upper lid (2720). The malar process (2726) is a rough projection from the maxilla (not shown) that articulates with the zygomatic bone (2770).

Figure 27D:
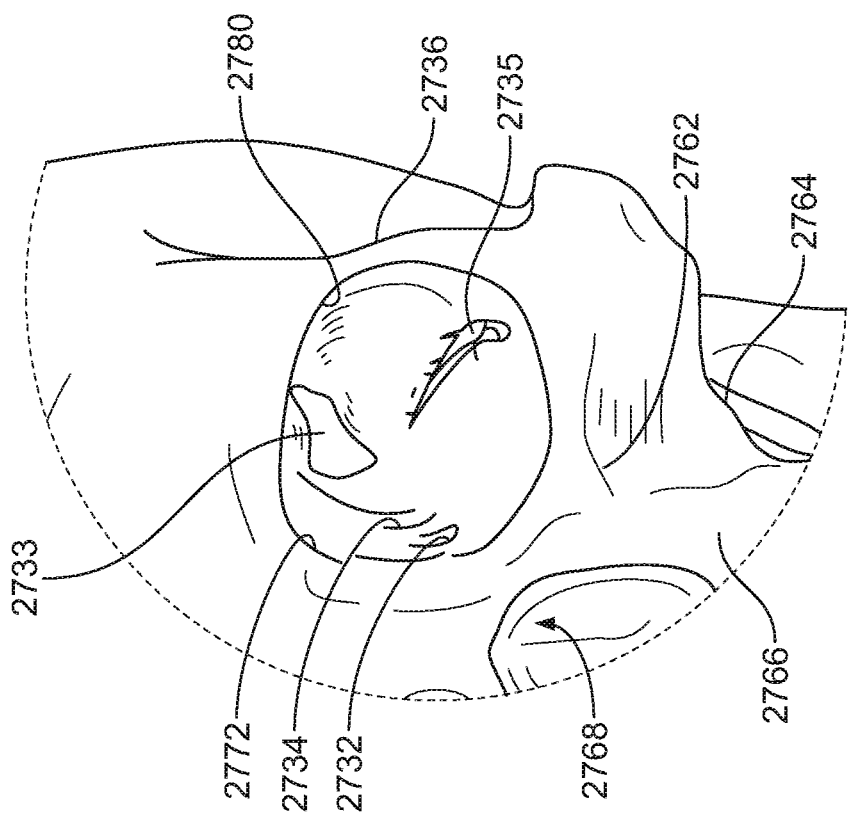
FIGS. 27C and 27D are front views of the skull of a patient.
Figure 27C:
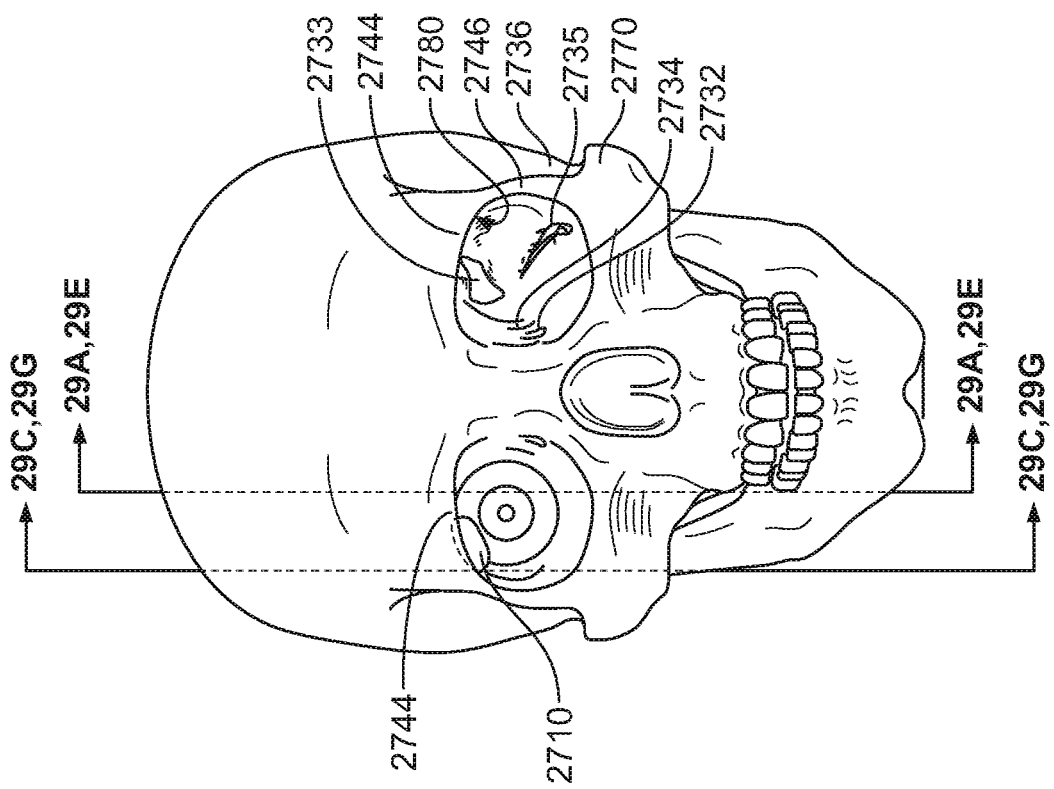

FIG. 27C shows a front view of the skull, and emphasizes the anatomy of the orbit with respect to the bones of the skull (2740). FIG. 27D shows an enlarged view of the left orbit of the skull (2740). As shown there, the exterior to the orbit includes the posterior lacrimal crest (2734), the supraorbital process (2744), the frontal process (2746), the sphenoid bone (2736), and the zygomatic bone (2770). The interior of the left orbit includes the superior orbital fissure (2733), inferior orbital fissure (2735), the fossa for the lacrimal gland (2780) and the fossa for the lacrimal sac (2732). The structures that enter the orbit through the superior orbital fissure 33 include the cranial nerves (CN) III, IV, and VI, lacrimal nerve, frontal nerve, nasociliary nerve, orbital branch of middle meningeal artery, recurrent branch of lacrimal artery, superior orbital vein, and the superior ophthalmic vein. The structures that enter the orbit through the inferior orbital fissure 35 include the infraorbital nerve, zygomatic nerve, parasympathetics to the lacrimal gland, infraorbital artery, infraorbital vein, and inferior ophthalmic vein branch to pterygoid plexus.

Figure 28:
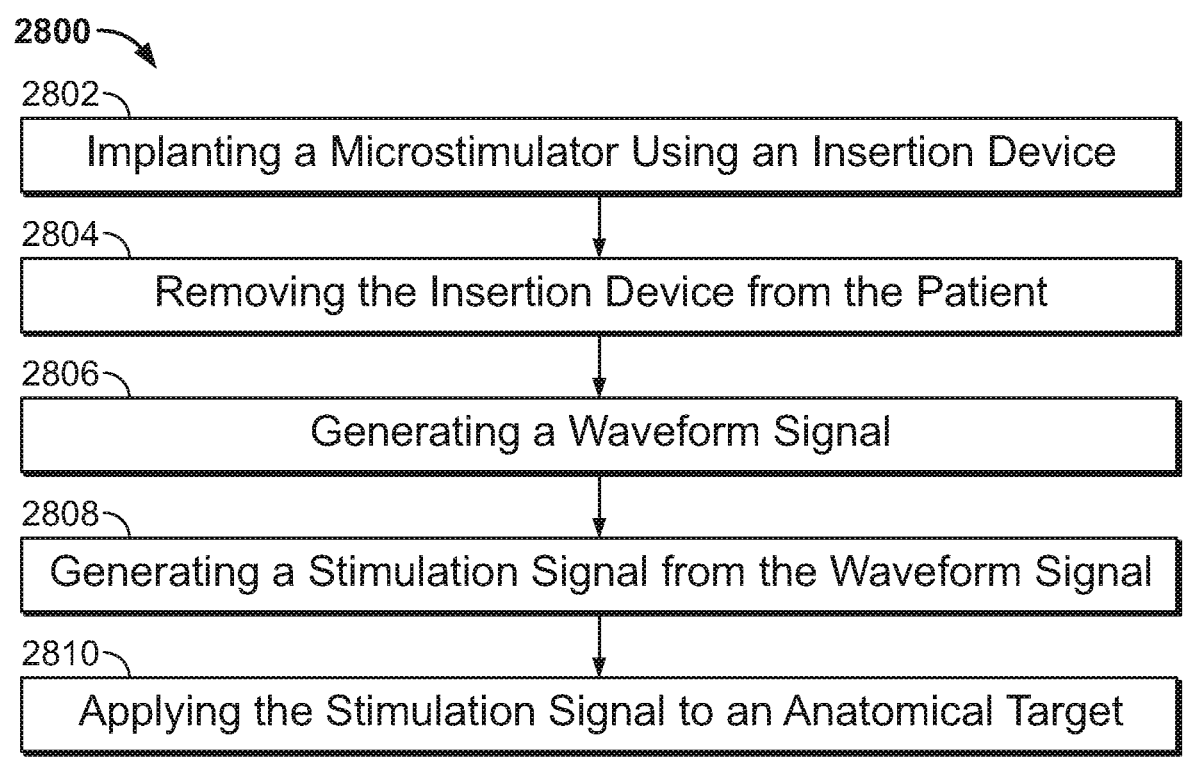
FIG. 28 depicts a flow chart of a stimulation method described here.

FIG. 28 depicts a flow chart of a method for stimulating an anatomical target using the stimulation systems described here. This method may be used to treat dry eye, or one or more other conditions as described in more detail below. First, a microstimulator may be implanted using an insertion device at step (2800). The microstimulator may be any suitable microstimulator, such as one or more of the microstimulators described in more detail above. The microstimulator may comprise a passive stimulation circuit, but need not. In variations where the microstimulator comprises a passive stimulation circuit, the passive stimulation circuit may comprise a ramping control unit which may passively ramp a stimulation signal produced by the passive stimulation circuit, as described in more detail below.

The insertion device may be removed from the patient at step (2802). A waveform signal may be generated at step (2804). The waveform signal may be generated as an output signal of a controller. The waveform may be generated automatically based on closed loop control or based on user input received by the controller. A stimulation signal may be generated from the waveform signal at step (2806). The stimulation signal may be generated by a microstimulator based on the output signal generated by the controller and received by the microstimulator. The stimulation signal may then be applied to the anatomical target at step (2808).

When implanting a microstimulator as mentioned in relation to step (2800), the microstimulator may be implanted at any suitable location relative to the body. In some variations, the microstimulator may be implanted in the orbit of the skull adjacent to the eye. In some variations, the microstimulator may be implanted into about, in proximity to, within or partially in the lacrimal gland. In some variations, the microstimulator may be implanted into the fossa for the lacrimal gland. In instances where the microstimulator is used to treat dry eye, the microstimulator may be used to stimulate one or more nerves that innervate the lacrimal gland tissue, as will be described in more detail below.

Figure 29A:
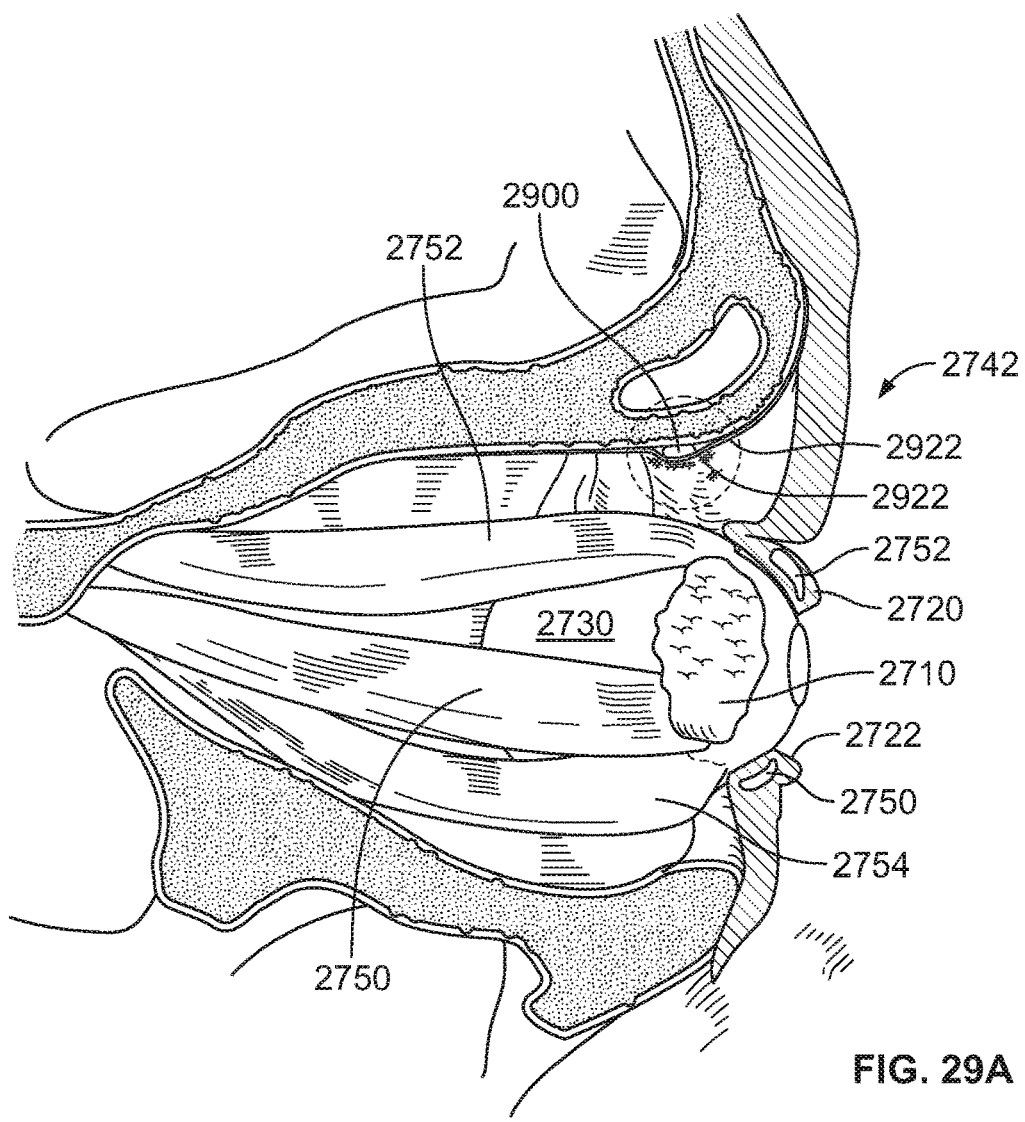
FIGS. 29A-29H depict different implantation locations for the microstimulators described here.

FIGS. 29A-29H depict different implantation locations which may allow a microstimulator to stimulate the lacrimal gland (e.g., for the treatment of dry eye). FIG. 29A shows a medial view of an eye within the orbit of a patient's skull.

The view of FIG. 29A corresponds to the view line 29A illustrated in FIG. 27C. Specifically, FIG. 29A includes the eye (2730) with upper lid (2720) and lower lid (2722), superior rectus (2752), lateral rectus (2750), inferior rectus (2754), and the lacrimal gland (2710) of FIG. 27C. Also shown there is the orbital process (2742) of the zygomatic bone, which is a thick, strong plate, projecting backward and medialward from the orbital margin.

As shown in FIG. 29A (and in an enlarged view in FIG. 29B), a microstimulator (2900) may be positioned between the portion of the bone forming the fossa for the lacrimal gland (2780) and the periosteum (2922). The periosteum (2922) of the orbit of a healthy eye may be tightly attached. In cases of a diseased eye, the periosteum (2922) may be loosely attached and raised from the bone beneath.

Figure 29B:
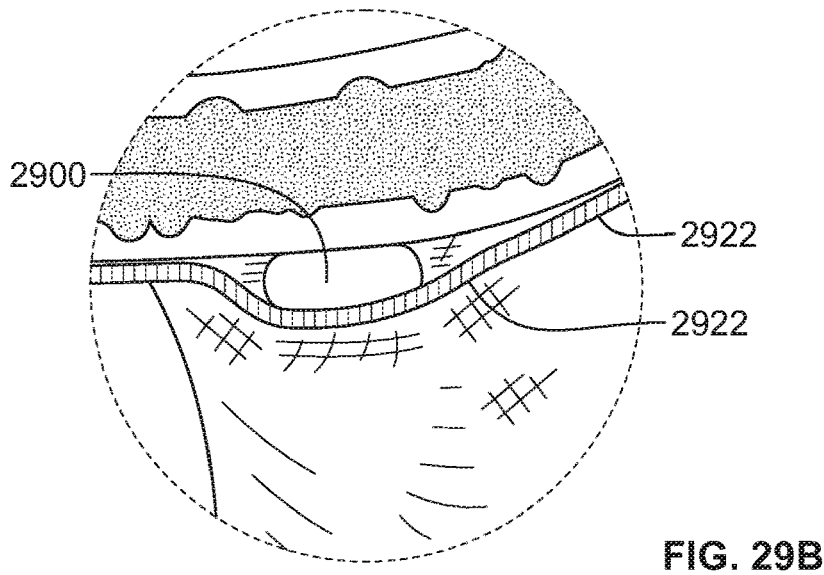
Figure 29C:
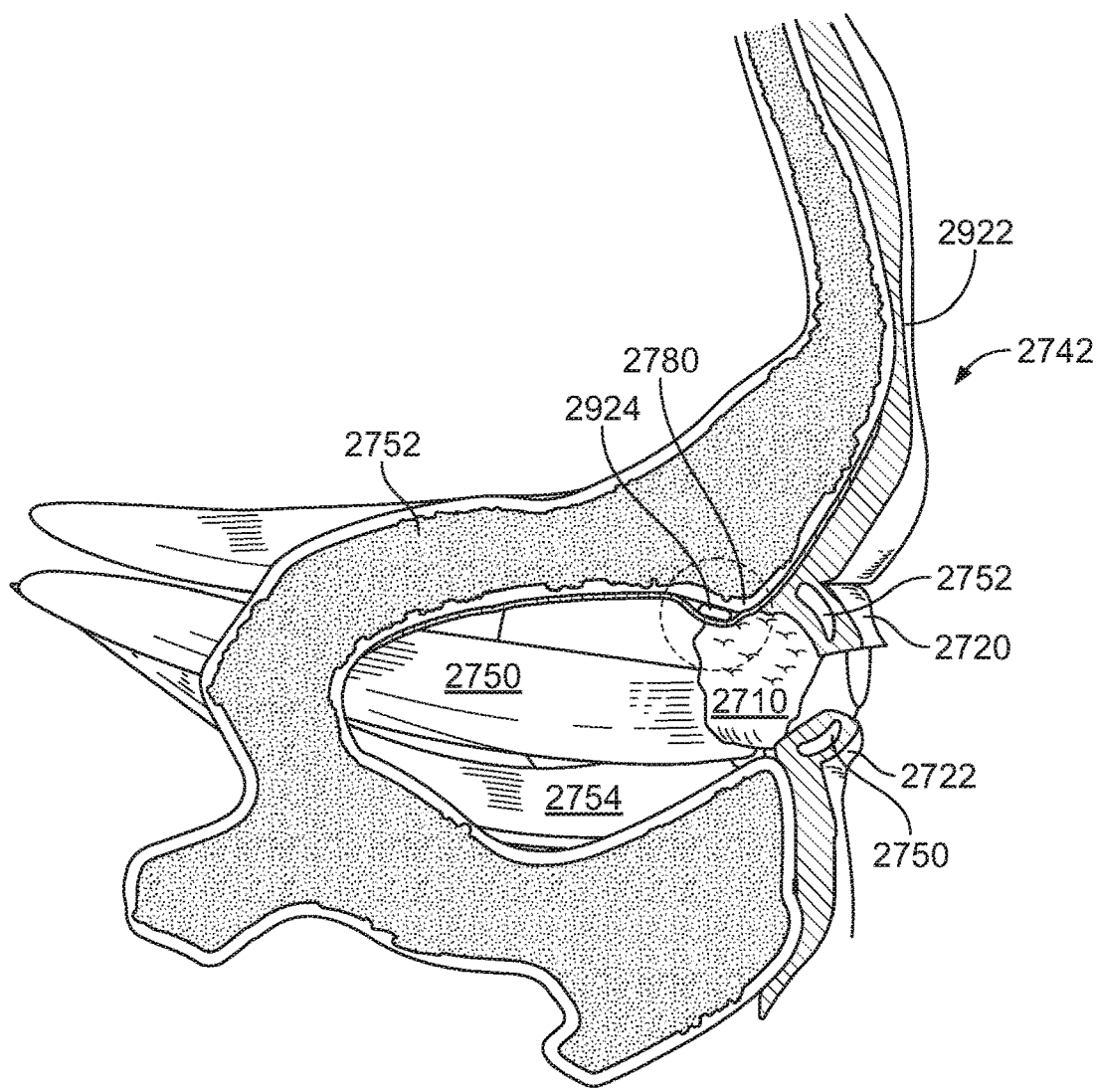
Figure 29D:
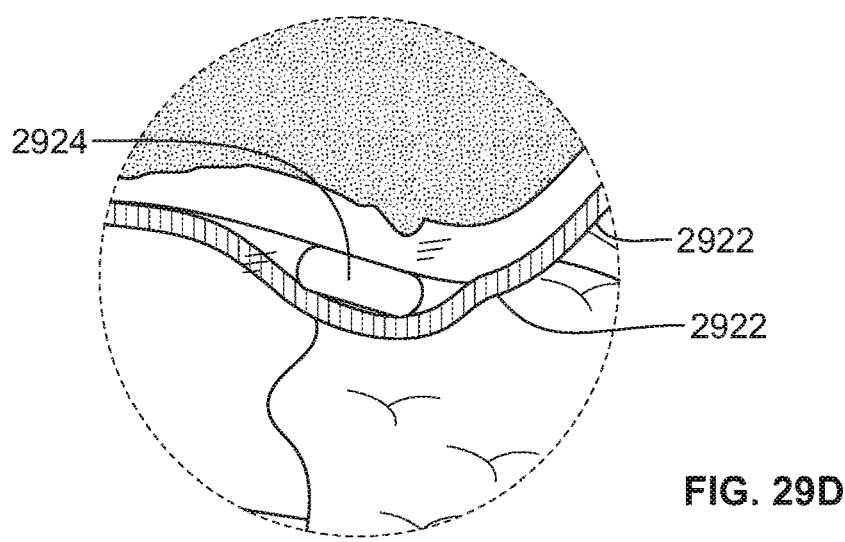

FIG. 29C shows another section medial view of an eye within the orbit of a patient's skull. The view of FIG. 29C corresponds to the view line 29C illustrated in FIG. 27C. The view of FIG. 29A is lateral and more medial than the view FIG. 29C. FIG. 29C includes the eye (2730) with upper lid (2720) and lower lid (2722), superior rectus (2725), lateral rectus (2750), inferior rectus (2754), and the lacrimal gland (2710). In some variations, as shown in FIG. 29C (and in an expanded view in FIG. 29D) a microstimulator (2924) may be positioned between the periosteum (2922) and the portion of the bone forming the fossa for the lacrimal gland (2780), such as shown in FIGS. 29A and 29B.

Figure 29E:
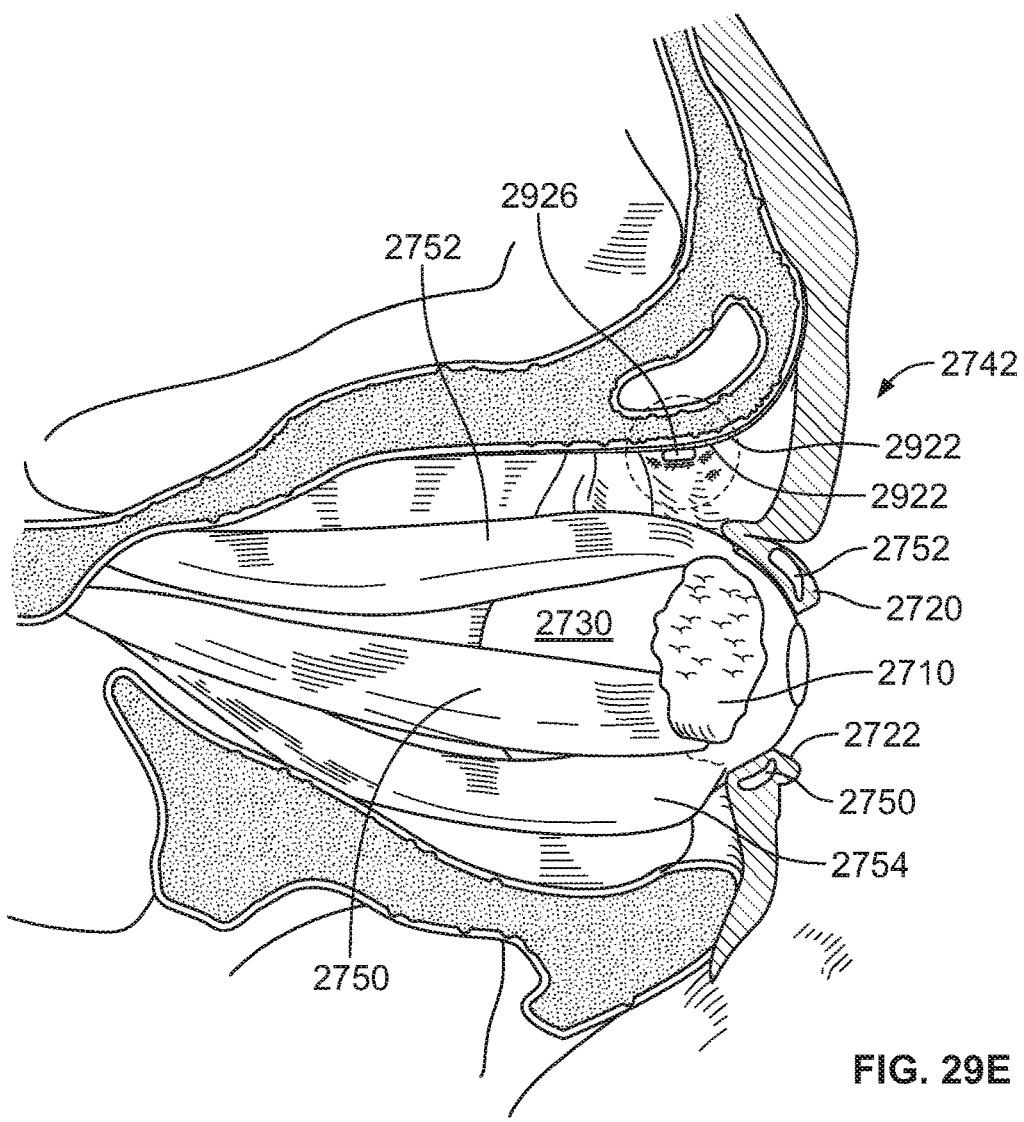
Figure 29F:
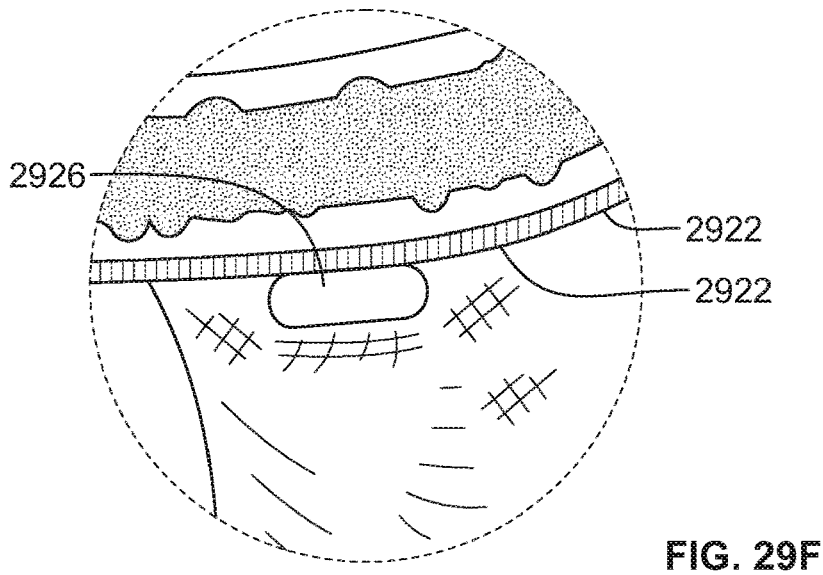

FIG. 29E is another section medial view of an eye within the orbit of a patient's skull. The view of FIG. 29E corresponds to the view line 29E illustrated in FIG. 27C. As shown in FIG. 29E (and in an expanded view in FIG. 29F), in some variations a microstimulator (2926) may be positioned between the periosteum (2922) and the lacrimal gland (2710).

Figure 29G:
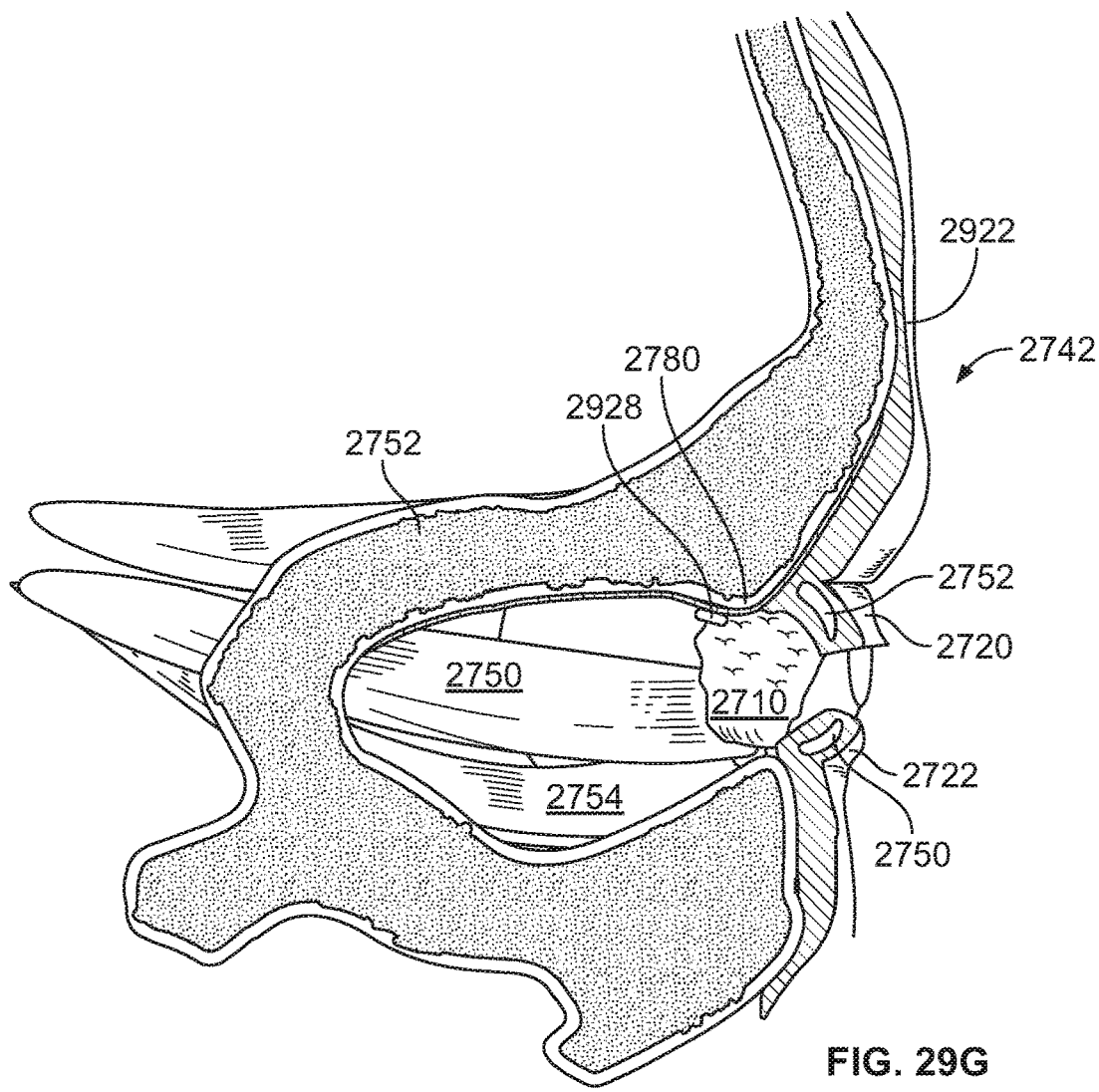
Figure 29H:
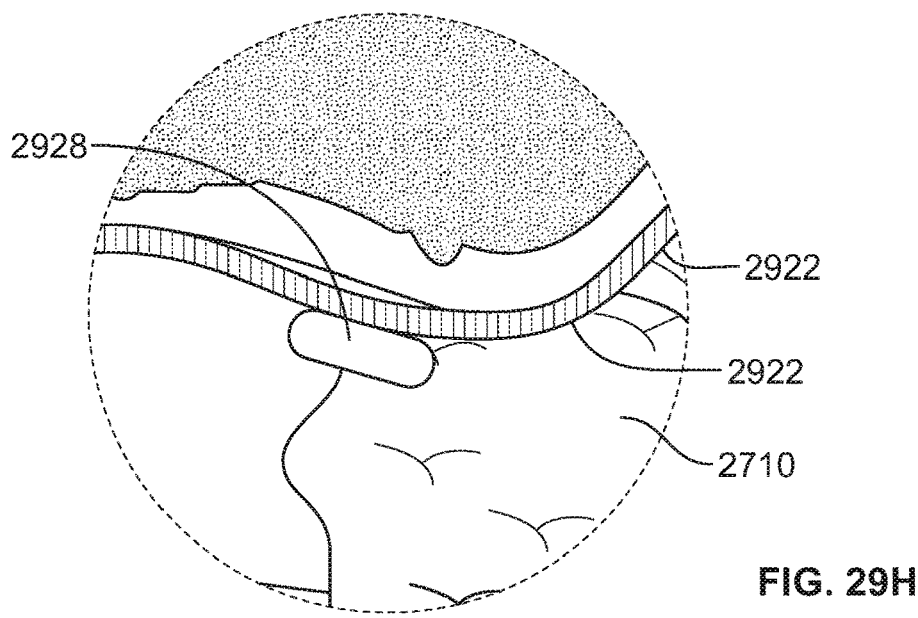

FIG. 29G is another section medial view of an eye within the orbit of a patient's skull. The view of FIG. 29G corresponds to the view line 29G illustrated in FIG. 27C. FIG. 29H is another enlarged section view of the inferior edge of the superior orbit having a microstimulator (2928). The position of microstimulator (2928) is similar to the positioning of microstimulator (2924) shown FIGS. 29C and 29D, except that the microstimulator (2928) is shown positioned between the periosteum (2922) and the lacrimal gland (2710).

Figure 32:
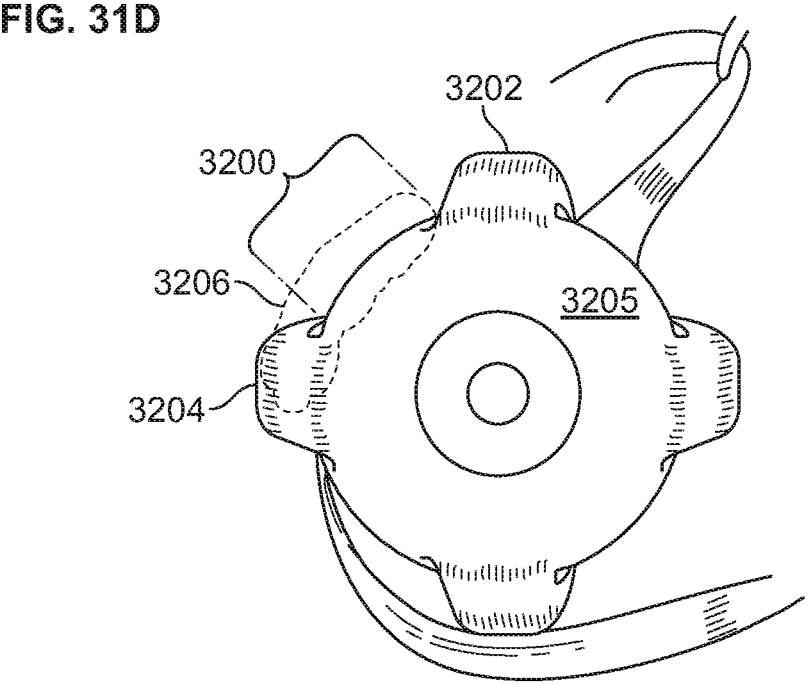
FIG. 32 depicts an example of an implantation location for the microstimulators described here.

FIG. 32 illustrates another implant zone (3200) for a microstimulator (not shown) or for one or more electrodes of a microstimulator. The microstimulator or electrodes thereof may be positioned within the fossa for the lacrimal gland of the orbit between the superior rectus muscle (3202) and the lateral rectus muscle (3204) of the eye (3205). When positioned there, the microstimulator may selectively stimulate an anatomical target such as a lacrimal gland (3206) without fully activating the extraocular muscles. For example, stimulation of the lacrimal gland may be sufficient to produce lacrimation or vasodilation of glandular blood vessels without engaging the extraocular muscles that would move the eye in a horizontal or vertical direction.

The microstimulators or electrodes thereof may be positioned in or adjacent to any of the bony structures and regions of the skull that provide access to one or more of the anatomical targets specific to the process of lacrimation, such as those shown in FIG. 27D. Some of the bony structures and regions include, but are not limited to, the sphenoid bone (2736), inferior orbital fissure (2735), the infraorbital foramen (2762), the maxillary axis (2764), the nasal-maxillary area (2766), the nasal cavity (2768), the fossa for the lacrimal sac (2732), the posterior lacrimal crest (2734), the inferior medial aspect of the supraorbital process (2772), the superior orbital fissure (2733) and the fossa for the lacrimal gland (2780).

Figure 33:
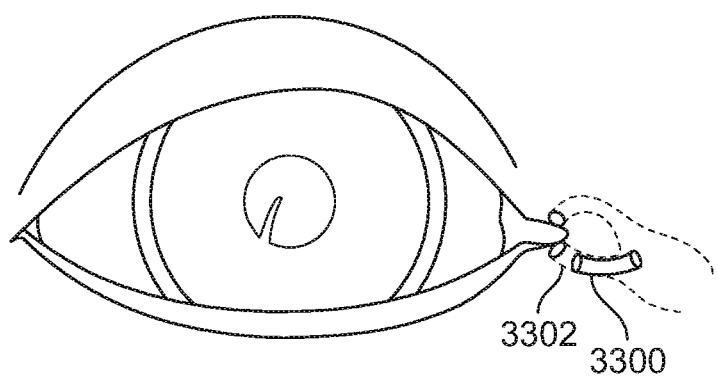
FIG. 33 depicts one variation of the microstimulators described here implanted in a lacrimal duct.

In some variations, one or more microstimulators may be positioned on a surface of the eye, such as microstimulator (620) described above with respect to FIG. 6G. Additionally or alternatively, one or more microstimulators or electrodes therein may be positioned in one or more puncta, lacrimal ducts and/or nasolacrimal ducts. For example, FIG. 33 shows one variation in which a microstimulator (3300) is positioned at least partially within a lacrimal duct (3302). In these variations, a current may be delivered to one or more afferents (e.g., afferents in the ocular surface, afferents in the lacrimal or nasolacrimal ducts), which may result in reflexive tear production. The microstimulator (3300) may be any of the microstimulators described in more detail above, and may be powered in any suitable manner as described in more detail above.

Figure 31A:
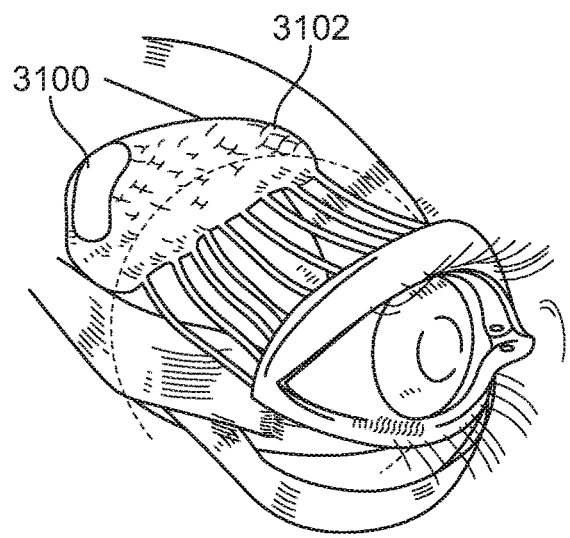
FIGS. 31A-31D depict different variations of microstimulators implanted near the lacrimal gland.

It should be appreciated that any of the microstimulators described above may be implanted on or adjacent an anatomical target such as a lacrimal gland. FIGS. 31A-31D illustrate different variations of microstimulators which are positioned on or adjacent a lacrimal gland of a patient. FIG. 31A is a perspective view of a patient's eye with one variation of a microstimulator (3100). The microstimulator (3100) may be a planar pliable microstimulator, such as the microstimulator (606) discussed above with respect to FIG. 6D. The planar pliable device is shown in FIG. 31A as being positioned on or adjacent to the lacrimal gland (3102) and has been unfurled such that a surface of the microstimulator expands over a portion of the surface of the lacrimal gland.

Figure 31B:
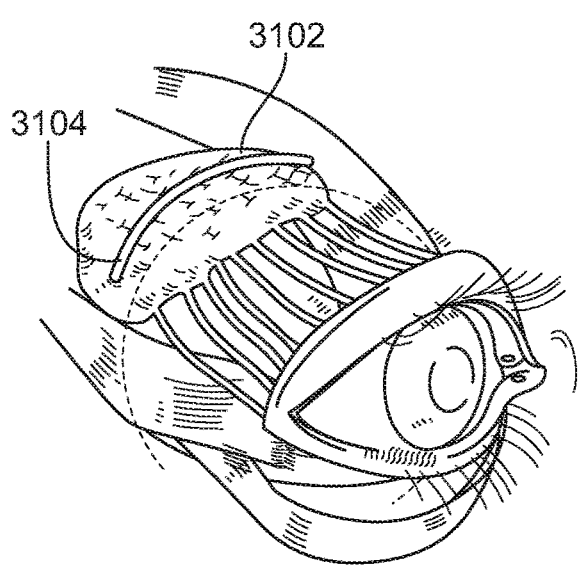

FIG. 31B is a perspective view of a patient's eye with another exemplary microstimulator (3104). The microstimulator (3104) may be a curved microstimulator, such as the microstimulator (604) discussed above with respect to FIG. 6B. The curved microstimulator (3104) positioned on or adjacent the lacrimal gland (3102) and curves to conform to an anatomical structure of a patient, such as the fossa for the lacrimal gland.

Figure 31C:
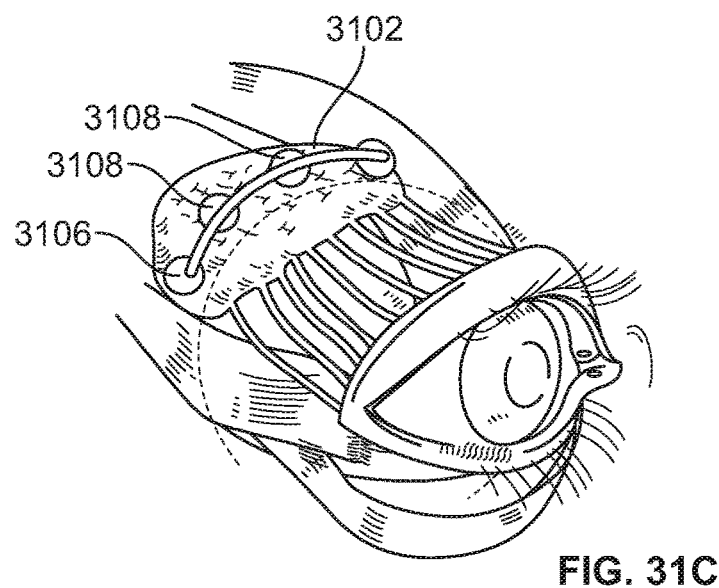

FIG. 31C is another perspective view of a patient's eye with an exemplary microstimulator (3106). The microstimulator (3106) may comprise a flexible segmented microstimulator, such as microstimulator (608) shown in FIG. 6E. The microstimulator (3106) may comprise a curved shape which may conform to an anatomical structure of a patient, such as a fossa for a lacrimal gland, and may comprise a plurality of electrodes (3108) as described in more detail above.

Figure 31D:
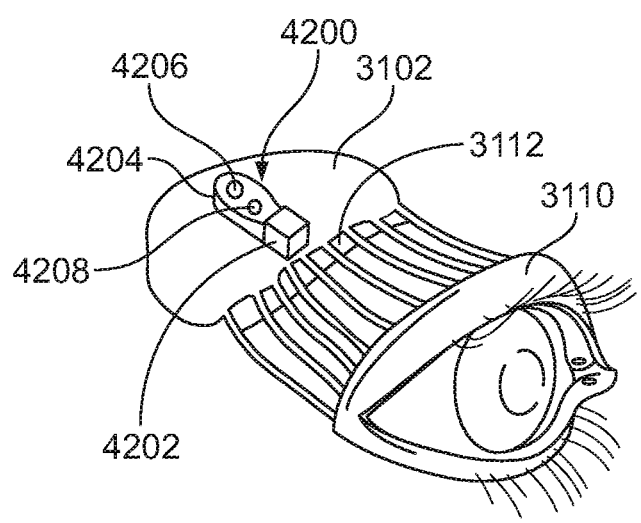

FIG. 31D is another perspective view of a patient's eye with the microstimulator (4200) described above in relation to FIGS. 42A-42C. As shown there, the microstimulator (4200) may be position on or adjacent the lacrimal gland (3102), such that the first (4206) and second (4208) electrodes are facing the lacrimal gland (3102). In some instances, as shown in FIG. 31D, the microstimulator (4200) may be positioned first electrode (4206) is distally of the second electrode (4208) relative to the upper lid (3110). In these variations, tissue stimulating currents may be directed out of the first electrode (4206), which may reduce extraneous tissue stimulation around the conjunctiva (3112). Additionally, as shown in FIG. 31D, the housing (4202) (or another end) of the microstimulator (4200) may be positioned against or near the conjunctiva (3112), which may facilitate retrieval of the microstimulator. For example, the housing (4202) of the microstimulator (4200) may be positioned such that it is visible through the conjunctiva when the upper lid (3110) is lifted. In some variations, one or more portions of the microstimulator (4200) may be colored to increase the visibility of the microstimulator (4200). To remove the microstimulator (4200), a physician may cut the conjunctive overlying the microstimulator (4200), and may grasp the microstimulator (4200) with a retrieval tool such as forceps.

While discussed above as being implanted in, on, or near one or more structures around the ocular cavity, it should be appreciated that microstimulators described here may be implanted in any suitable location. In some variations, a microstimulator may be implanted in a location to provide stimulation to one or more target nerves. For example, the microstimulator may be positioned to stimulate an occipital nerve (e.g., to treat headache or other pain), a vagus nerve (e.g., to treat epilepsy, depression, or the like), a dorsal genital nerve (e.g., to treat erectile or sexual dysfunction, urinary incontinence, or the like), or the like. When positioned to stimulate a nerve, in some instances the electrodes of the microstimulators may be located on the epineurium of a nerve or away from the portion of the nerve that innervates tissue or gland. An example of a direct nerve stimulator is a nerve cuff which includes electrodes carried on the inside walls of a cylindrical polymeric sheath. The nerve cuff may be wrapped around the nerve to bring the electrodes into direct contact with an isolated portion of a nerve to be stimulated. Indirect stimulation of a nerve may include delivering low amplitude electrical stimulation via electrodes that are in close proximity, but not in direct contact, with the nerve to be stimulated. Nerves that are in a bundle, plexus or innervating tissue or a gland are not isolated from other nerves or structures. Target nerves or structures that are not isolated may stimulated indirectly by using electrical selectivity.

In other variations, one or more microstimulators may be implanted in one or more locations in or around the mouth or salivary glands. For example, in some variations a microstimulator may be positioned in, on, or around a submandibular gland, a parotid gland, a sublingual gland, or the like. In these variations, the stimulation systems may be used to provide stimulation (as described hereinthroughout) to one or more of these anatomical targets to treat one or more conditions such as dry mouth. The microstimulator may be implanted using any suitable approach. For example, in some variations, a microstimulator may be placed subcutaneously to position the microstimulator in, on, or around the sublingual gland. When positioning a microstimulator in, on, or around the submandibular gland or the sublingual, the microstimulator may be advanced through the floor of the mouth, or may be advanced using a submandibular approach. The microstimulator may be delivered using one or more of the delivery systems described above.

Figure 34:
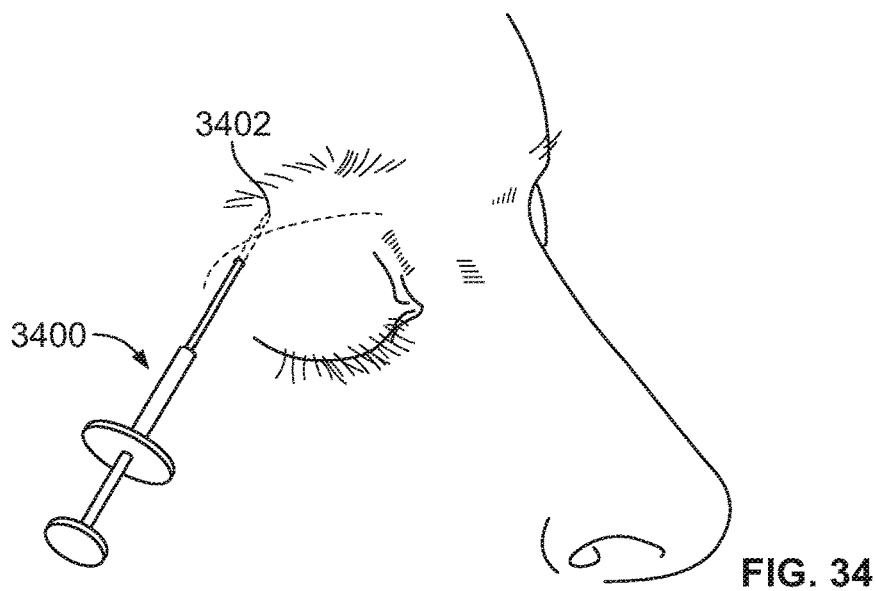
FIG. 34 depicts one variation of a method by which a microstimulator may be delivered to a patient.

The microstimulators described here may be delivered in any suitable manner. Described here are delivery systems and methods for delivering a microstimulator to a region of tissue. The delivery systems generally comprise at least one insertion device, and in some variations may comprise a dissection tool. Delivery of the microstimulators may be done under direct visualization and/or indirect visualization (e.g., ultrasound, fluoroscopy, or the like). FIG. 34 illustrates one instance in which an insertion device (3400) may be used to implant a microstimulator (3402) into a patient. As shown there, the insertion device (3400) may insert the microstimulator (3402) through an insertion region near the fossa for the lacrimal gland. In some variations, the microstimulator (3402) may be secured within the insertion device (3400) while being positioned within the patient. Once the insertion device has positioned the microstimulator (3402) at a desired location within the patient, the insertion device (3400) may deploy the microstimulator (3402) in the patient.

Figure 35A:
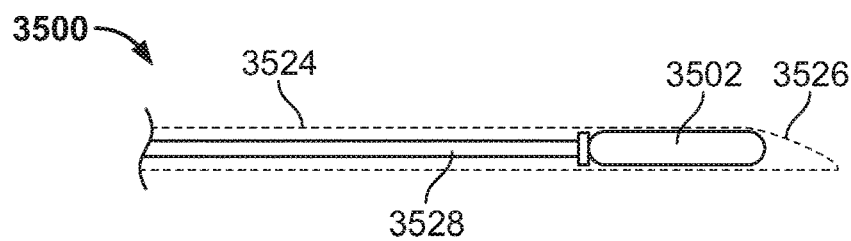
FIGS. 35A and 35B depict side views of a variation of an insertion device suitable for use with the delivery systems described here.
Figure 35B:
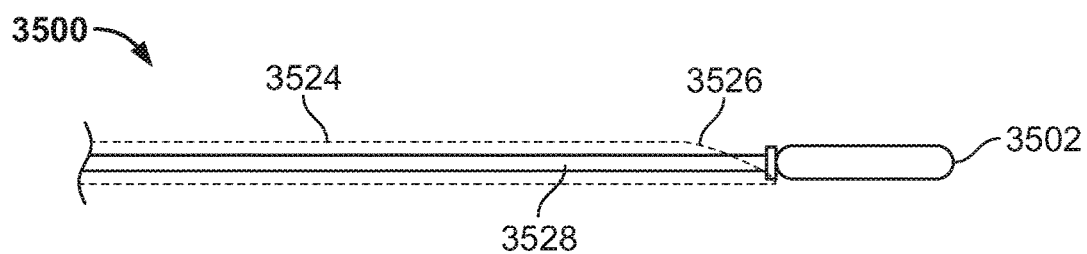

FIG. 35A shows a side view of one variation of an insertion device (3500) which may be used to deliver a microstimulator (3502). As shown there, the insertion device (3500) includes a housing (3524), a distal end (3526), and a device shaft (3528). The microstimulator (3502) may be secured near the distal end (3526) of the insertion device (3500). Insertion device (3500) may position the microstimulator (3502) at or adjacent an anatomical target, such as a lacrimal gland, within a patient while the microstimulator (3502) is secured to the insertion device (3500). In some variations, the insertion device (3500) may include a needle (e.g., a 12 or larger gauge needle). As shown in FIG. 35B, microstimulator (3502) may be released from the insertion device (3500) by withdrawing the device housing (3524) relative to the device shaft (3528) (or by advancing the device shaft (3528) relative to the device housing (3524)). In some variations the insertion device (3500) may contain elements for positioning the insertion device in a location which facilitates safe and accurate delivery of the microstimulator (3502). The insertion device may house the microstimulator (3502) in a non-needle cannula.

Figure 38:
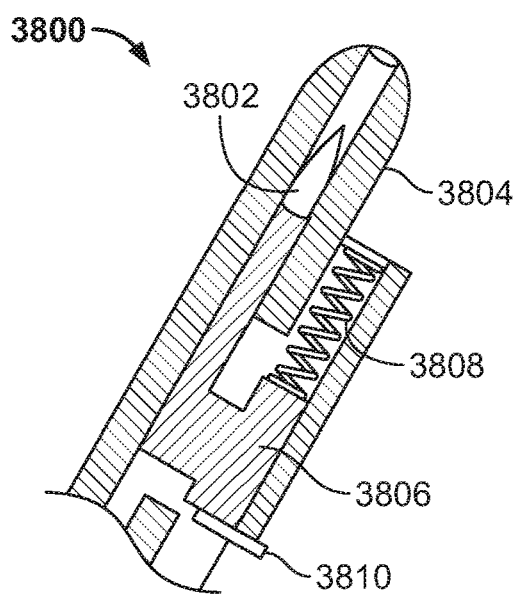
FIG. 38 depicts a variation of an insertion device suitable for use with the delivery systems described here.

The insertion device may contain one or more energy storage devices to facilitate insertion, for example a spring. The insertion device may contain an element by which the implanting physician triggers the insertion or deployment of the microstimulator, such as a plunger or button. FIG. 38 shows one such variation of an insertion device (3800) that may be used to deliver a microstimulator (3802), which may one or more of the microstimulators described above. As shown there, the insertion device (3800) may comprise a housing (3804) having a piston assembly (3806) and a spring (3808) housed therein, and a trigger member (3810). The spring (3808) may connect a portion of the piston assembly (3806) to the housing (3804), such that energy stored in the spring (3808) may move the piston assembly (3806) relative to housing (3804). For example, as shown in FIG. 38, the piston assembly (3806) may be retracted such that the spring (3808) may be stretched, and the piston assembly (3806) may be held in a cocked position (e.g., via the trigger member (3810)). The trigger member (3810) may be actuated to release the piston assembly (3806) relative to the housing (3804). The spring (3808) may then bias towards an unstretched configuration, which may pull the piston assembly (3806) towards the distal end of the insertion device (3800). As the piston assembly (3806) moves forward, it may advance the microstimulator (3802) out of the housing (3804), thereby delivering the microstimulator (3802). While shown in FIG. 38 as being stretched when the piston assembly (3806) is cocked, in some instances the spring (3808) may be configured such that it is compressed when the piston assembly (3806) is cocked.

Figure 39:
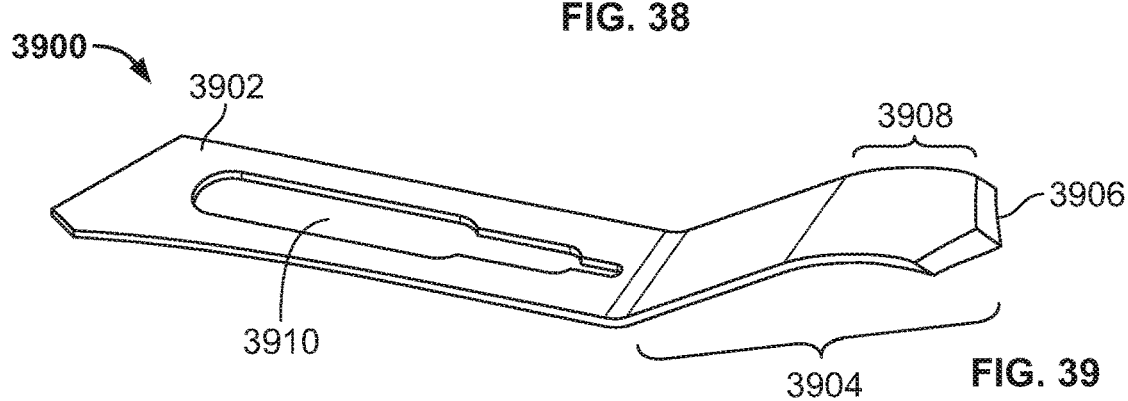
FIG. 39 depicts a variation of a dissection tool suitable for use with the delivery systems described here.

In some variations, the delivery systems may comprise one or more dissection tools which may be used to form an insertion pathway from outside a patient to a delivery location for a microstimulator. For example, FIG. 39 shows one variation of a dissection tool (3900) which may be used to form an insertion pathway into the orbit of the eye. As shown there, the dissection tool (3900) may comprise a base member (3902) and an insertion portion (3904). The insertion portion (3904) may include a cutting edge (3906) at a distal end thereof, which may sever tissue as the dissection tool (3900) is advanced into tissue. The cutting edge (3906) may include a single bevel, double bevel, a rounded point, or the like. While shown in FIG. 39 as having a single cutting edge (3906), it should be appreciated that in some instances the dissection tool (3900) may comprise two or more cutting edges, which may help the dissection tool (3900) to maintain an intended course during advancement. In some variations, the insertion portion (3904) may comprise a curved section (3908) which may allow the insertion portion (3904) to curve around the bony socket of the skull during insertion. Additionally or alternatively, in some variations, the insertion portion (3904) may be angled relative to the base member (3902). The angle between the insertion portion (3904) and the base member (3902) may be any suitable angle (e.g., between about 10 degrees and about 170 degrees), and may allow a physician easier access to the orbit with the insertion portion (3904) without the base member (3902) being blocked or impeded by the cheek or another portion of the face. In the variation of dissection tool (3900) shown in FIG. 39, base member (3902) may comprise an aperture (3910) which may allow the dissection tool to be connected to a handle (e.g., a scalpel handle, an insertion device, or the like). In other variations, the dissection tool may comprise a handle integrally connected to the base member. Additionally or alternatively, in some variations, a portion of the dissection tool (3900) may be configured to vibrate during advancement to assist in cutting tissue.

FIGS. 40A-40D illustrate a method by which a microstimulator may be placed on or adjacent the lacrimal gland using the delivery systems described here. Initially, the upper lid (4002) may be lifted relative to the eye (4000), as shown in FIG. 40A, which may reveal the conjunctiva. In some variations, the lid may be held open by hand, or using one or more tools. In some variations an insertion device or dissecting tool may comprise one or more components which may hold the lid in a lifted configuration. The physician may locate the lacrimal gland visually and/or or using one or more indirect visualization, and may advance a dissection tool (4008) to cut the conjunctiva and form an insertion pathway between the lacrimal gland (4004) and the orbit (4006), as shown in FIG. 40B. The dissection tool (4008) may be any suitable dissection tool, such as the dissection tool (3900) described above in relation to FIG. 39. In some variations, the dissection tool (4008) may be advanced such that it cuts through a portion of the periosteum (not shown) and the insertion pathway is formed between the periosteum and the orbit (4006). In other variations, the dissection tool (4008) is advanced such that it does not cut through the periosteum and the insertion pathway is formed between the periosteum and the lacrimal gland (4004). In still other variations, the insertion pathway may be formed in a portion of the lacrimal gland (4004), which may allow a portion of the microstimulator to be positioned within the lacrimal gland.

Once an insertion pathway is formed, an insertion device (4010) may be advanced through the insertion pathway. In some variations, the dissection tool (4008) may be partially or fully withdrawn prior to advancing the insertion device (4010). In some variations, the insertion device (4010) is advanced along the dissection tool (4008) to introduce the insertion device (4010) at least partially into the insertion pathway, as shown in FIG. 40C. Once the insertion device (4010) is in place, a microstimulator (4012) may be delivered from the insertion device (4010) into the insertion pathway, and the delivery tools may be removed, as shown in FIG. 40D. In some variations, the insertion device may not be introduced into the insertion pathway, but may instead push or otherwise advance the microstimulator (4012) into the insertion pathway over the dissection tool (4008).

While the dissection tool (4008) is shown in FIGS. 40A-40D as being separate from the insertion device (4010), it should be appreciated that in some variations an insertion device may comprise a dissection tool component which may create an insertion pathway. In other variations, the dissection tool may be configured to house and eject a microstimulator, such that the dissection tool may be configured to deliver the microstimulator.

In some variations, the delivery systems may comprise a guiding element for helping to direct or otherwise position one or more dissection tools and/or insertion devices of the delivery system. For example, FIG. 41 depicts one variation of a guiding element (4100) suitable for use with the delivery systems described here. As shown there, the guiding element (4100) may comprise a base (4101) and a guide cannula (4102) extending therefrom. The guide cannula (4102) may comprise a lumen (4104) extending through the guide cannula (4102) and the base (4101), such that one or more delivery tools (e.g., a dissection tool, an insertion device, or the like) may be advanced therethrough. The base (4101) may be positioned on one or more surfaces of the patient (e.g., over the eye, on the forehead, on the cheek, combinations thereof or the like) to align the guide cannula (4102) with an insertion site for the microstimulator. In some variations, the angle or pitch of the guide cannula (4102) relative to the base may be adjustable. Once the guide cannula (4102) is aligned with the intended insertion site for the microstimulator, one or more delivery tools may be advanced through the lumen (4104) to deliver a microstimulator to the insertion site, as described in more detail above. As the delivery tools are passed through the lumen (4104), the guide cannula (4102) may act to align the delivery tools relative to the insertion site. This may help provide more accurate placement of the microstimulator relative to tissue. Additionally, when placed over one or more structures of the body (e.g., the eye), the base (4101) may protect these bodily structures and may prevent unintended damage to tissue.

Either during or after placement of the microstimulator, a physician may test one or more stimulation parameters of the stimulation system. For example, a test signal may be applied to the patient using the microstimulator, one or more electrodes incorporated into the delivery system, a percutaneous needle stimulator, or the like. The physician may assess one or more outcomes of the test signal, such as tear production, discomfort, sensation, or the like), and may alter stimulation parameters and/or positioning of the device. For example, in some variations, the microstimulator may be repositioned if the test signal does not result in adequate tear production, or if the test signal results in discomfort in the patient. Additionally or alternatively, one or more stimulation parameters (e.g., pulse width, amplitude, etc.) may be adjusted depending on the results of the test signal. In some variations, this may comprise adjusting one or more adjustable elements of the microstimulator, as described in more detail above. The stimulation parameters and/or positioning of the microstimulator may be repeated as necessary to achieve a desired stimulation outcome.

Once the microstimulator is in place relative to the body, the microstimulator may be used to deliver stimulation to one or more tissues. For example, when used to treat dry eye, stimulation may be applied to the lacrimal gland. The stimulation may selectively stimulate one or more nerves that innervate the lacrimal gland. In some variations, the stimulation only stimulates one or more nerves that innervate the lacrimal gland. In other variations, the stimulation may be applied to tissue in or around the puncta, lacrimal ducts and/or nasolacrimal ducts.

When stimulating one or more of the nerves or tissues described above, it may be desirable to stimulate these nerves without stimulating the ocular muscles discussed above. The autonomic efferent fibers may be selectively stimulated over the sensory afferent fibers and the A-delta pain fibers. The efferent fibers may be selectively stimulated over the C pain fibers. In some variations it may be desirable to select a pulse width that stimulates efferent fibers over pain fibers. In some of these variations, stimulation using short pulse widths (e.g., 50 μsec-300 μsec) may bias stimulation toward efferent fibers.

The stimulation signal produced by the microstimulator may include a pulse amplitude, a pulse width, and a pulse frequency. One or more of the pulse amplitude, pulse width, or pulse frequency may be varied over the treatment period. The stimulation signal may include a current having a pulse amplitude between about 500 μA to about 25 mA. The stimulation signal may have a pulse frequency between about 2 Hz to about 200 Hz. The pulse frequency may be between about 30 Hz to about 40 Hz. The stimulation signal may include a current having a pulse width between about 50 μsec to about 2000 μsec. In some variations, the stimulation may be adjusted in response to a measured variable. The stimulation signal may be delivered in bursts and may include a current having a pulse width between about 100 μsec to about 1000 μsec. Stimulation using these stimulation parameters may be used to treat dry eye, as described herein.

The stimulation may be delivered in a pattern. The patterned stimulation may be used to ensure the comfort of the patient. The patterned stimulation may be used to efficacy of the stimulation. The stimulation may be delivered periodically at regular or irregular intervals. Stimulation bursts may be delivered periodically at regular or irregular intervals. The stimulation amplitude, pulse width or frequency may be modified during the course of stimulation. For example, the stimulation amplitude may be ramped from a low amplitude to a higher amplitude over a period of time. Stimulation amplitude may be ramped from a high amplitude to a lower amplitude over a period of time. Stimulation pulse width may be ramped from a low pulse width to a higher pulse width over a period of time. Stimulation pulse width may be ramped from a high pulse width to a lower pulse width over a period of time. The ramp period may be between 1 second and 15 minutes. The ramp period may be between 5 seconds and 30 seconds. Stimulation may be delivered at night time. Stimulation may only be delivered at night time. Stimulation may consist of very high frequency pulses to block activity in the target tissue. These very high frequency pulses may be of a frequency between 1,000 Hz and 100,000 Hz.

As mentioned above the stimulation provided by the microstimulator may be generated in response to an output signal produced by a controller. In these variations, a controller may be activated to initiate the output signal of a controller, and the controller may be brought near a receiving portion of the microstimulator to transmit the output signal to the controller. In some variations, this may comprise connecting or otherwise affixing the controller to a portion of the anatomy. For example, in variations where a microstimulator is positioned in, on, or around the lacrimal gland, a controller may be positioned near the ocular cavity of the patient. For example, in variations where the controller comprises a patch, the patch may be positioned on the temple, brow, forehead, cheek, or other suitable location of the patient. The patch may be held in place via an adhesive (as described in more detail above) or via one or more magnets in the controller (which may be attracted to one or more magnets positioned within the patient). In variations where a stimulation system comprises an implanted controller, the controller may be programmed to output the output signal on a timed basis and/or may be configured to produce an output signal in response to a signal received from an external programmer.

When the stimulation systems described here are used to treat dry eye by stimulating one of the anatomical structures listed above, such as the lacrimal gland, it may be desirable to first evaluate whether the use of the stimulation systems described here is appropriate for a patient. For example, in some patients, the lacrimal gland may be irreparably damaged to the point where it is unable to secrete tears. In these variations, a test may be conducted to evaluate whether the lacrimal gland is capable of secreting tears. In some variations, one or more stimulation signals may be administered to the lacrimal gland prior to or during delivery of a microstimulator. For example, a transcutaneous skin stimulator or a percutaneous needle stimulator may be used to provide a test signal to the lacrimal gland, and a physician or other user may evaluate a physiological response from the patient (e.g., tear production). The test signal may be configured such that if administration of the test signal produces a physiological response from the patient, then treatment using the stimulation systems described here is appropriate for that patient. It should be appreciated that one or more electrodes may be incorporated into one or more of the insertion devices described above, such that one or more test signals may be administered during delivery of a microstimulator to a patient.

When the stimulation systems and methods described above are used to treat dry eye, it should be appreciated that the stimulation provided by the stimulation current may be configured to rehabilitate the lacrimal gland. In these variations, a treatment regimen may be supplied to the lacrimal gland to improve the functioning of the lacrimal gland over time. In some instances, a treatment regimen may comprise stimulating the lacrimal gland at predetermined times (e.g., daily stimulation), or the like. The stimulation provided by the microstimulator may comprise any suitable stimulation parameters, such as those described in more detail above.

While the methods described above discuss delivering electrical stimulation to one or more anatomical tissues, it should be appreciated that the stimulation systems may additionally or alternatively stimulate tissue using one or more chemical, optical, magnetic, thermal, and/or acoustic stimulation. For example, when the methods described above are used to treat dry eye, it may be desirable to additionally or alternatively provide one or more drugs or active agents to one or more of the anatomical structures described in more detail above (such as the lacrimal gland). The agents delivered may any suitable agent or combination of agents (such as pilocarpine or one or more parasympathetic agents), and may be delivered in any suitable manner. In some variations, the microstimulator may be configured to release one or more drugs or active agents therefrom. Additionally or alternatively, a drug-releasing implant may be delivered to the lacrimal gland, the fossa for the lacrimal gland, the fornix, a lacrimal duct, the eye (e.g., via a contact lens). For example, one or more biodegradable depots comprising one or more agents (e.g., pilocarpine) may be implanted in, on, or near the lacrimal gland. The depot or depots may comprise one more biodegradable polymers (e.g., PLA, PLGA, combinations thereof, or the like), and may be configured to release the one or more agents over a certain period of time (e.g., one weeks, two weeks, one month, or the like). Additional depots may be implanted to prolong administration of the one or more agents to the lacrimal gland.

In some variations, the methods described here may additionally comprise providing optical stimulation to an anatomical target such as the lacrimal gland. For example, optical stimulation may comprise photo-electric activation of a drug (such as a drug released from one or more of the implants described above), infrared stimulation using a Vanderbilt/Jensen technique, or the like, or therapy using an optogenetics technique. In some variations, the methods described here may additionally comprise providing magnetic stimulation to one or more anatomical targets. For example, in some variations one or more external magnetic fields may be configured to induce a current in tissue. In some variations, the methods described here may comprise increasing or decreasing the temperature in or around a certain tissue to activate or otherwise assist in therapy of that tissue. In still other variations, the methods described here may comprise providing ultrasound or other acoustic energy to an anatomical target.

The stimulation systems and methods described above may be used to treat a number of conditions. For example, the stimulation devices described here may be used to stimulate one or more tissues in or around the eye to treat one or more conditions, including but not limited to, allergies, amblyopia, Bell's Palsy, blepharitis, corneal ulcers, eye occlusions, eye twitch, macular hole, nystagmus, ocular migraine, ocular rosacea, optic neuritis, photophobia, pinguecula, pterygium, ptosis, strabismus, uveitis, conjunctivitis, diabetic retinopathy, glaucoma (e.g., via ciliary body/nerve stimulation), keratoconus, macular degeneration, macular dystrophy, ocular hypertension, retinitis pigmentosa, Stargardt disease, diplopia, hyperopia, myopia, and presbyopia.

What is claimed as new and desired to be protected by Letters Patent of the United States is:

1. A method for treating urinary incontinence, comprising:
   using a microstimulator to treat urinary incontinence, wherein the microstimulator comprises a stimulation circuit without any internal logic or intelligence and without an internal battery, wherein the microstimulator is implanted in a location for stimulating a dorsal genital nerve of a patient to thereby treat the urinary incontinence, and wherein the microstimulator conforms to a shape of tissue surrounding the dorsal genital nerve of the patient; and
   wherein the microstimulator applies a stimulation signal to the dorsal genital nerve upon receipt of a waveform signal from a handheld controller, the waveform signal being transmitted from the handheld controller to the microstimulator when the handheld controller is moved into a vicinity of the microstimulator.

2. The method of claim 1, wherein the waveform signal from the handheld controller is wirelessly received by the microstimulator.

3. The method of claim 1, wherein a characteristic of the stimulation signal is at least partially dependent on a characteristic of the waveform signal from the handheld controller.

4. The method of claim 1, wherein the handheld controller generates the waveform signal in response to an input signal provided by the patient.

5. A method for stimulating a dorsal genital nerve of a patient to treat urinary incontinence, comprising:
   receiving an input signal by a handheld controller when the handheld controller is moved into a vicinity of an implanted microstimulator, wherein the microstimulator comprises a stimulation circuit without any internal logic or intelligence and without an internal battery, wherein the microstimulator is implanted to stimulate the dorsal genital nerve of the patient, wherein the input signal to the handheld controller results in an output of a waveform signal by the handheld controller to the microstimulator, and wherein the microstimulator conforms to a shape of tissue surrounding the dorsal genital nerve of the patient;

generating, by the microstimulator, a stimulation signal upon receipt of the waveform signal from the handheld controller when the handheld controller is moved into the vicinity of the microstimulator; and applying, by the microstimulator, the stimulation signal to the dorsal genital nerve to treat urinary incontinence.

6. The method of claim 5, wherein the microstimulator comprises a coil responsive to an induced field.

7. The method of claim 6, wherein the output of the waveform signal by the handheld controller is wirelessly received by the microstimulator.

8. The method of claim 1, wherein a characteristic of the stimulation signal is at least partially dependent on a characteristic of the waveform signal outputted by the handheld controller.

9. The method of claim 1, wherein the microstimulator comprises a planar structure.

10. The method of claim 1, wherein the microstimulator comprises a housing and a flexible extension connected to the housing.

11. The method of claim 10, wherein the housing comprises the stimulation circuit, and the flexible extension comprises an electrode and a coil.

12. The method of claim 11, wherein the electrode and coil are connected to the stimulation circuit via one or more feedthroughs.

13. The method of claim 1, wherein the input signal is provided by the patient.

14. The method of claim 1, wherein the input signal is provided by a health professional.

15. The method of claim 1, wherein providing the input signal comprises depressing a button.

16. The method of claim 1, further comprising altering the intensity of the stimulation signal.

17. A method for implanting a microstimulator and stimulating in a region of tissue, comprising:

delivering the microstimulator to the region of tissue using an insertion device, wherein the microstimulator comprises a stimulation circuit without any internal logic or intelligence and without an internal battery, wherein the region of tissue includes a dorsal genital nerve, and wherein the microstimulator conforms to a shape of the region of tissue surrounding the dorsal genital nerve of the patient; and stimulating, by the microstimulator, the dorsal genital nerve upon receipt of a waveform signal from a handheld controller, the waveform signal being delivered from the handheld controller to the microstimulator when the handheld controller is moved into a vicinity of the microstimulator.

18. The method of claim 17, wherein the microstimulator is delivered under direct visualization.

19. The method of claim 17, wherein the microstimulator is delivered under indirect visualization.

20. The method of claim 17, wherein the microstimulator comprises a coil responsive to an induced field.

21. The method of claim 17, wherein the microstimulator comprises a planar structure.

22. The method of claim 17, wherein the microstimulator comprises a housing and a flexible extension connected to the housing.

23. The method of claim 22, wherein the housing comprises the stimulation circuit, and the flexible extension comprises an electrode and a coil.

24. The method of claim 23, wherein the electrode and coil are connected to the stimulation circuit via one or more feedthroughs.

* * * * *